(12) United States Patent
Ashford et al.

(10) Patent No.: US 10,314,920 B2
(45) Date of Patent: Jun. 11, 2019

(54) THERAPEUTIC DENDRIMERS

(71) Applicant: ASTRAZENECA AB, Södertäljie (SE)

(72) Inventors: Marianne Bernice Ashford, Cheshire (GB); Iain Grant, Cheshire (GB); Edward John Hennessy, Waltham, MA (US); William McCoull, Macclesfield (GB); Michael Giannis, Victoria (AU); Brian Kelly, Victoria (AU); David Owen, Victoria (AU); John Paul Secrist, Waltham, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 15/899,892

(22) Filed: Feb. 20, 2018

(65) Prior Publication Data

US 2018/0264127 A1     Sep. 20, 2018

Related U.S. Application Data

(60) Provisional application No. 62/591,823, filed on Nov. 29, 2017, provisional application No. 62/488,151, (Continued)

(51) Int. Cl.
    *C07D 211/20*   (2006.01)
    *A61K 47/30*   (2006.01)
    (Continued)

(52) U.S. Cl.
    CPC .......... *A61K 47/641* (2017.08); *A61K 31/451* (2013.01); *A61K 47/60* (2017.08); (Continued)

(58) Field of Classification Search
    CPC .... A61K 47/641; A61K 47/60; A61K 31/451; A61P 35/00
    See application file for complete search history.

(56) References Cited

U.S. PATENT DOCUMENTS 4,289,872 A  *  9/1981  Denkewalter ........ C07K 14/001
                                                  528/310
4,410,688 A  *  10/1983  Denkewalter ............ C08H 1/00
                                                  528/310
(Continued)

FOREIGN PATENT DOCUMENTS

WO    2002/24636 A2   3/2002
WO    2005/049594 A1   6/2005
(Continued)

OTHER PUBLICATIONS

Boyd; Mol. Pharm. , 2006, 3, 614-627. (Year: 2006).*
(Continued)

*Primary Examiner* — Daniel R Carcanague
(74) *Attorney, Agent, or Firm* — Meaghan Lynn Richmond

(57) ABSTRACT

Disclosed are dendrimers of formula (I):

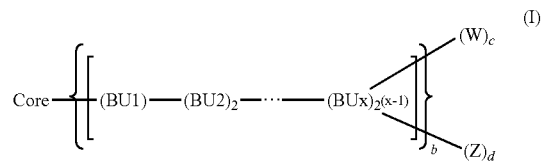

and pharmaceutically acceptable salts thereof. Also disclosed are pharmaceutical compositions comprising the dendrimer of formula (I) and methods of using the same for treating cancer.

16 Claims, 16 Drawing Sheets

Related U.S. Application Data filed on Apr. 21, 2017, provisional application No. 62/461,983, filed on Feb. 22, 2017.

(51) Int. Cl.

| | |
|---|---|
| A61K 47/42 | (2017.01) |
| A61K 47/60 | (2017.01) |
| A61P 35/00 | (2006.01) |
| A61K 31/451 | (2006.01) |
| A61K 47/64 | (2017.01) |
| C08G 69/10 | (2006.01) |
| C08G 69/40 | (2006.01) |
| C08G 83/00 | (2006.01) |

(52) U.S. Cl.
CPC .............. *A61P 35/00* (2018.01); *C08G 69/10* (2013.01); *C08G 69/40* (2013.01); *C08G 83/003* (2013.01)

(56) References Cited

U.S. PATENT DOCUMENTS

| | | | |
|---|---|---|---|
| 8,703,907 B2 | 4/2014 | Ashley | |
| 8,754,190 B2 | 6/2014 | Ashley | |
| 8,946,405 B2 | 2/2015 | Ashley | |
| 9,018,381 B2* | 4/2015 | Diebold | C07D 211/22 546/247 |
| 9,387,254 B2 | 7/2016 | Santi | |
| 9,744,264 B2 | 8/2017 | Matheny | |
| 2002/0086887 A1 | 7/2002 | Augeri | |
| 2009/0118467 A1* | 5/2009 | Krippner | A61K 31/785 530/323 |
| 2009/0324535 A1* | 12/2009 | Boyd | A61K 31/74 424/78.17 |
| 2010/0278750 A1* | 11/2010 | Krippner | A61K 49/124 424/9.34 |
| 2010/0292148 A1* | 11/2010 | Krippner | C07K 5/06026 514/10.7 |
| 2012/0035134 A1 | 2/2012 | Diebold | |
| 2014/0171375 A1* | 6/2014 | Owen | C08G 69/10 514/19.3 |
| 2016/0220689 A1* | 8/2016 | Owen | A61K 47/48215 |
| 2017/0189543 A1* | 7/2017 | Owen | A61K 47/48215 |
| 2017/0354739 A1* | 12/2017 | Owen | A61K 47/65 |

FOREIGN PATENT DOCUMENTS

| | | |
|---|---|---|
| WO | 2007/040650 A2 | 4/2007 |
| WO | 2007/082331 A1 | 7/2007 |
| WO | 2008/061208 A2 | 5/2008 |
| WO | 2009/036035 A1 | 3/2009 |
| WO | 2010/065865 A2 | 6/2010 |
| WO | 2010/138588 A2 | 12/2010 |
| WO | 2010/143074 A2 | 12/2010 |
| WO | 2011/149492 A1 | 12/2011 |
| WO | 2012/017251 A1 | 2/2012 |
| WO | 2015/035446 A1 | 3/2015 |

OTHER PUBLICATIONS

Kaminskas; Mol. Pharmaceutics, 2012, 9, 355-373. (Year: 2012).*
Kaminskas; Mol. Pharmaceutics 2009, 6, 1190-1204. (Year: 2009).*
Kojima; Expert Opinion on Drug Metabolism and Toxicology 2015, 11, 1303-1315. (Year: 2015).*
Varnes; Bioorganic & Medicinal Chemistry Letters 2014, 24, 3026-3033. (Year: 2014).*
Zhou; Angew Chem Int Ed Engl. 2014, 53, 10949-10955. (Year: 2014).*

Ansell et al., "Modulating the Therapeutic Activity of Nanoparticle Delivered Paclitaxel by Manipulating the Hydrophobicity of Prodrug Conjugates," Journal of Medicinal Chemistry, 2008, 51(11), 3288-3296.
Bi et al., "Multifunctional Poly(amidoamine) Dendrimer-Taxol Conjugates: Synthesis, Characterization and Stability," Journal of Computational and Theoretical Nanoscience, 2007, 4, 1179-1187.
Boyd et al. "Cationic Poly-l-lysine Dendrimers: Pharmacokinetics, Biodistribution, and Evidence for Metabolism and Bioresorption after Intravenous Administration to Rats," Molecular Pharmaceutics, 2006, 3(5), 614-627.
Bruncko et al. "Studies Leading to Potent, Dual Inhibitors of Bcl-2 and Bcl-xL," Journal of Medicinal Chemistry, vol. 50, No. 4, 2007, pp. 641-662.
Deng et al. "Bruton's tyrosine kinase inhibition increases Bcl-2 dependence and enhances sensitivity to venetoclax in chronic lymphocytic leukemia," Leukemia, 2017, 31(10), 2075-2084.
Fox et al., "Synthesis and In Vivo Antitumor Efficacy of PEGylated Poly(l-lysine) Dendrimer—Camptothecin Conjugates," Molecular Pharmaceutics, 2009, 6(5), 1562-1572.
Hauck et al., "Alterations in the Noxa-Mcl-1 Axis Determine Sensitivity of Small Cell Lung Cancer to the NH3 Mimetic ABT-737," Molecular Cancer Therapeutics, 2009, 8(4), 883-892.
Kaminskas et al., "Association of Chemotherapeutic Drugs with Dendrimer Nanocarriers: An Assessment of the Merits of Covalent Conjugation Compared to Noncovalent Encapsulation," Molecular Pharmaceutics, 2012, 9(3), 355-373.
Kaminskas et al., "Pharmacokinetics and Tumor Disposition of PEGylated, Methotrexate Conjugated Poly-l-lysine Dendrimers," Molecular Pharmaceutics, 2009, 6(4), 1190-1204.
Kojima, "Preclinical studies of dendrimer prodrugs," 2015, Expert Opinion on Drug Metabolism and Toxicity, 11(8), 1303-1315.
Lin et al., "'Seed' Analysis of Off-Target siRNAs Reveals an Essential Role of Mcl-1 Resistance to the Small-Molecule Bcl-2/Bcl-xL Inhibitor ABT-737," Oncogene, 2007, 26(27), 3972-3979.
Lim et al., "Design, Synthesis, Characterization and Biological Evaluation of Triazine Dendrimers Bearing Paclitaxel Using Ester and Ester/Disulfide Linkages," Bioconjugate Chemistry, 2009, 20, 2154-2161.
Matsumoto et al., "Controlled Drug Release: New Water-Soluble Prodrugs of an HIV Protease Inhibitor," Bioorganic and Medicinal Chemistry Letters, 2001, 11, 605-609.
Miller et al., "BH3 Mimetic ABD-737 and a Proteasome Inhibitor Synergistically Kill Melanomas Through Noxa-Dependent Apoptosis," Journal of Investigational Dermatology 2009, 129(4), 964-971.
Parajapati et al., Potential Application of Dendrimers in Drug Delivery: A Concise Review and Update, Journal of Drug Delivery and Therapeutics, 2016, 6(2), 71-88.
Robak et al. "Bcl-2 Inhibitors for Chronic Lymphocytic Leukemia," J. Leukemia Vo. 03, No. 03, Jan. 1, 2015.
Sugahara et al., "Paclitaxel Delivery Systems: The Use of Amino Acid Linkers in the Conjugation of Paclitaxel with Carboxymethyldextran to Create Prodrugs," Biological Pharmaceutical Bulletin, 2002, 25(5), 632-641.
Varnes et al., "Towards the next generation of dual Bcl-2/Bcl-xL inhibitors," Bioorganic and Medicinal Chemistry Letters, 2014, 24(14), 3026-3033.
Wendt, et al., "Discovery and Structure-Activity Relationship of Antagonists of B-Cell Lymphoma 2 Family of Proteins with Chemopotentiation Activity in Vitro and in Vivo," J Journal of Medicinal Chemistry, vol. 49, No. 3, 2006, pp. 1165-1181.
Zhou et al., "Molecularly Precise Dendrimer—Drug Conjugates with Tunable Drug Release for Cancer Therapy," Angewandte Chemie International Edition in English, 2014, 53m 10949-10955.
Zhu et al., "PEGylated PAMAM Dendrimer-Doxorubicin Conjugates: In Vitro Evaluation and In Vivo Tumor Accumulation," Pharmaceutical Research 2010, 27(1), 161-174.

* cited by examiner

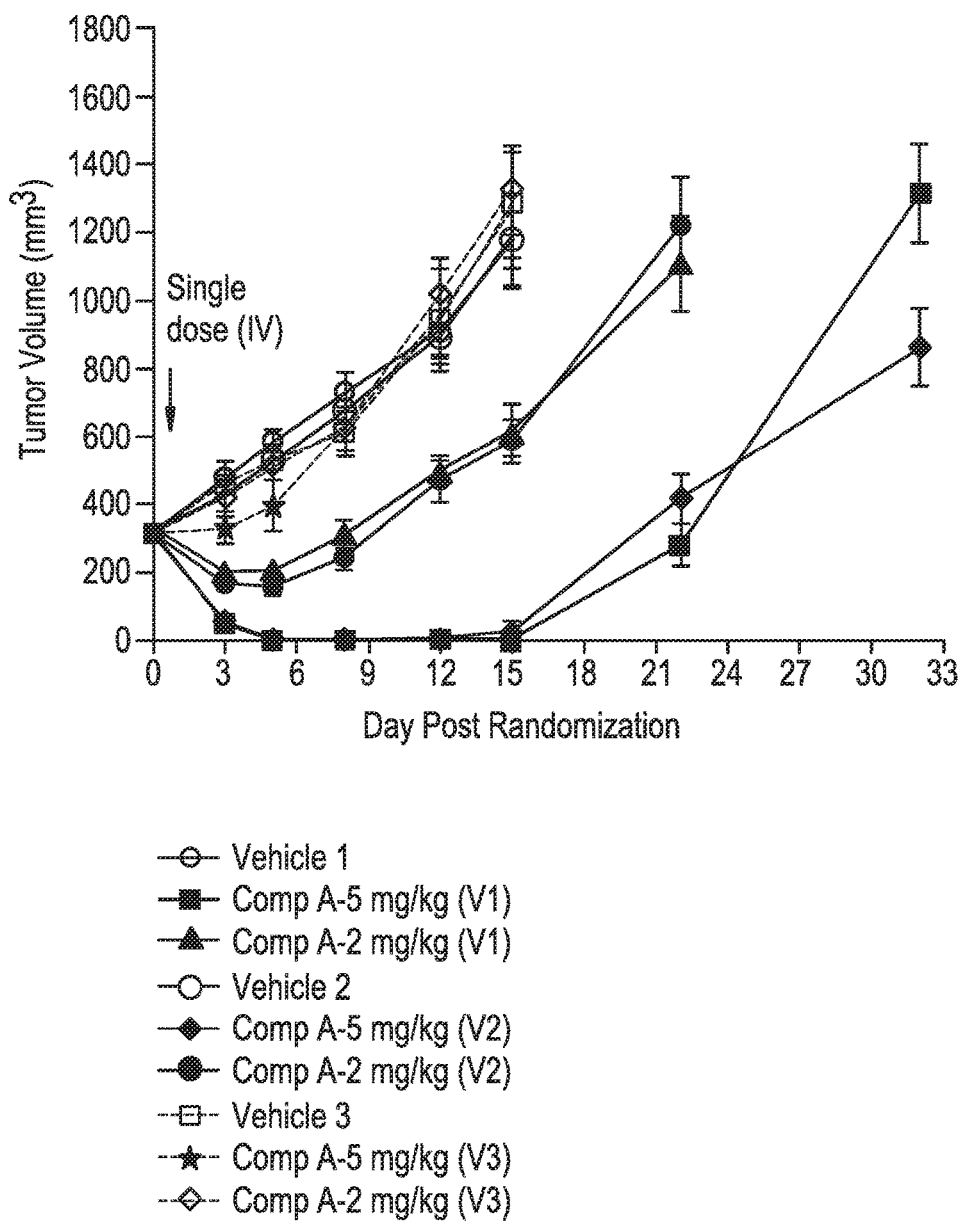

NCI-H1048

THERAPEUTIC DENDRIMERS

RELATED APPLICATIONS

This application claims the benefit of priority under 35 U.S.C. 119(e) of U.S. Provisional Application No. 62/461,983, filed Feb. 22, 2017, U.S. Provisional Application No. 62/488,151, filed Apr. 21, 2017 and U.S. Provisional Application No. 62/591,823, filed Nov. 29, 2017. Each of the foregoing applications are hereby incorporated by reference in their entirety.

BACKGROUND

Bcl-2 and Bcl-XL are important anti-apoptotic members of the BCL-2 family of proteins and master regulators of cell survival (Chipuk J E et al., The BCL-2 family reunion, *Mol. Cell* 2010 Feb. 12; 37(3):299-310). Gene translocation, amplification and/or protein over-expression of these critical survival factors has been observed in multiple cancer types and is widely implicated in cancer development and progression (Yip et al., Bcl-2 family proteins and cancer, *Oncogene* 2008 27, 6398-6406; and Beroukhim R. et al., The landscape of somatic copy-number alteration across human cancers, *Nature* 2010 Feb. 18; 463 (7283):899-905). In many malignancies, BCL-2 and/or BCL-XL have also been shown to mediate drug resistance and relapse and are strongly associated with a poor prognosis (Robertson L E et al. Bcl-2 expression in chronic lymphocytic leukemia and its correlation with the induction of apoptosis and clinical outcome, *Leukemia* 1996 Mar.: 10(3):456-459; and Ilievska Poposka B. et al., Bcl-2 as a prognostic factor for survival in small-cell lung cancer, *Makedonska Akademija na Naukite i Umetnostite Oddelenie Za Bioloshki i Meditsinski Nauki Prilozi* 2008 Dec.; 29(2):281-293).

Anti-apoptotic BCL2 family proteins promote cancer cell survival by binding to pro-apoptotic proteins like BIM, PUMA, BAK, and BAX and neutralizing their cell death-inducing activities (Chipuk J E et al., infra; and Yip et al, infra). Therefore, therapeutically targeting BCL-2 and BCL-XL alone or in combination with other therapies that influence the BCL-2 family axis of proteins, such as cytotoxic chemotherapeutics, proteasome inhibitors, or kinase inhibitors is an attractive strategy that may treat cancer and may overcome drug resistance in many human cancers (Delbridge, A R D et al., The BCL-2 protein family, BH3-mimetics and cancer therapy, *Cell Death & Differentiation* 2015 22, 1071-1080).

In addition to cell potency, in order to develop a candidate compound into a suitably acceptable drug product, the compound needs to possess and exhibit a host of additional properties. These include suitable physico-chemical properties to allow formulation into a suitable dosage form (e.g., solubility, stability, manufacturability), suitable biopharmaceutical properties (e.g., permeability, solubility, absorption, bioavailability, stability under biological conditions, pharmacokinetic and pharmacodynamic behavior) and a suitable safety profile to provide an acceptable therapeutic index. Identification of compounds, e.g., inhibitors of Bcl-2 and/or Bcl-XL that exhibit some or all of such properties is challenging.

Particular N-acylsulfonamide based inhibitors of Bcl-2 and/or Bcl-XL and methods for making the same are disclosed in U.S. Pat. No. 9,018,381. The activity and specificity of the compounds that bind to and inhibit Bcl-2 function in a cell has also been disclosed in U.S. Pat. No. 9,018,381 by way of in vitro binding and cellular assays.

However, delivery of these N-acylsulfonamide based inhibitors of Bcl-2 and/or Bcl-XL have proved difficult due to for example, low solubility and target related side effects. Applicants have therefore developed dendrimers linked to certain Bcl inhibitors that may overcome the delivery challenges faced by the unconjugated Bcl inhibitors.

BRIEF DESCRIPTION

Disclosed herein are dendrimers covalently attached (e.g., conjugated, or linked) to a Bcl inhibitor. The conjugated dendrimers exhibit high solubility compared to the unconjugated Bcl inhibitor, and preclinical data suggests that the dendrimers conjugated with the Bcl inhibitor have the potential to improve tolerability in vivo, which may improve therapeutic index and reduce side effects. The dendrimers are designed to have particular release rate (e.g., the rate at which the Bcl inhibitor is cleaved from the dendrimer).

In some embodiments, disclosed are dendrimers of formula (I):

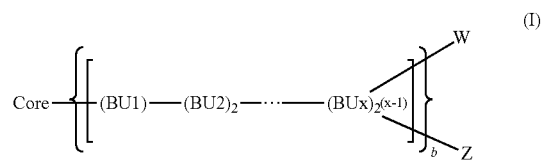

or a pharmaceutically acceptable salt thereof, wherein:
Core is

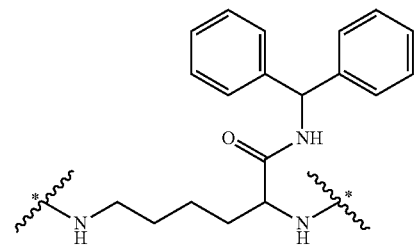 [SMILES: *NCCCCC(N*)C(=O)NC(c1ccccc1)c1ccccc1]

* indicates covalent attachment to a carbonyl moiety of (BU1);
b is 2;
BU are building units;
$BU_x$ are building units of generation x, wherein the total number of building units in generation x of the dendrimer of formula (I) is equal to $2^{(x)}$ and the total number of BU in the dendrimer of formula (I) is equal to $(2^x-1)b$; wherein BU has the following structure:

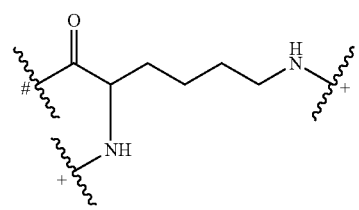 [SMILES: *NCCCCC(N*)C(*)=O]

# indicates covalent attachment to an amine moiety of Core or an amino moiety of BU;

+ indicates a covalent attachment to a carbonyl moiety of BU or a covalent attachment to W or Z;

W is independently $(PM)_c$ or $(H)_e$;
Z is independently $(L-AA)_d$ or $(H)_e$;
PM is $PEG_{900-1200}$ or $PEG_{100-2400}$;
L-AA is a linker covalently attached to an active agent; wherein L-AA is of the formula:

wherein
A is —N(CH₃), —O—, —S— or —CH₂—;
⊕ is the attachment point to an amine moiety of BUx;
provided that $(c+d) \leq (2^x)b$ and d is $\geq 1$; and
provided that if $(c+d) < (2^x)b$, then any remaining W and Z groups are $(H)_e$, wherein e is $[(2^x)b]-(c+d)$.

In some embodiments, the disclosed is a dendrimer of formula (II):

$$\text{Core} \left\{ \left[ (BU1) - (BU2) - (BU3) - (BU4) - (BU5) \right] \underset{Z}{\overset{W,}{\rightleftarrows}} \right\}_b$$

(II)

or a pharmaceutically acceptable salt thereof, wherein
b is 2;
Core is

* indicates covalent attachment to a carbonyl moiety of (BU1);
BU are building units and the number of BU is equal to 62; wherein BU has the following structure:

\# indicates covalent attachment to an amine moiety of Core or an amino moiety of BU, and + indicates a covalent attachment to a carbonyl moiety of BU or a covalent attachment to W or Z;

W is independently $(PM)_c$ or $(H)_e$;
Z is independently $(L-AA)_d$ or $(H)_e$;
PM is $PEG_{900-1200}$ or $PEG_{1800-2400}$;
L-AA is a linker covalently attached to an active agent; wherein L-AA is of the formula:

wherein
A is —N(CH₃), —O—, —S— or —CH₂—;
⊕ indicates covalent attachment to an amine moiety of BU5;
provided that (c+d) is $\leq 64$ and d is $\geq 1$; and
provided that if (c+d)<64, then any remaining W and Z groups are $(H)_e$, wherein e is 64-(c+d).

In some embodiments, disclosed is a dendrimer of formula (III):

D-Core-D    (III)

or a pharmaceutically acceptable salt thereof, wherein
Core is

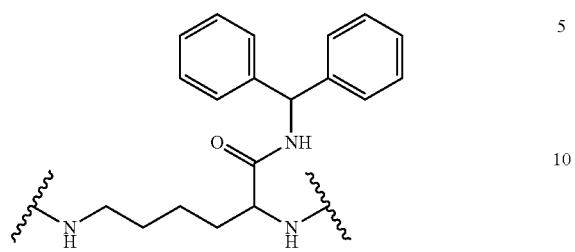

D is

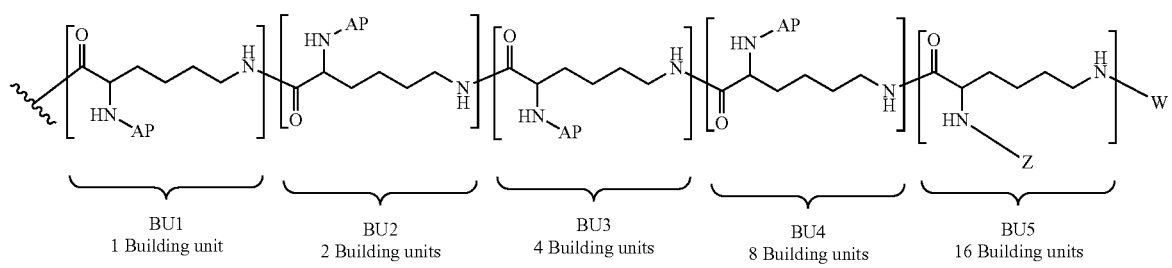

AP is an attachment point to another building unit;
W is independently $(PM)_c$ or $(H)_e$;
Z is independently $(L\text{-}AA)_d$ or $(H)_e$;
PM is $PEG_{900-1200}$ or $PEG_{1800-2400}$;
L-AA is a linker covalently attached to an active agent; wherein L-AA is of the formula:

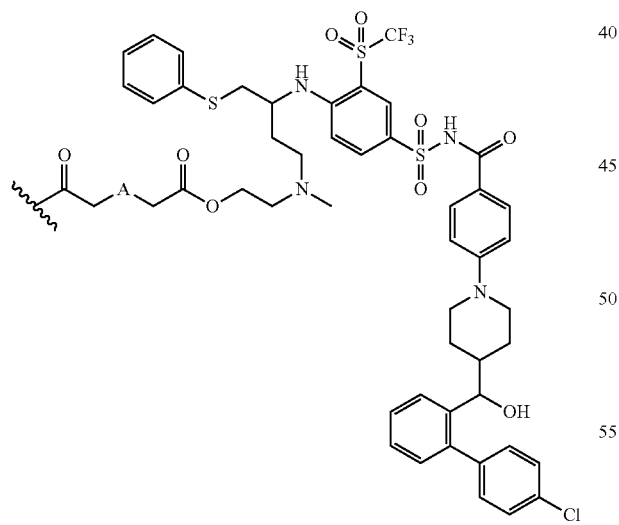

wherein
A is —N(CH$_3$), —O—, —S— or —CH$_2$—;
provided that if $(c+d) \leq 64$, then any remaining W and Z groups are $(H)_e$, wherein e is $64-(c+d)$; and d is $\geq 1$.

In some embodiments, disclosed is a dendrimer of formula (IV):

(IV)
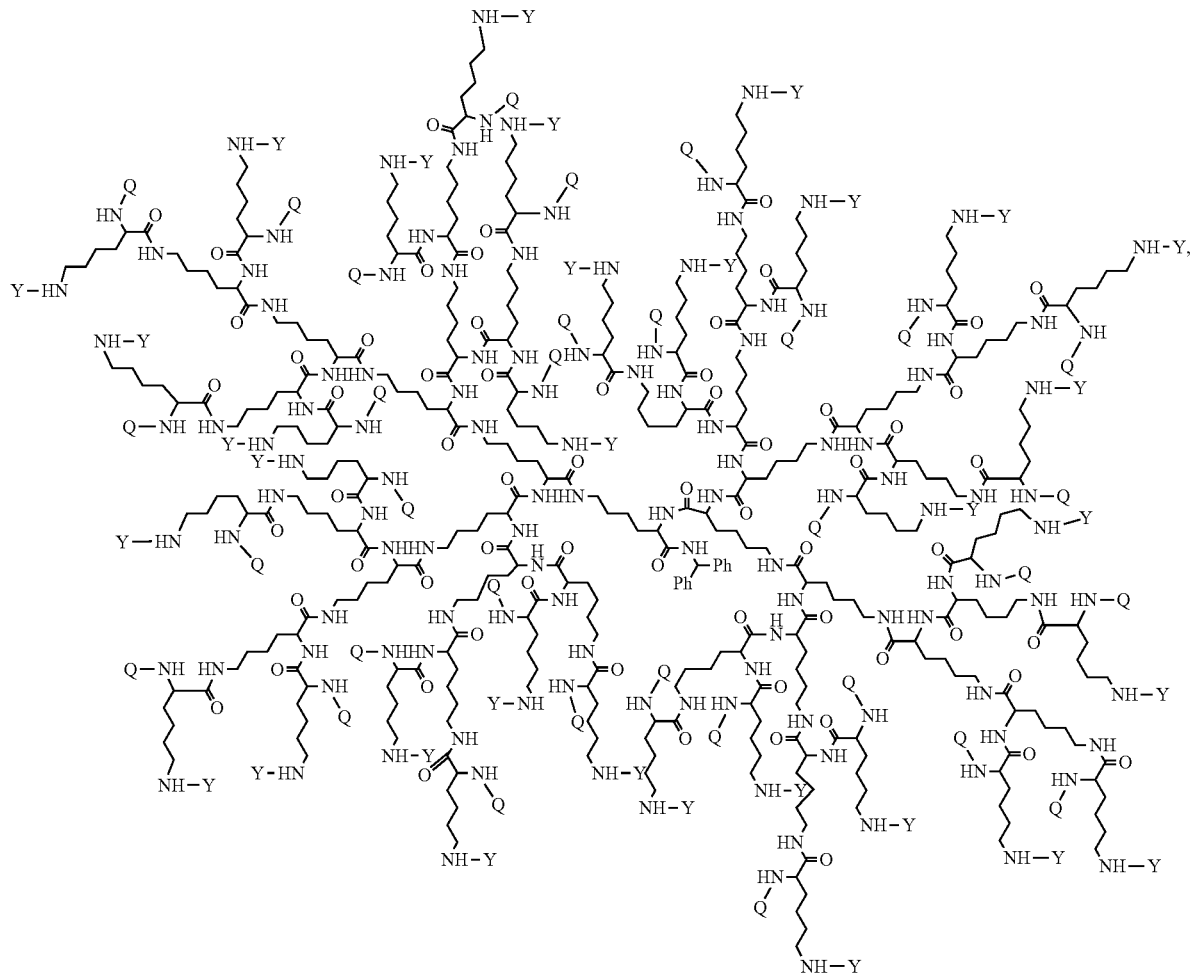
or a pharmaceutically acceptable salt thereof, wherein Y is $PEG_{1800-2400}$ or H; Q is H or L-AA, in which L-AA has the structure:
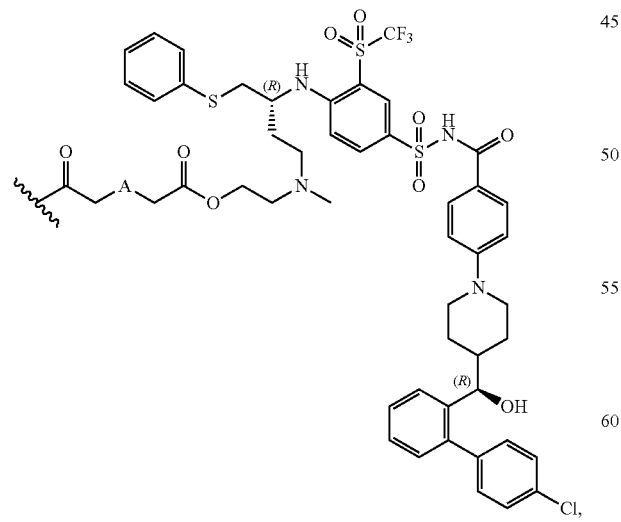
A is —S— or —N(CH$_3$), provided that if the sum of $PEG_{1800-2400}$ and L-AA is less than 64, the remaining Q and Y moieties are H, and provided that at least one Q is L-AA.

In some embodiments, disclosed is a dendrimer of formula (V):

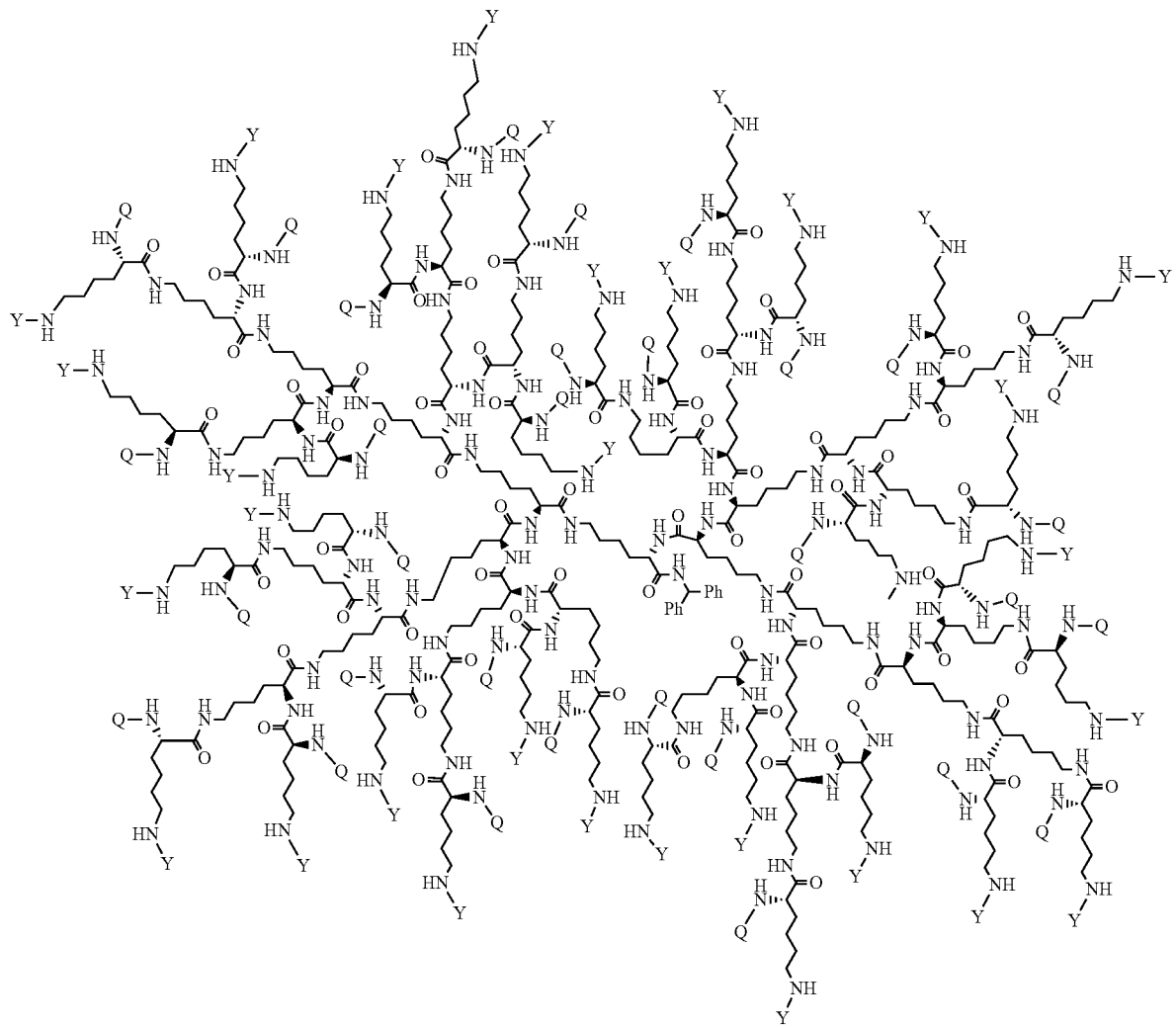

(V)

or a pharmaceutically acceptable salt thereof, wherein Y is PEG$_{1800-2400}$ or H; Q is H or L-AA, in which L-AA has the structure:

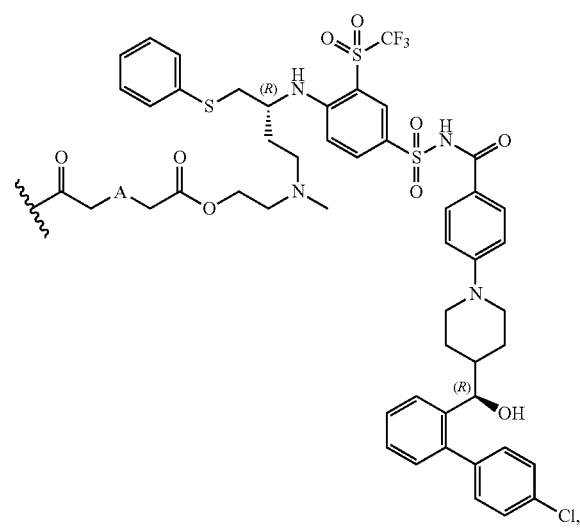

A is —S— or —N(CH$_3$), provided that if the sum of PEG$_{1800-2400}$ and L-AA is less than 64, the remaining Q and Y moieties are H, and provided that at least one Q is L-AA.

In some embodiments, disclosed are pharmaceutical compositions comprising a dendrimer of formula (I), (II), (III), (IV) or (V), or a pharmaceutically acceptable salt thereof, and a pharmaceutically acceptable excipient, carrier or diluent.

In some embodiments, disclosed are methods of treating cancer comprising administering to a subject in need thereof an effective amount of a dendrimer of formula (I), (II), (III), (IV) or (V), or a pharmaceutically acceptable salt thereof.

In some embodiments, disclosed is a dendrimer of formula (I), (II), (III), (IV) or (V), or a pharmaceutically acceptable salt thereof, for use in treating cancer.

In some embodiments, disclosed is the use of a dendrimer of formula (I), (II), (III), (IV) or (V), or a pharmaceutically acceptable salt thereof, for use in the manufacture of a medicament for treating cancer.

In some embodiments, disclosed is a pharmaceutical composition comprising a dendrimer of formula (I), (II), (III), (IV) or (V), or a pharmaceutically acceptable salt thereof, for treating cancer.

BRIEF DESCRIPTION OF THE DRAWINGS

FIG. 3A displays an Acute Lymphoblastic Leukemia (ALL) Xenograft model in SCID mice using human acute lymphoblastic leukemia cells (RS4:11) for formulations of Compound A outlined in Example 2. The efficacy evaluation of Compound A formulated with each of HP-β-CD (V1), Captisol (V2) and Tween (V3) compared to the corresponding vehicles; Vehicle 1 (V1, 30% HP-β-CD, pH4), Vehicle 2 (V2, 10.6% Captisol, pH 9) and Vehicle 3 (V3, 0.5% Tween, pH 9) is shown.

DETAILED DESCRIPTION

In one embodiment, disclosed are dendrimers comprising a divalent benzyhydrylhexanamide-lysine core, lysine building units and wherein the surface functional groups are substituted with a Bcl inhibitor and PEG.

In one embodiment, disclosed are dendrimers of formula (I):

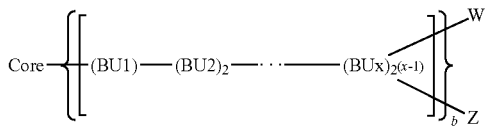

or a pharmaceutically acceptable salt thereof, wherein:
Core is

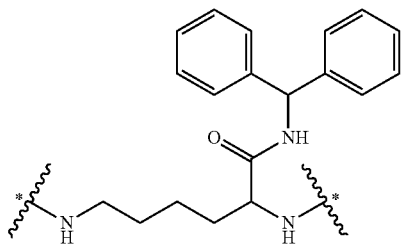 [SMILES: *NCCCCC(N*)C(=O)NC(c1ccccc1)c1ccccc1]

* indicates covalent attachment to a carbonyl moiety of (BU1);
b is 2;
BU are building units;
$BU_x$ are building units of generation x, wherein the total number of building units in generation x of the dendrimer of formula (I) is equal to $2^x$ and the total number of BU in the dendrimer of formula (I) is equal to $(2^x-1)b$; wherein BU has the following structure:

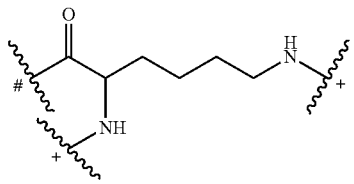

# indicates covalent attachment to an amine moiety of Core or an amino moiety of BU;
+ indicates a covalent attachment to a carbonyl moiety of BU or a covalent attachment to W or Z;
W is independently $(PM)_c$ or $(H)_e$;
Z is independently $(L-AA)_d$ or $(H)_e$;
PM is $PEG_{900-1200}$ or $PEG_{1800-2400}$;
L-AA is a linker covalently attached to an active agent; wherein L-AA is of the formula:

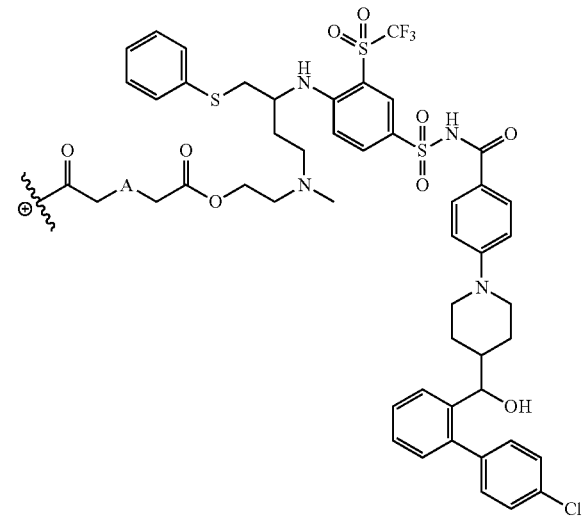

wherein
A is —N(CH₃), —O—, —S— or —CH₂—;
⊕ is the attachment point to an amine moiety of BUx;
provided that $(c+d) \leq (2^x)b$ and d is $\geq 1$; and
provided that if $(c+d) < (2^x)b$, then any remaining W and Z groups are $(H)_e$, wherein e is $[(2^{(x)})b]-(c+d)$.

Figure 1:
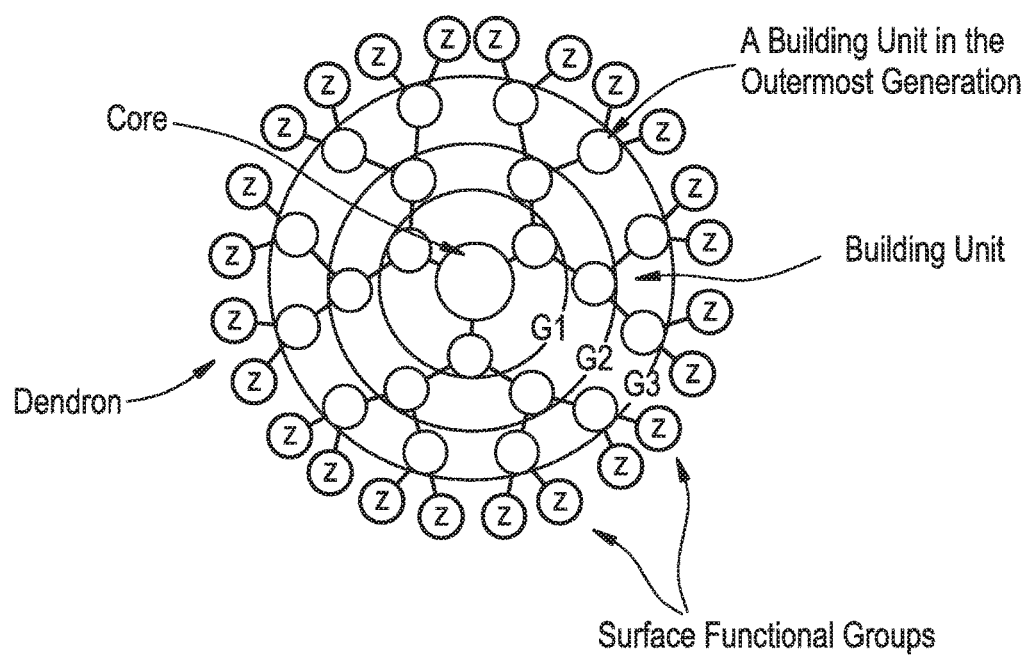
FIG. 1 is a representation of a 3rd generation dendrimer.

For illustration purposes only, FIG. 1 is a representation of a 3rd generation dendrimer, comprising a core, 3 generations of building units (BU) and 24 surface functional groups.

It will be appreciated that the core of the dendrimer represents the central unit from which the dendrimer is built. In this regard, the core represents the central unit from which the first and subsequent generations of building units are 'grown off'. In one embodiment, the Core in any of the dendrimers of formula (I), (II), (III), (IV) or (V) is

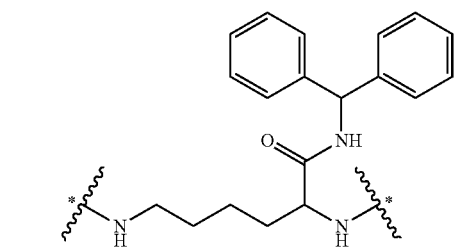 [SMILES: *NCCCCC(N*)C(=O)NC(c1ccccc1)c1ccccc1]

wherein * indicates a covalent attachment to the building units of the dendrimer. In some embodiments, Core in any of the dendrimers of formula (I), (II), (III), (IV) or (V) is

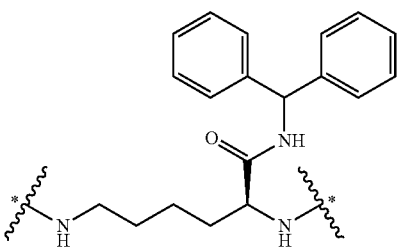 [SMILES: *NCCCC[C@H](N*)C(=O)NC(c1ccccc1)c1ccccc1]

wherein * indicates a covalent attachment to the building units of the dendrimer.

The term "building unit" or "BU" includes molecules having at least three functional groups, one for attachment to the core or a building unit in a previous generation (or layer) of building units and two or more functional groups for attachment to building units in the next generation (or layer) of building units. The building units are used to build the dendrimer layers, by addition to the core or previous layer of building units. In some embodiments the building units have three functional groups.

The term "generation" includes the number of layers of building units that make up a dendron or dendrimer. For example, a one generation dendrimer will have one layer of building units attached to the core, for example, Core-[[building unit]b, where b is the number of dendrons attached to the core and the valency of the core. A two generation dendrimer has two layers of building units in each dendron attached to the core. For example, when the building unit has one bivalent branch point, the dendrimer may be: Core[[building unit][building unit]2]b, a three generation dendrimer has three layers of building units in each dendron attached to the core, for example Core-[[building unit][building unit]2[building unit]4]b, a five generation dendrimer has five layers of building units in each dendron attached to the core, for example, Core-[[building unit][building unit]2[building unit]4[building unit]8[building unit]16]b, a 6 generation dendrimer has six layers of building units attached to the core, for example, Core-[[building unit][building unit]2[building unit]4[building unit]8[building unit]16[building unit]32]b, and the like. The last generation of building units (the outermost generation) provides the surface functionalization of the dendrimer and the number of surface functional groups available for binding the pharmacokinetic modifying group (PM) and/or linker and active agent (L-AA).

The term "surface functional groups" refers to the unreacted functional groups that are found in the final generation of the building units. In some embodiments, the number of surface functional groups are equal to $(2^x)b$, in which x is the number of generations in the dendrimer and b is the number of dendrons. In some embodiments, the surface functional groups are primary amino functional groups.

The total number of building units in a dendrimer with building units having 3 functional groups (e.g., one branch point) is equal to $(2^x-1)b$, where x is equal to the generation number and b is equal to the number of dendrons. For example, in a dendrimer having a core with two dendrons attached (b=2), if each building unit has one branch point and there are 5 generations, there will be 62 building units and the outermost generation will have 16 building units with 64 surface functional groups. In some embodiments, the surface functional groups are amino moieties, for example, primary or secondary amines. In some embodiments, the dendrimer is a fifth generation dendrimer having a bivalent Core, 62 building units and 64 primary amino functional groups.

In some embodiments, the building units in any of the dendrimers of formula (I), (II), (III), (IV) or (V) have the structure:

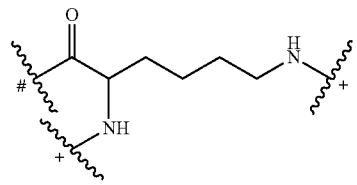 [SMILES: *NCCCC[C@H](N*)C(*)=O]

in which # indicates covalent attachment to an amine moiety of Core or an amino moiety of a building unit, and + indicates a covalent attachment to a carbonyl moiety of a building unit, or covalent attachment to a pharmacokinetic modifying group, a linker attached to an active agent or a hydrogen. In some embodiments, the dendrimer has 62 building units with 64 primary amino functional groups.

In some embodiments, the building units in any of the dendrimers of formula (I), (II), (III), (IV) or (V) have the structure:

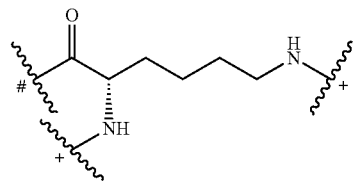

in which # indicates covalent attachment to an amine moiety of Core or an amino moiety of a building unit, and + indicates a covalent attachment to a carbonyl moiety of a building unit, or covalent attachment to a pharmacokinetic modifying group, a linker attached to an active agent or a hydrogen.

The term "pharmacokinetic modifying group" or "PM" includes moieties that may modify or modulate the pharmacokinetic profile of the dendrimer or the active agent it's delivering. In some embodiments, the PM may modulate the distribution, metabolism and/or excretion of the dendrimer or the active agent. In some embodiments, the PM may influence the release rate of the active agent, either by slowing or increasing the rate by which the active agent is released from the dendrimer by either chemical (e.g., hydrolysis) or enzymatic degradation pathways. In some embodiments, the PM may change the solubility profile of the dendrimer, either increasing or decreasing the solubility in a pharmaceutically acceptable carrier. In some embodiments, the PM may assist the dendrimer in delivering the active agent to specific tissues (e.g., tumors).

In some embodiments, in any of the dendrimers of formula (I), (II), (III), (IV) and (V), the PM is polyethylene glycol (PEG). In some embodiments, the polyethylene glycol (PEG) has an average molecular weight of between about 220 and about 5500 Da. In some embodiments, the PEG has an average molecular weight of between about 500 and about 5000 Da. In some embodiments, the PEG has an average molecular weight of between about 1000 and 2500 Da. In some embodiments, the PEG has an average molecular weight of between about 1500 and about 2400 Da. In some embodiments, the PEG has a molecular weight between about 900 and about 1200 Da. In some embodiments the PEG has a molecular weight between about 1800 and about 2400 Da. In some embodiments, the PEG has an average molecular weight of about 2150. One of skill in the art would readily understand that the term "PEG$_{900-1200}$"

includes PEG with an average molecular weight of between about 900 and about 1200 Da and that the term "PEG$_{1800-2400}$" includes PEG with an average molecular weight of between about 1800 and about 2400 Da.

In some embodiments, the PEG has a polydispersity index (PDI) of between about 1.00 and about 2.00, between about 1.00 and 1.50, for example between about 1.00 and about 1.25, between about 1.00 and about 1.10 or between about 1.00 and about 1.10. In some embodiments, the PDI of the PEG is about 1.05. The term "polydispersity index" refers to a measure of the distribution of molecular mass in a given polymer sample. The PDI is equal to is the weight average molecular weight ($M_w$) divided by the number average molecular weight ($M_n$) and indicates the distribution of individual molecular masses in a batch of polymers. The PDI has a value equal to or greater than 1, but as the polymer approaches uniform chain length and average molecular weight, the PD1 will be closer to 1.

In some embodiments, the dendrimer has less than ($2^x$)b PEG groups, wherein x is the number of generations of the dendrimer and b is the number of dendrons. In some embodiments, all of the surface functional groups are covalently attached to PEG groups. In some embodiments, when x is 5, the dendrimer has between about 25 and about 60 PEG groups. In some embodiments, the dendrimer has no more than $2^x$ PEG groups. In some embodiments, the dendrimer has $2^x$ PEG groups. For example, when the building unit of the dendrimer has one bivalent branch point, a second generation dendrimer would have no more than 4 PEG groups, a third generation dendrimer would have no more than 8 PEG groups, a fourth generation dendrimer would have no more than 16 PEG groups, a fifth generation dendrimer would have no more than 32 PEG groups. In some embodiments, dendrimer has less than $2^x$ PEG groups. In some embodiments, the dendrimer has between about 25 and about 64 PEG groups. In some embodiments, the dendrimer has between about 25 and about 40 PEG groups. In some embodiments, the dendrimer has no more than 32 PEG groups. In some embodiments, the dendrimer has between about 25 and about 32 PEG groups. In some embodiments, the dendrimer has about 28 and about 32 PEG groups. In some embodiments, the dendrimer has 29 PEG groups, 30 PEG groups 31 PEG groups or 32 PEG groups.

The disclosed dendrimers of formula (I), (II), (III), (IV) and (V) include a linker covalently attached to an active agent (L-AA), in which the linker (L) is covalently attached to the surface functional groups on the final generation of the building units on one end of the linker and to an active agent (AA) on the other end of the linker. In some embodiments, the linker in any of the dendrimers of formula (I), (II), (III), (IV) or (V) has the structure:

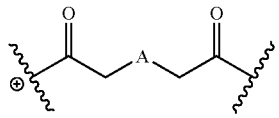

in which ⊕ is covalently attached to the amino functional groups on the final generation of the building units,

is a covalent attachment point to the active agent (AA), and A is —N(CH$_3$), —O—, —S— or —CH$_2$—. In some embodiments, A is —CH$_2$—. In some embodiments, A is —O—. In some embodiments, A is —S—. In some embodiments, A is —N(CH$_3$).

In some embodiments, AA is a Bcl inhibitor. In some embodiments, AA is a Bcl-2 and/or Bcl-XL inhibitor. In some embodiments, AA is a Bcl-2 and/or Bcl-XL inhibitor disclosed in U.S. Pat. No. 9,018,381. In some embodiments, AA in any of the dendrimers of formula (I), (II), (III), (IV) or (V), has the structure:

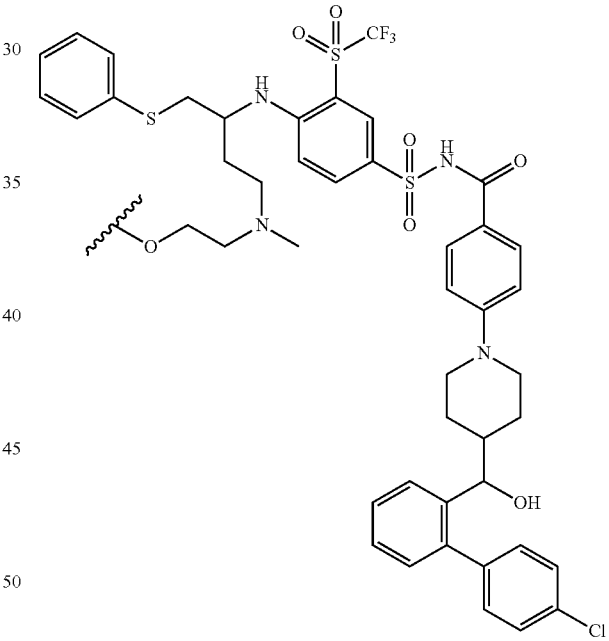

in which

is a covalent attachment point to the linker. In some embodiments, AA in any the dendrimers of formula (I), (II), (III), (IV) or (V) has the structure:

In some embodiments, the structure of L-AA in any of the dendrimers of (I), (II), (III), (IV) or (V) is:

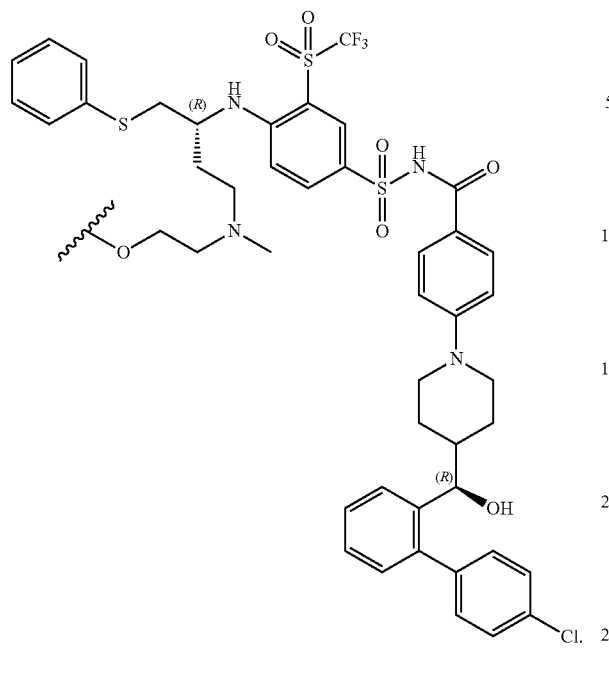

in which ⊕ is covalently attached to the amino functional groups on the final generation of the building units, and A is —N(CH$_3$), —O—, —S— or —CH$_2$—. In some embodiments, A is —CH$_2$—. In some embodiments, A is —O—. In some embodiments, A is —S—. In some embodiments, A is —N(CH$_3$).

In embodiments, the structure of L-AA in any of the dendrimers of formula (I), (II), (III), (IV) or (V) is:

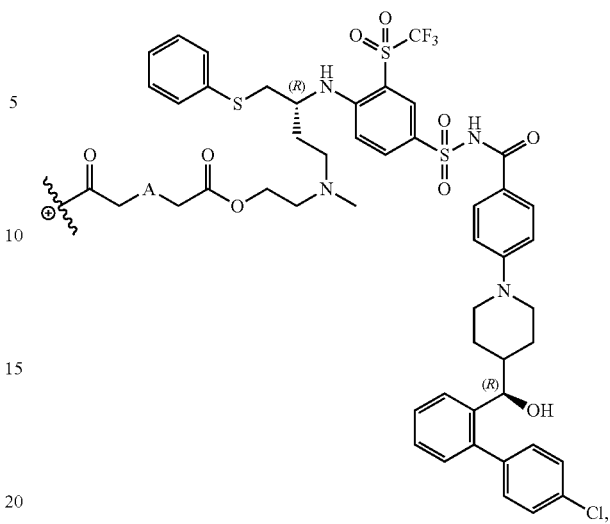

in which ⊕ is covalently attached to the amino functional groups on the final generation of the building units, and A is —N(CH$_3$), —O—, —S— or —CH$_2$—. In some embodiments, A is —CH$_2$—. In some embodiments, A is —O—. In some embodiments, A is —S—. In some embodiments, A is —N(CH$_3$).

In some embodiments, the dendrimer of any one of formula (I), (II), (III), (IV) and (V) has less than $(2^x)b$ L-AA groups, wherein x is the number of generations of the dendrimer and b is the number of dendrons. In some embodiments, all of the surface functional groups are covalently attached to L-AA groups. In some embodiments, when x is 5, the dendrimer has between about 25 and about 64 L-AA groups. In some embodiments, the dendrimer has no more than $2^x$ L-AA groups. In some embodiments, the dendrimer has $2^x$ L-AA groups. For example, when the building unit of the dendrimer has one bifunctional branch point, a second generation dendrimer would have no more than 4 L-AA groups, a third generation dendrimer would have no more than 8 L-AA groups, a fourth generation dendrimer would have no more than 16 L-AA groups, a fifth generation dendrimer would have no more than 32 L-AA groups. In some embodiments, dendrimer has less than $2^x$ L-AA groups. In some embodiments, the dendrimer has between about 25 and about 64 L-AA groups. In some embodiments, the dendrimer has between about 25 and about 40 L-AA groups. In some embodiments, the dendrimer has no more than 32 L-AA groups. In some embodiments, the dendrimer has between about 25 and about 32 L-AA groups. In some embodiments, the dendrimer has between about 28 and about 32 L-AA groups. In some embodiments, the dendrimer has 29 L-AA groups, 30 L-AA groups, 31 L-AA groups or 32 L-AA groups.

In some embodiments, in any of the dendrimers of formula (I), (II), (III), (IV) and (V), the sum of L-AA groups and PEG groups may equal no more than 64. In some embodiments, the sum of L-AA groups and PEG groups may be less than 64, provided that the dendrimer has at least one L-AA group. In some embodiments, the sum of L-AA groups and PEG groups may be between about 50 and about 64. In the event that the sum of the L-AA groups and PEG groups is less than 64, the unreacted surface functional units of the final generation of building units remain primary amino groups, provided that the dendrimer has at least one L-AA group. For example, the number of primary amino groups on the final generation of building units is equal to 64 less the sum of the L-AA and PEG groups (e.g., 64-(L-AA+PEG), provided that the dendrimer has at least one L-AA group. For example, if the sum of the L-AA groups and PEG groups is 50, then 14 surface functional groups will remain primary amino moieties, if the sum of the L-AA groups and PEG groups is 51, 13 of the surface functional groups will remain primary amino moieties, if the sum of the L-AA groups and PEG groups is 52, then 12 of the surface functional groups will remain primary amino moieties, if the sum of the L-AA groups and PEG groups is 53, then 11 of the surface functional groups will remain primary amino moieties, etc. In some embodiments, the number of primary amino moieties on the dendrimer is between about 0 and about 14. In some embodiments, if the sum of the number of PEG groups and the number of L-AA groups is less that $(2^x)b$, in which x is the number of generations of the dendrimer and b is the number of dendrons, then the remaining surface functional groups are equal to 64 less the sum of the PEG groups and the L-AA groups, provided that the dendrimer has at least one L-AA group.

In some embodiments, is W is $(PM)_c$ or $(H)_e$; Z is $(L-AA)_d$ or $(H)_e$; provided that $(c+d) \leq (2^x)b$ and provided that d is $\geq 1$; wherein x is the number of generations and b is the number of dendrons; and provided that if $(c+d)<(2^x)b$, then any remaining W and Z groups are $(H)_e$, wherein e is $[2^{(x+1)}]-(c+d)$. For example, when b is 2 and x is 5, then $(c+d) \leq 64$. In some embodiments, $(c+d)=64$; that is, the sum of $(PM)_c$ and $(L-AA)_d$ is equal to 64. In some embodiments, when b is 2 and x is 5, then $(c+d)<64$; that is the sum of $(PM)_c$ and $(L-AA)_d$ is less than 64, provided that d is $\geq 1$. In some embodiments, $(c+d)$ is an integer between 50 and 64. In some embodiments, $(c+d)$ is an integer between 58 and 64.

In some embodiments, $(c+d)=(2^x)b$ in which case there are no (H), and e is 0. For example, if b is 2 and x is 5, and the sum of $(PM)_c$ and $(L-AA)_d$ is equal to 64, then there are no unsubstituted surface functional groups on the fifth generation of building units in the dendrimer, and therefore e is 0. However, $(c+d)<(2^x)b$, then (H), is equal to $(2^x)b-(c+d)$. For example, if b is 2, x is 5 and the sum of $(PM)_c$ and $(L-AA)_d$ is less than 64, then the number of unsubstituted surface functional groups on the fifth generation of building blocks is equal to 64 less than the sum of $(PM)_c$ and $(L-AA)_d$. In this case, e is equal to 64 less than the sum of $(PM)_c$ and $(L-AA)_d$. In some embodiments, when the sum of $(c+d)$ is an integer between 50 and 64, e is an integer between 0 and 14. In some embodiments, when $(c+d)$ is an integer between 58 and 64, e is an integer between 0 and 6. In some embodiments, $(c+d)$ is 58 and e is 6. In some embodiments, $(c+d)$ is 59 and e is 5. In some embodiments, $(c+d)$ is 60 and e is 4. In some embodiments, $(c+d)$ is 61 and e is 3. In some embodiments, $(c+d)$ is 62 and e is 2. In some embodiments, $(c+d)$ is 63 and e is 1. In some embodiments, $(c+d)$ is 60 and e is 0.

In some embodiments, any of the dendrimers of formula (I), (II), (III), (IV) and (V) have a molecular weight of about 90 to about 120 KDa. In some embodiments, the dendrimer has a molecular weight of about 100 and 115 kDa. In some embodiments, the dendrimer has a molecular weight of about 100 to about 110 kDa. In some embodiments, the dendrimer has a molecular weight of about 100 to about 105 kDa. In some embodiments, the molecular weight of the dendrimer is about 100 kDa, about 101 kDa, about 102 kDa, about 103 KDa, about 104 kDa, about 105 kDa, about 106 KDa, about 107 kDa, about 108 kDa, about 109 kDa or about 110 kDa.

In some embodiments, when BU is

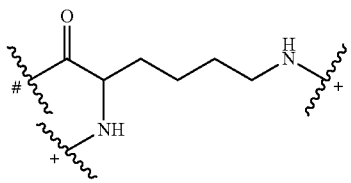 [SMILES: *NCCCCC(N*)C(*)=O]

or

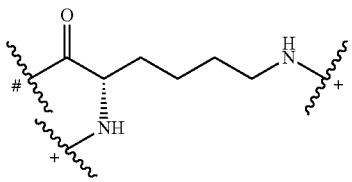 [SMILES: *NCCCC[C@H](N*)C(*)=O]

PEG is covalently attached to the amino functionality at the ε-position of the BU and the L-AA is covalently attached to amino functionality at the α-position of the BU.

In some embodiments, the disclosed is a dendrimer of formula (II):

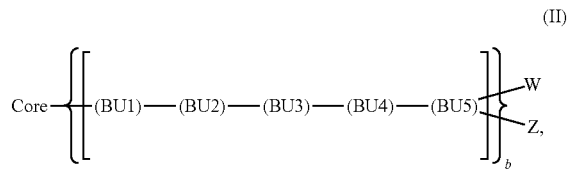

or a pharmaceutically acceptable salt thereof, wherein
b is 2;
Core is

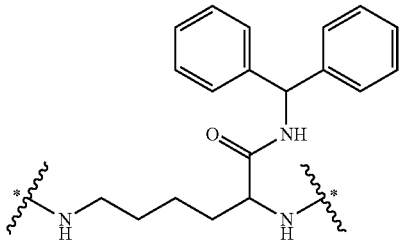 [SMILES: *NCCCCC(N*)C(=O)NC(c1ccccc1)c1ccccc1]

* indicates covalent attachment to a carbonyl moiety of (BU1);
BU are building units and the number of BU is equal to 62; wherein BU has the following structure:

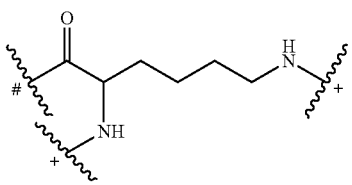 [SMILES: *NCCCCC(N*)C(*)=O]

# indicates covalent attachment to an amine moiety of Core or an amino moiety of BU, and + indicates a covalent attachment to a carbonyl moiety of BU or a covalent attachment to W or Z;

W is independently $(PM)_c$ or $(H)_e$;

Z is independently $(L-AA)_d$ or $(H)_e$;

PM is $PEG_{900-1200}$ or $PEG_{1800-2400}$;

L-AA is a linker covalently attached to an active agent; wherein L-AA is of the formula:

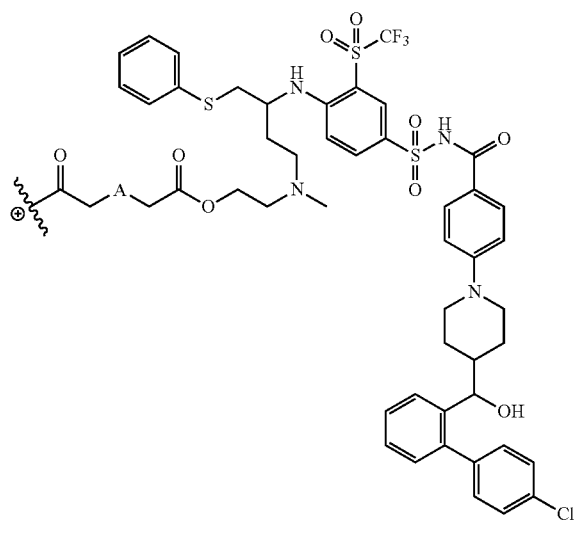

wherein

A is —N(CH$_3$), —O—, —S— or —CH$_2$—;

⊕ indicates covalent attachment to an amine moiety of BUS;

provided that (c+d) is ≤64 and d is ≥1; and provided that if (c+d)<64, then any remaining W and Z groups are $(H)_e$, wherein e is 64-(c+d).

In some embodiments of the dendrimer of formula (II), $(PM)_c$ is $PEG_{900-1200}$ and A is —O—. In some embodiments, $(PM)_c$ is $PEG_{1800-2400}$ and A is —O—. In some embodiments of the dendrimer of formula (II), $(PM)_c$ is $PEG_{1800-2400}$ and A is —N(CH$_3$). In some embodiments of the dendrimer of formula (II), $(PM)_c$ is $PEG_{1800-2400}$ and A is —S—. In some embodiments of the dendrimer of formula (II), $(PM)_c$ is $PEG_{1800-2400}$ and A is —CH$_2$—.

In some embodiments of the dendrimer of formula (II), c is an integer between 25 and 32. In some embodiments of the dendrimer of formula (II), c is an integer between 29 and 32. In some embodiments of the dendrimer of formula (II), c is 29. In some embodiments of the dendrimer of formula (II), c is 30. In some embodiments of the dendrimer of formula (II), c is 31. In some embodiments of the dendrimer of formula (II), c is 32.

In some embodiments of the dendrimer of formula (II), d is an integer between 25 and 32. In some embodiments of the dendrimer of formula (II), d is an integer between 29 and 32. In some embodiments of the dendrimer of formula (II), d is 29. In some embodiments of the dendrimer of formula (II), d is 30. In some embodiments of the dendrimer of formula (II), d is 31. In some embodiments of the dendrimer of formula (II), d is 32.

In some embodiments of the dendrimer of formula (II), e is an integer between 0 and 14. In some embodiments of the dendrimer of formula (II), e is an integer between 0 and 6. In some embodiments of the dendrimer of formula (II), e is 0. In some embodiments of the dendrimer of formula (II), e is 1. In some embodiments of the dendrimer of formula (II), e is 2. In some embodiments of the dendrimer of formula (II), e is 3. In some embodiments of the dendrimer of formula (II), e is 4. In some embodiments of the dendrimer of formula (II), e is 5. In some embodiments of the dendrimer of formula (II), e is 6.

In some embodiments of the dendrimer of formula (II), L-AA is:

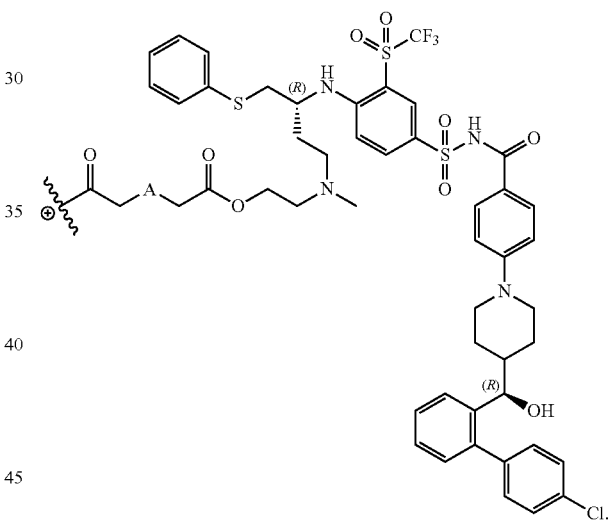

In some embodiments, disclosed is a dendrimer of formula (III):

D-Core-D     (III)

or a pharmaceutically acceptable salt thereof, wherein Core is

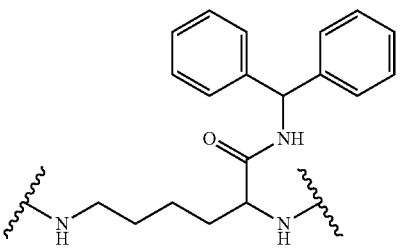 [SMILES: *NCCCCC(N*)C(=O)NC(c1ccccc1)c1ccccc1]

D is

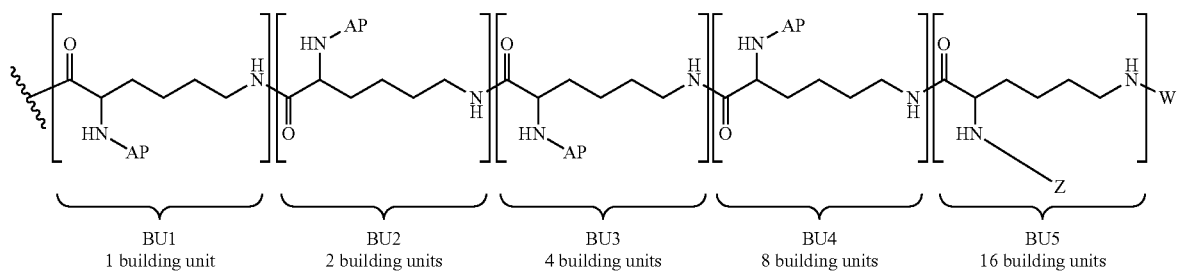

AP is an attachment point to another building unit;
W is independently $(PM)_c$ or $(H)_e$;
Z is independently $(L-AA)_d$ or $(H)_e$;
PM is $PEG_{900-1200}$ or $PEG_{1800-2400}$;
L-AA is a linker covalently attached to an active agent; wherein L-AA is of the formula:

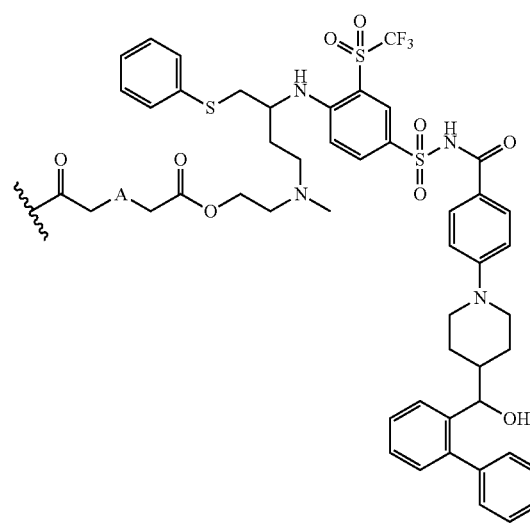

wherein
A is $-N(CH_3)$, $-O-$, $-S-$ or $-CH_2-$;
provided that if $(c+d)<64$, then any remaining W and Z groups are $(H)_e$, wherein $e$ is $64-(c+d)$; and d is $\geq 1$.
In some embodiments, D is In some embodiments of the dendrimer of formula (III), $(PM)_c$ is $PEG_{900-1200}$ and A is $-O-$. In some embodiments of the dendrimer of formula (III), $(PM)_c$ is $PEG_{1800-2400}$ and A is $-O-$. In some embodiments of the dendrimer of formula (III), $(PM)_c$ is $PEG_{1800-2400}$ and A is $-N(CH_3)$. In some embodiments of the dendrimer of formula (III), $(PM)_c$ is $PEG_{1800-2400}$) and A is $-S-$. In some embodiments of the dendrimer of formula (III), $(PM)_c$ is $PEG_{1800-2400}$ and A is $-CH_2-$.

In some embodiments of the dendrimer of formula (III), c is an integer between 25 and 32. In some embodiments of the dendrimer of formula (III), c is an integer between 29 and 32. In some embodiments of the dendrimer of formula (III), c is 29. In some embodiments of the dendrimer of formula (III), c is 30. In some embodiments of the dendrimer of formula (III), c is 31. In some embodiments of the dendrimer of formula (III), c is 32.

In some embodiments of the dendrimer of formula (III), d is an integer between 25 and 32. In some embodiments of the dendrimer of formula (III), d is an integer between 29 and 32. In some embodiments of the dendrimer of formula (III), d is 29. In some embodiments of the dendrimer of formula (III), d is 30. In some embodiments of the dendrimer of formula (III), d is 31. In some embodiments of the dendrimer of formula (III), d is 32.

In some embodiments of the dendrimer of formula (III), e is an integer between 0 and 14. In some embodiments of the dendrimer of formula (III), e is an integer between 0 and 6. In some embodiments of the dendrimer of formula (III), e is 0. In some embodiments of the dendrimer of formula (III), e is 1. In some embodiments of the dendrimer of formula (III), e is 2. In some embodiments of the dendrimer of formula (III), e is 3. In some embodiments of the dendrimer of formula (III), e is 4. In some embodiments of the dendrimer of formula (III), e is 5. In some embodiments of the dendrimer of formula (III), e is 6.

In some embodiments of the dendrimer of formula (III), L-AA of the dendrimer of formula (III) is:

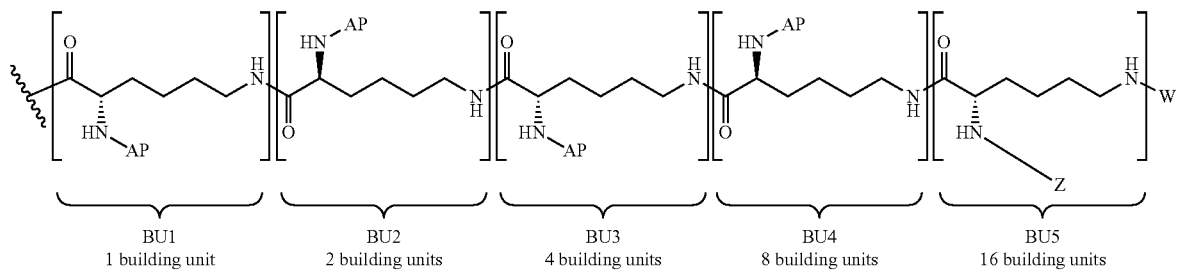

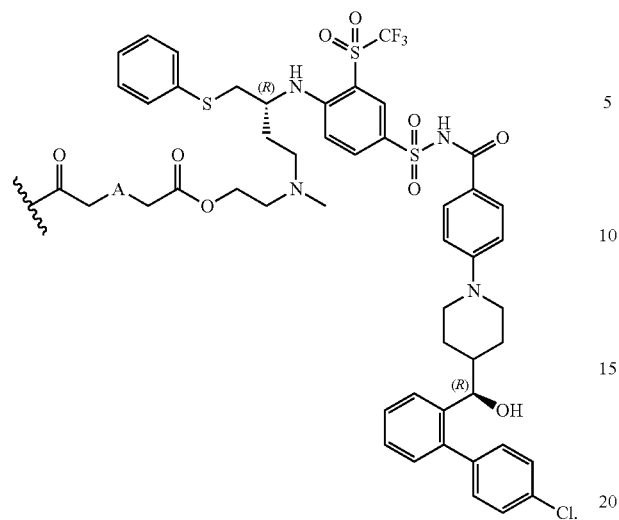
In some embodiments, disclosed is a dendrimer of formula (IV):
(IV)
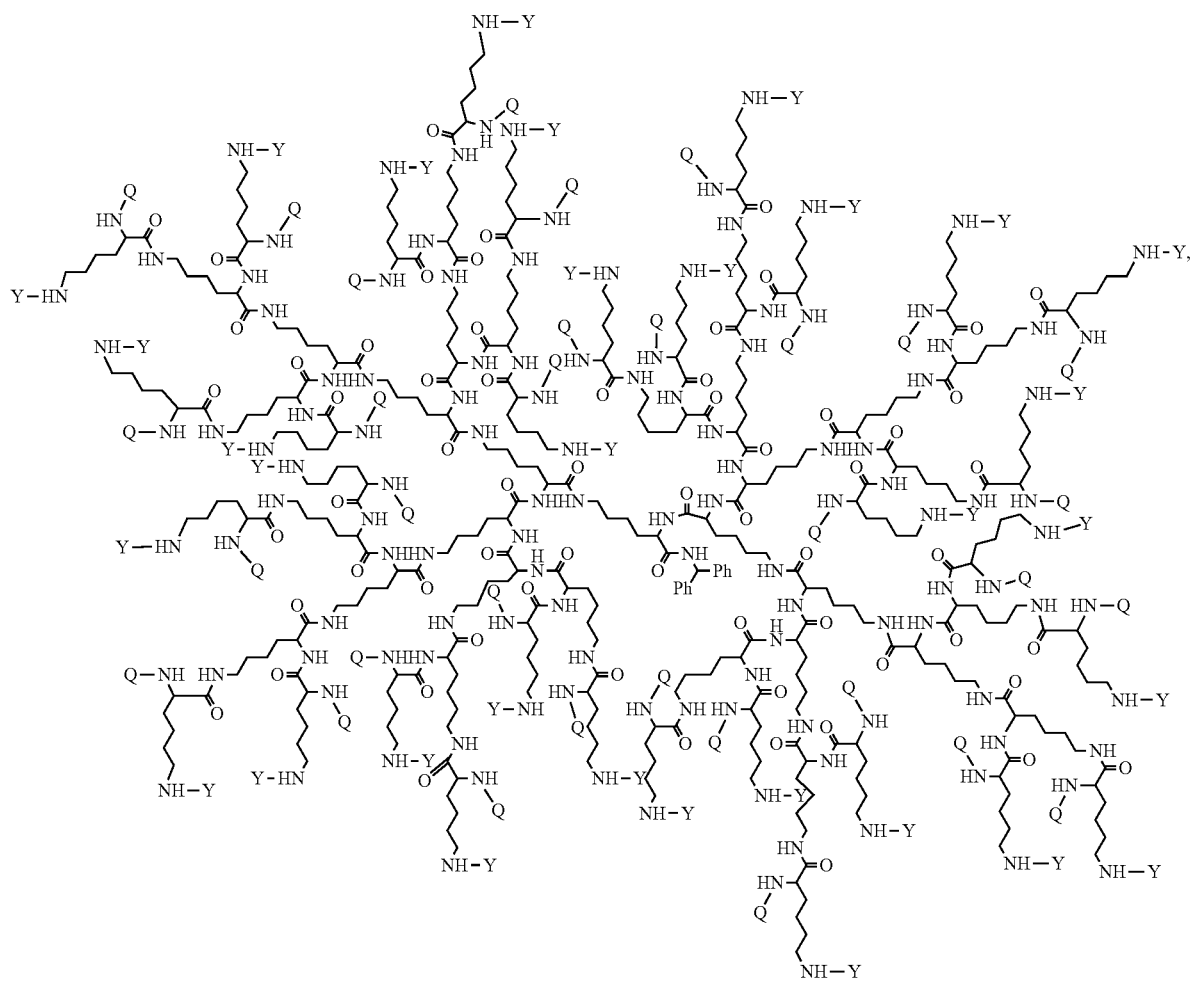
or a pharmaceutically acceptable salt thereof, wherein Y is $PEG_{1800-2400}$ or H; Q is H or L-AA, in which L-AA has the structure:

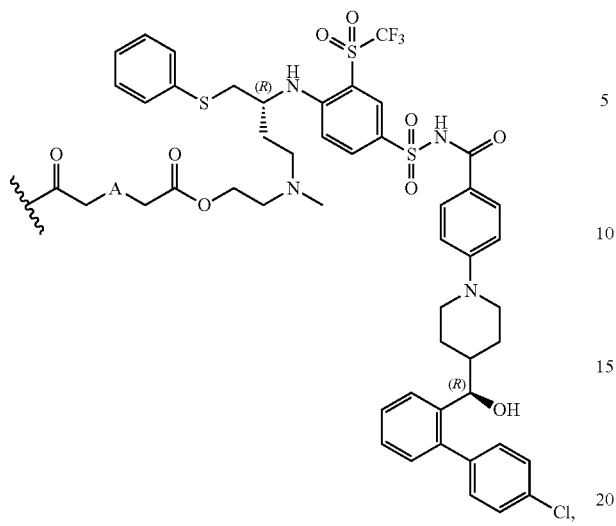

A is —S— or —N(CH$_3$), provided that if the sum of PEG$_{1800\text{-}2400}$ and L-AA is less than 64, the remaining Q and Y moieties are H, and provided that at least one Q is L-AA.

In some embodiments of the dendrimer of formula (IV), A is —N(CH$_3$). In some embodiments, of the dendrimer of formula (IV), A is —S—.

In some embodiments, the dendrimer of formula (IV) has between 25 and 32 PEG$_{1800\text{-}2400}$. In some embodiments, the dendrimer of formula (IV) has between 29 and 32 PEG$_{1800\text{-}2400}$. In some embodiments, the dendrimer of formula (IV) has 29 PEG$_{1800\text{-}2400}$. In some embodiments, the dendrimer of formula (IV) has 30 PEG$_{1800\text{-}2400}$. In some embodiments, the dendrimer of formula (IV) has 31 PEG$_{1800\text{-}2400}$. In some embodiments, the dendrimer of formula (IV) has 32 PEG$_{1800\text{-}2400}$.

In some embodiments, the dendrimer of formula (IV) has between 25 and 32 L-AA. In some embodiments, the dendrimer of formula (IV) has between 29 and 32 L-AA. In some embodiments, the dendrimer of formula (IV) has 29 L-AA. In some embodiments, the dendrimer of formula (IV) has 30 L-AA. In some embodiments, the dendrimer of formula (IV) has 31 L-AA. In some embodiments, the dendrimer of formula (IV) has 32 L-AA.

In some embodiments, the dendrimer of formula (IV) has between 0 and 14 hydrogens at the Q and/or Y positions. In some embodiments, the dendrimer of formula (IV) has between 0 and 6 hydrogens at the Q and/or Y positions. In some embodiments, the dendrimer of formula (IV) has 1 hydrogen at the Q and/or Y positions. In some embodiments, the dendrimer of formula (IV) has 2 hydrogens at the Q and/or Y positions. In some embodiments, the dendrimer of formula (IV) has 3 hydrogens at the Q and/or Y positions. In some embodiments, the dendrimer of formula (IV) has 4 hydrogens at the Q and/or Y positions. In some embodiments, the dendrimer of formula (IV) has 5 hydrogens at the Q and/or Y positions. In some embodiments, the dendrimer of formula (IV) has 6 hydrogens at the Q and/or Y positions.

In some embodiments, disclosed is a dendrimer of formula (V):

(V)

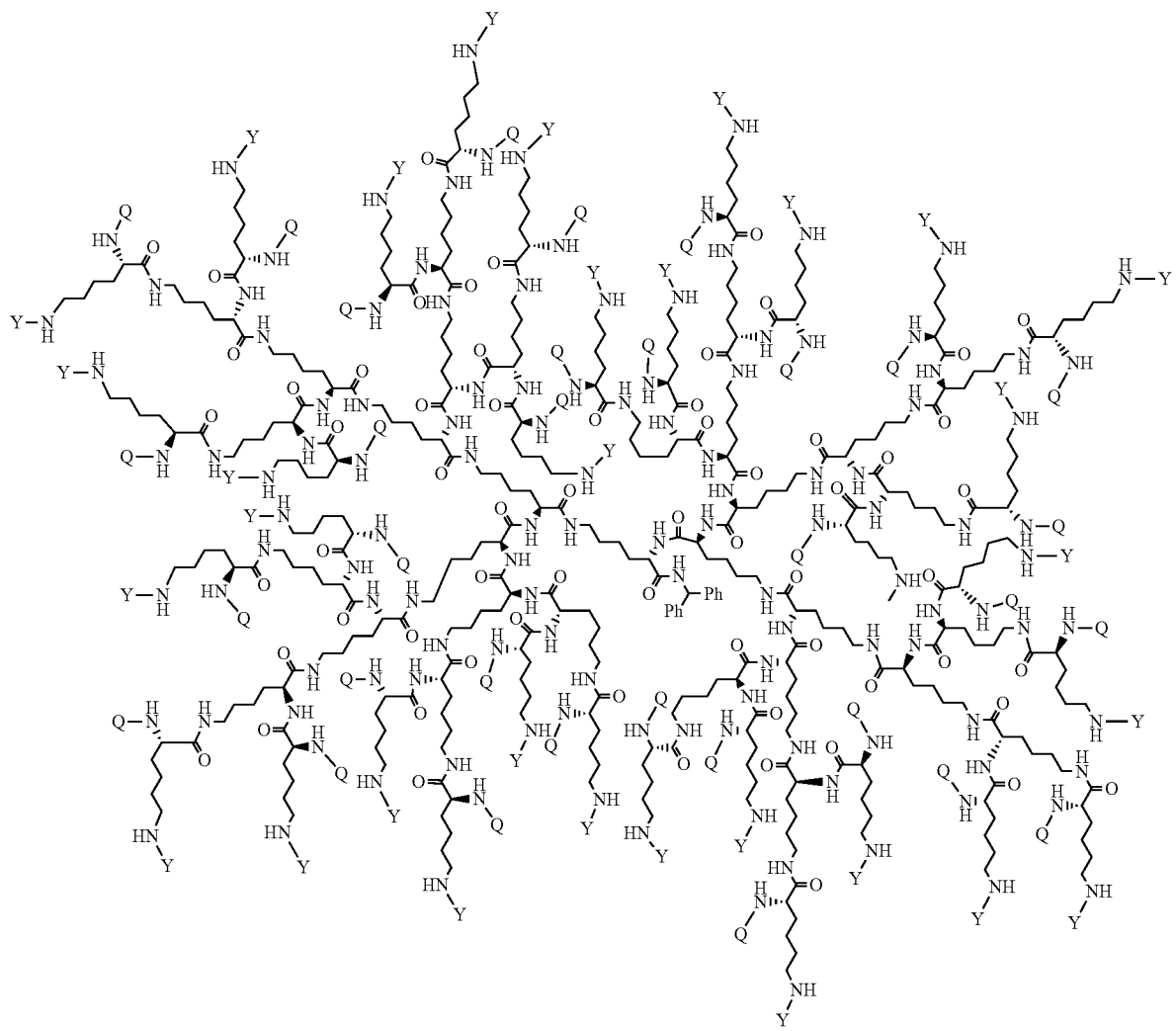

or a pharmaceutically acceptable salt thereof, wherein Y is PEG$_{1800-2400}$ or H; Q is H or L-AA, in which L-AA has the structure:

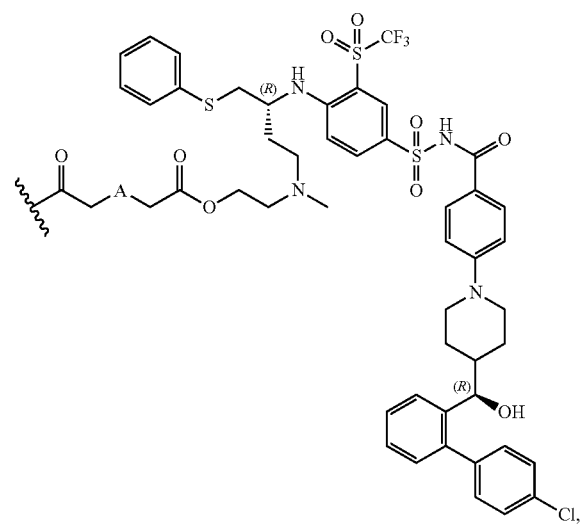

A is —S— or —N(CH$_3$), provided that if the sum of PEG$_{1800-2400}$ and L-AA is less than 64, the remaining Q and Y moieties are H, and provided that at least one Q is L-AA.

In some embodiments of the dendrimer of formula (V), A is —N(CH$_3$). In some embodiments, of the dendrimer of formula (V), A is —S—.

In some embodiments, the dendrimer of formula (V) has between 25 and 32 PEG$_{1800-2400}$. In some embodiments, the dendrimer of formula (V) has between 29 and 32 PEG$_{1800-2400}$. In some embodiments, the dendrimer of formula (V) has 29 PEG$_{1800-2400}$. In some embodiments, the dendrimer of formula (V) has 30 PEG$_{1800-2400}$. In some embodiments, the dendrimer of formula (V) has 31 PEG$_{1800-2400}$. In some embodiments, the dendrimer of formula (V) has 32 PEG$_{1800-2400}$.

In some embodiments, the dendrimer of formula (V) has between 25 and 32 L-AA. In some embodiments, the dendrimer of formula (V) has between 29 and 32 L-AA. In some embodiments, the dendrimer of formula (V) has 29 L-AA. In some embodiments, the dendrimer of formula (V) has 30 L-AA. In some embodiments, the dendrimer of formula (V) has 31 L-AA. In some embodiments, the dendrimer of formula (V) has 32 L-AA.

In some embodiments, the dendrimer of formula (V) has between 0 and 14 hydrogens at the Q and/or Y positions. In some embodiments, the dendrimer of formula (V) has between 0 and 6 hydrogens at the Q and/or Y positions. In some embodiments, the dendrimer of formula (V) has 1 hydrogen at the Q and/or Y positions. In some embodiments, the dendrimer of formula (V) has 2 hydrogens at the Q and/or Y positions. In some embodiments, the dendrimer of formula (V) has 3 hydrogens at the Q and/or Y positions. In some embodiments, the dendrimer of formula (V) has 4 hydrogens at the Q and/or Y positions. In some embodiments, the dendrimer of formula (V) has 5 hydrogens at the Q and/or Y positions. In some embodiments, the dendrimer of formula (V) has 6 hydrogens at the Q and/or Y positions.

In some embodiments, also disclosed are compounds with the structures:

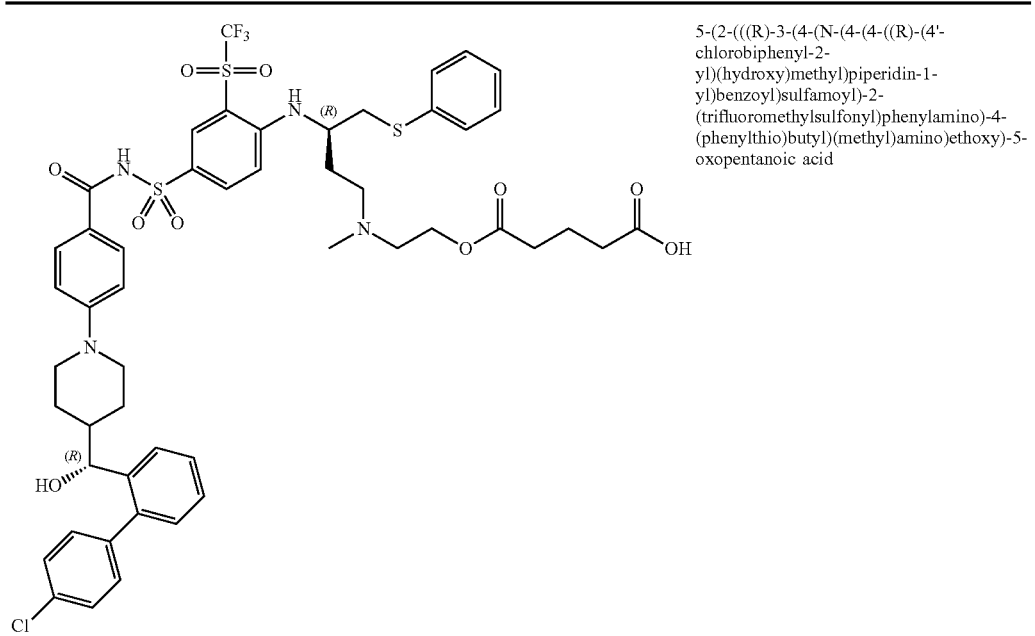

5-(2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethoxy)-5-oxopentanoic acid Glu-Compound A

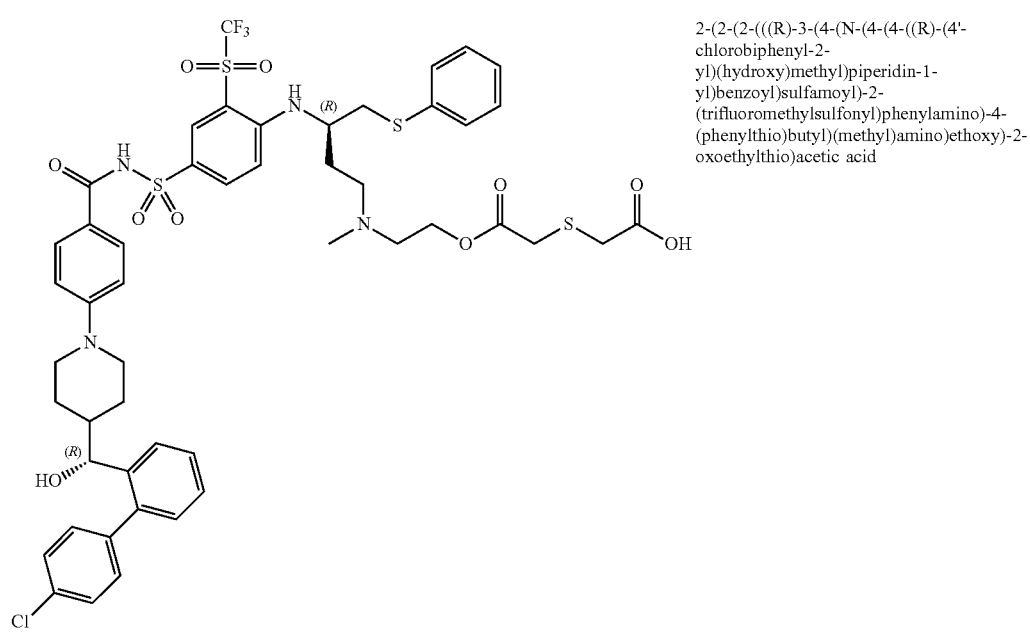

2-(2-(2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethoxy)-2-oxoethylthio)acetic acid TDA-Compound A

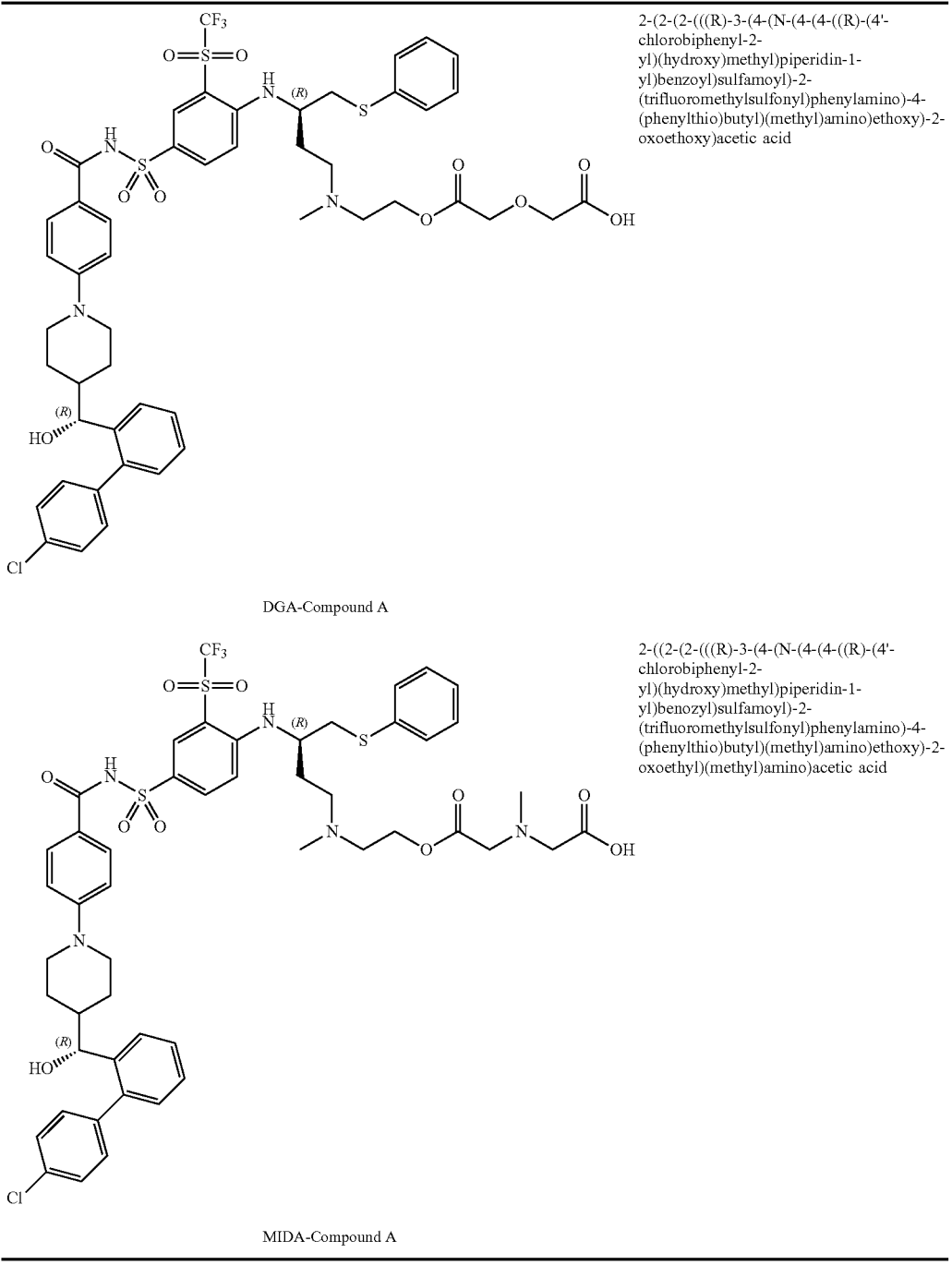

DGA-Compound A 2-(2-(2-(((R)-3-(4-(N-(4-(4-((R)-(4'-chlorobiphenyl-2-yl)(hydroxy)methyl)piperidin-1-yl)benzoyl)sulfamoyl)-2-(trifluoromethylsulfonyl)phenylamino)-4-(phenylthio)butyl)(methyl)amino)ethoxy)-2-oxoethoxy)acetic acid MIDA-Compound A 2-((2-(2-(((R)-3-(4-(N-(4-(4-((R)-(4'-chlorobiphenyl-2-yl)(hydroxy)methyl)piperidin-1-yl)benozyl)sulfamoyl)-2-(trifluoromethylsulfonyl)phenylamino)-4-(phenylthio)butyl)(methyl)amino)ethoxy)-2-oxoethyl)(methyl)amino)acetic acid The language "pharmaceutically acceptable salt" includes acid addition or base salts that retain the biological effectiveness and properties of the dendrimers of formula (I), (II), (III), (IV) and (V), and, which typically are not biologically or otherwise undesirable. In many cases, the dendrimers of formula (I), (II), (III), (IV) and (V) are capable of forming acid and/or base salts by virtue of the presence of basic and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulfate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, sulfate/hydrogensulfate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic acid, sulfosalicylic acid, and the like.

Pharmaceutically acceptable base addition salts can be formed with inorganic and organic bases. Inorganic bases from which salts can be derived include, for example, ammonia and salts of ammonium and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, chlorinate, diethanolamine, diethylamine, lysine, meglumine, piperazine and tromethamine.

The pharmaceutically acceptable salts of the dendrimers of formula (I), (II), (III), (IV) and (V) can be synthesized from a basic or acidic moiety, by conventional chemical methods. Generally, such salts can be prepared by reacting free acid forms of these compounds with a stoichiometric amount of the appropriate base (such as $Na^+$, $Ca^{2+}$, $Mg^{2+}$, or $K^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); Berge et al., "J. Pharm. Sci., 1977, 66, 1-19 and in "Handbook of Pharmaceutical Salts: Properties, Selection, and Use" by Stahl and Wermuth (Wiley-VCH, Weinheim, Germany, 2002).

Any formula given herein may also represent unlabeled forms as well as isotopically labeled forms for the dendrimers of formula (I), (II), (III), (IV) and (V). Isotopically labeled compounds have structures depicted by the formulas given herein except that one or more atoms are replaced by an atom of the same element but with differing mass number. Examples of isotopes that can be incorporated into the dendrimer of formula (I), (II), (III), (IV) and (V) and their salts include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{35}S$ and $^{125}I$. The dendrimers of formula (I), (II), (III), (IV) and (V) may include various isotopically labeled compounds into which radioactive isotopes, such as, $^3H$, $^{11}C$, $^{14}C$, $^{35}S$ and $^{36}Cl$ are present. Isotopically labeled dendrimers of formula (I), (II), (III) and (IV) can generally be prepared by conventional techniques known to those skilled in the art or by processes analogous to those described in the accompanying Examples using appropriate isotopically labeled reagents in place of the non-labeled reagents previously employed.

The dendrimers of formula (I), (II), (III), (IV) and (V) may have different isomeric forms. The language "optical isomer" or "stereoisomer" refers to any of the various stereoisomeric configurations which may exist for a given dendrimer of formula (I), (II), (III), (IV) and (V). In particular, the dendrimers of formula (I), (II), (III), (IV) and (V) possess chirality and as such may exist as mixtures of enantiomers with enantiomeric excess between about 0% and >98% e.e. When a compound is a pure enantiomer, the stereochemistry at each chiral center may be specified by either R or S. Such designations may also be used for mixtures that are enriched in one enantiomer. Resolved compounds whose absolute configuration is unknown can be designated (+) or (−) depending on the direction (dextro- or levorotatory) which they rotate plane polarized light at the wavelength of the sodium D line. The present disclosure is meant to include all such possible isomers, including racemic mixtures, optically pure forms and intermediate mixtures. Optically active (R)- and (S)-isomers may be prepared using chiral synthons, chiral reagents or chiral catalysts, or resolved using conventional techniques well known in the art, such as chiral HPLC.

Pharmaceutical Compositions

In some embodiments, disclosed are pharmaceutical compositions comprising a dendrimer of formula (I), (II), (III), (IV) or (V), or a pharmaceutically acceptable salt thereof, and a pharmaceutically acceptable excipient, carrier or diluent.

The language "pharmaceutically acceptable excipient, carrier or diluent" includes compounds, materials, compositions, and/or dosage forms which are, within the scope of sound medical judgment, suitable for use in contact with the tissues of human beings and animals without excessive toxicity, irritation, allergic response, or other problem or complication, as ascertained by one of skill in the art.

The disclosed compositions may be in a form suitable for oral use (for example, as tablets, lozenges, hard or soft capsules, aqueous or oily suspensions, emulsions, dispersible powders or granules, syrups or elixirs), for topical use (for example, as creams, ointments, gels, or aqueous or oily solutions or suspensions), for administration by inhalation (for example, as a finely divided powder or a liquid aerosol), for administration by insufflation (for example, as a finely divided powder) or for parenteral administration (for example, as a sterile aqueous or oily solution for intravenous, subcutaneous, intramuscular or intramuscular dosing or as a suppository for rectal dosing).

The disclosed compositions may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation may include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil, such as peanut oil, liquid paraffin, or olive oil.

Aqueous suspensions may contain the active ingredient in finely powdered form or in the form of nano or micronized particles together with one or more suspending agents, such as sodium carboxymethylcellulose, methylcellulose, hydroxypropylmethylcellulose, sodium alginate, polyvinylpyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid; coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents and flavoring agents may be added to provide a palatable oral preparation. These compositions may be preserved by the addition of an anti-oxidant such as ascorbic acid.

Dispersible powders and granules suitable for preparation of an aqueous suspension by the addition of water may contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Pharmaceutical compositions may also be in the form of a sterile injectable solution in one or more aqueous or non-aqueous non-toxic parenterally-acceptable buffer systems, diluents, solubilizing agents, co-solvents, or carriers, such as ethanol, Solutol HS15, PEG400, Tween 80, benzyl alcohol, NN-dimethylacetamide, propyleneglycol, Cremophor, HP-β-CD, SBE-β-1865 cyclodextrin. A sterile injectable preparation may also be a sterile injectable aqueous or oily suspension or suspension in a non-aqueous diluent, carrier or co-solvent, which may be formulated according to known procedures using one or more of the appropriate dispersing or wetting agents and suspending agents.

The pharmaceutical compositions could be a solution for iv bolus/infusion injection, sterile dendrimer for reconstitution with a buffer system, or a lyophilized system (either dendrimer alone or with excipients) for reconstitution with a buffer system with or without other excipients. The lyophilized freeze dried material may be prepared from non-aqueous solvents (e.g., t-butanol or acetic acid) or aqueous solvents. The dosage form could also be a concentrate for further dilution for subsequent infusion.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The amount of active ingredient that may be combined with one or more excipients to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The dendrimers of formula (I), (II), (III), (IV) and (V) may be administered once, twice, three times a day or as many times in a 24 hour period as medically necessary. One of skill in the art would readily be able to determine the amount of each individual dose based on the subject. In some embodiments, the dendrimers of formula (I), (II), (III), (IV) and (V) are administered in one dosage form. In some embodiments, the dendrimers of formula (I), (II), (III), (IV) and (V) are administered in multiple dosage forms.

Method of Use

In one aspect, disclosed are methods for treating cancer in a subject in need thereof, comprising administering to the subject an effective amount of a dendrimer of formula (I), (II), (III), (IV) or (V), or a pharmaceutically acceptable salt thereof.

In one aspect, disclosed is a dendrimer of formula (I), (II), (III), (IV) or (V), or a pharmaceutically acceptable salt thereof, for use in treating cancer.

In one aspect, disclosed is the use of a dendrimer of formula (I), (II), (III), (IV) or (V), or a pharmaceutically acceptable salt thereof, in the manufacture of a medicament for treating a cancer.

In one aspect, disclosed are pharmaceutical compositions comprising a dendrimer of formula (I), (II), (III), (IV) or (V), or a pharmaceutically acceptable salt thereof, for use in treating cancer.

The term "cancer" includes, but is not limited to, hematological (e.g., lymphomas, leukemia) and solid malignancies. The term "cancer" includes, for example, T-cell leukemias, T-cell lymphomas, acute lymphoblastic lymphoma (ALL), acute myelogenous leukemia (AML), chronic lymphocytic leukemia (CLL), small lymphocytic lymphoma (SLL), chronic myelogenous leukemia (CML), acute monocytic leukemia (AML), multiple myeloma, mantle cell lymphoma, diffuse large B cell lymphoma (DLBCL), Burkitt's lymphoma, Non-Hodgkin's lymphoma, follicular lymphoma and solid tumors, for example, non-small cell lung cancer (NSCLC, e.g., EGF mutant NSCLC, KRAS mutant NSCLC), small cell lung cancer (SCLC), breast cancer, neuroblastoma, ovarian cancer, prostate cancer, melanoma (e.g., BRAF mutant melanoma, KRAS mutant melanoma), pancreatic cancer, uterine, endometrial and colon cancer (e.g., KRAS mutant colon cancer, BRAF mutant colon cancer).

In one aspect, disclosed are methods for treating cancer in a subject in need thereof comprising administering to the subject an effective amount of a dendrimer of formula (I), (II), (III), (IV) or (V), or a pharmaceutically acceptable salt thereof in combination with an effective amount of a second anti-cancer agent, or a pharmaceutically acceptable salt thereof.

In one aspect, disclosed is a dendrimer of formula (I), (II), (III), (IV) or (V), or a pharmaceutically acceptable salt thereof in combination with an effective amount of a second anti-cancer agent, or a pharmaceutically acceptable salt thereof, for use in treating a cancer.

In one aspect, disclosed is the use of a dendrimer of formula (I), (II), (III), (IV) or (V), or a pharmaceutically acceptable salt thereof, in combination with an effective amount of an anti-cancer agent, or a pharmaceutically acceptable salt thereof, in the manufacture of a medicament for treating cancer.

In one aspect, disclosed are pharmaceutical compositions comprising a dendrimer of formula (I), (II), (III), (IV) or (V), or a pharmaceutically acceptable salt thereof, in combination with an effective amount of a second anti-cancer agent, or a pharmaceutically acceptable salt thereof, for use in treating cancer.

The language "in combination with" includes administering the dendrimer of formula (I), (II), (III), (IV) or (V), or a pharmaceutically acceptable salt thereof, and the anti-cancer agent, or pharmaceutically acceptable salt thereof, sequentially, separately or simultaneously. In some aspects, the dendrimer of formula (I), (II), (III), (IV) or (V), or a pharmaceutically acceptable salt thereof, and the second anti-cancer agent, or pharmaceutically acceptable salt thereof, may be administered in the same formulation, for example, in a fixed dose formulation. In some embodiments, the dendrimer of formula (I), (II), (III), (IV) or (V), or a pharmaceutically acceptable salt thereof, and the second anti-cancer agent, or pharmaceutically acceptable salt thereof, may be administered in separate formulations, and are administered at substantially the same time, sequentially or separately.

The language "anti-cancer agent" includes, but is not limited to, radiation, alkylating agents, angiogenesis inhibitors, antibodies, antibody-drug conjugates, antimetabolites, antimitotics, antiproliferatives, antivirals, aurora kinase inhibitors, other cell death activators (for example, other inhibitors of Bcl-2, Bcl-xL, Bcl-w, Bfl-1 or Mcl inhibitors), activators of death receptor pathways (for example, FAS or TRAIL agonists), Bcr-Abl kinase inhibitors, BET (bromodomain) inhibitors, BiTE (Bi-Specific T-cell Engager) antibodies, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, EGFR inhibitors, heat shock protein (HSP) inhibitors, histone deacetylase (HDAC) inhibitors, hormonal therapies, immunologicals, inhibitors of the inhibitors of apoptosis proteins (IAPs), intercalating antibiotics, kinase inhibitors, kinesin inhibitors, Jak2 inhibitors, mammalian target of rapamycin (mTOR) inhibitors, AKT inhibitors, microRNA's, mitogen-activated extracellular signal-regulated kinase (MEK) inhibitors, BRAF inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase inhibitors, proteosome inhibitors, purine analogs, pyrimidine analogs, receptor tyrosine kinase inhibitors, etinoids/deltoids plant alkaloids, small inhibitory ribonucleic acids (siRNAs), anti-CD20 compounds, topoisomerase inhibitors, and ubiquitin ligase inhibitors.

Alkylating agents include altretamine, AMD-473, AP-5280, apaziquone, bendamustine, brostallicin, busulfan, cisplatin, carboplatin, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, nitrosoureas, oxaliplatin, ranimustine, temozolomide, thiotepa, TREANDA® (bendamustine), treosulfan, rofosfamide and the like.

Angiogenesis inhibitors include endothelial-specific receptor, (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors, ALK inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflrnithine, EICAR (5-ethynyl-1-β-D-ribofuranosylimidazole-4-carboxamide), enocitabine, ethylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, pemextred, raltitrexed, Ribavirin, triapine, trimetrexate, S-1, tiazofurin, tegafur, TS-1, vidarabine, UFT and the like.

Bcl-2 protein inhibitors include ABT-199, AT-101 ((−) gossypol), GENASENSE® (G3139 or oblimersen (Bcl-2-targeting antisense oligonucleotide)), IPI-194, IPI-565, ABT-737, ABT-263, GX-070 (obatoclax), AMG-176, S63645 and the like.

Anti-CD20 compounds include rituximab and obinutuzumab.

Btk inhibitors include ibrutinib and acalabrutinib.

Bromodomain inhibitors include I-BET 762, OTX-015, CPI-203, LY294002 and the like.

CDK inhibitors include BMI-1040, BMS-032, BMS-387, CVT-2584, flavopiridol, GPC-286199, MCS-5A, PD0332991, PHA-690509, seliciclib (CYC-202, R-roscovitine), ZK-304709, AZD4573 and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib), TAGRISSO (AZD9291, osimertinib), and the like.

ALK inhibitors include crizotinib, ceritinib, and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 bifunctional bispecific antibodies, mAB AR-209, mAB 2B-1 and the like.

Antibody drug conjugates include anti-CD22-MC-MMAF, anti-CD22-MC-MMAE, anti-CD22-MCC-DM1, CR-011-vcMMAE, PSMA-ADC (e.g., MEDI3726), MEDI-547, SGN-19Am SGN-35, SGN-75 and the like.

Kinesin inhibitors include Eg5 inhibitors such as AZD4877, ARRY-520; CENPE inhibitors such as GSK923295A and the like.

MEK inhibitors include trametinib (GSK1120212), binimetinib (MEK162), selumetinib (AZD6244), cobimetinib (XL518), ARRY-142886, ARRY-438162, PD-325901, PD-98059, and the like.

BRAF inhibitors include sorafenib, vemurafenib, dabrafenib, GDC-0879, LGX818 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

VEGFR inhibitors include AVASTIN (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies (e.g., MEDI0629) and C-met specific antibodies, and the like.

WEE1 inhibitors include AZD1775 and the like.

Antitumor antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Inhibitors of DNA repair mechanisms such as CHK kinase; DNA-dependent protein kinase inhibitors; inhibitors of poly (ADP-ribose) polymerase (PARP inhibitors) including ABT-888 (veliparib), olaparib, KU-59436, AZD-2281, AG-014699, BSI-201, BGP-15, INO-1001, ONO-2231 and the like; and Hsp90 inhibitors such as tanespimycin and retaspimycin.

Proteasome inhibitors include VELCADE® (bortezomib), KYPROLIS (carfilzomib), NINLARO (ixazomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Additionally, the dendrimers of (I), (II), (III) and (IV) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN®

(DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

In one embodiment, disclosed is a method of treating cancer comprising administering to a subject in need thereof an effective amount of a dendrimer of formula (I), (II), (III), (IV) or (V), or a pharmaceutically acceptable salt thereof, in combination with an effective amount of osimertinib, or a pharmaceutically acceptable salt thereof. In some embodiments, disclosed is a method of treating lung cancer comprising administering to a subject in need thereof an effective amount of a dendrimer of formula (I), (II), (III), (IV) or (V), or a pharmaceutically acceptable salt thereof, in combination with an effective amount of osimertinib, or a pharmaceutically acceptable salt thereof. In some embodiments, disclosed is a method of treating EGFR T790M+ NSCLC comprising administering to a subject in need thereof an effective amount of a dendrimer of formula (I), (II), (III), (IV) or (V), or a pharmaceutically acceptable salt thereof, in combination with an effective amount of osimertinib, or a pharmaceutically acceptable salt thereof. In some embodiments, disclosed is a method of treating PTEN NSCLC comprising administering to a subject in need thereof an effective amount of a dendrimer of formula (I), (II), (III), (IV) or (V), or a pharmaceutically acceptable salt thereof, in combination with an effective amount of osimertinib, or a pharmaceutically acceptable salt thereof. In one embodiment, disclosed is a dendrimer of formula (I), (II), (III), (IV) or (V), or a pharmaceutically acceptable salt thereof, for the treatment of cancer in a subject, wherein said treatment comprises the separate, sequential or simultaneous administration of i) the dendrimer of formula (I), (II), (III), (IV) or (V), or a pharmaceutically acceptable salt thereof, and ii) osimertinib, or a pharmaceutically acceptable salt thereof, to said subject. In one embodiment, disclosed is a dendrimer of formula (I), (II), (III), (IV) or (V), or a pharmaceutically acceptable salt thereof, for the treatment of lung cancer in a subject, wherein said treatment comprises the separate, sequential or simultaneous administration of i) the dendrimer of formula (I), (II), (III), (IV) or (V), or a pharmaceutically acceptable salt thereof, and ii) osimertinib, or a pharmaceutically acceptable salt thereof, to said subject. In one embodiment, disclosed is a dendrimer of formula (I), (II), (III), (IV) or (V), or a pharmaceutically acceptable salt thereof, for the treatment of EGFR T790M+ NSCLC in a subject, wherein said treatment comprises the separate, sequential or simultaneous administration of i) the dendrimer of formula (I), (II), (III), (IV) or (V), or a pharmaceutically acceptable salt thereof, and ii) osimertinib, or a pharmaceutically acceptable salt thereof, to said subject. In one embodiment, disclosed is a dendrimer of formula (I), (II), (III), (IV) or (V), or a pharmaceutically acceptable salt thereof, for the treatment of PTEN NSCLC in a subject, wherein said treatment comprises the separate, sequential or simultaneous administration of i) the dendrimer of formula (I), (II), (III), (IV) or (V), or a pharmaceutically acceptable salt thereof, and ii) osimertinib, or a pharmaceutically acceptable salt thereof, to said subject. In one embodiment, disclosed is osimertinib, or a pharmaceutically acceptable salt thereof for the treatment of cancer in a subject, wherein said treatment comprises the separate, sequential or simultaneous administration of i) osimertinib, or a pharmaceutically acceptable salt thereof, and ii) a dendrimer of formula (I), (II), (III), (IV) or (V), or a pharmaceutically acceptable salt thereof, to said subject. In one embodiment, disclosed is osimertinib, or a pharmaceutically acceptable salt thereof for the treatment of lung cancer in a subject, wherein said treatment comprises the separate, sequential or simultaneous administration of i) osimertinib, or a pharmaceutically acceptable salt thereof, and ii) a dendrimer of formula (I), (II), (III), (IV) or (V), or a pharmaceutically acceptable salt thereof, to said subject. In one embodiment, disclosed is osimertinib, or a pharmaceutically acceptable salt thereof for the treatment of EGFR T790M+ NSCLC in a subject, wherein said treatment comprises the separate, sequential or simultaneous administration of i) osimertinib, or a pharmaceutically acceptable salt thereof, and ii) a dendrimer of formula (I), (II), (III), (IV) or (V), or a pharmaceutically acceptable salt thereof, to said subject. In one embodiment, disclosed is osimertinib, or a pharmaceutically acceptable salt thereof for the treatment of PTEN NSCLC in a subject, wherein said treatment comprises the separate, sequential or simultaneous administration of i) osimertinib, or a pharmaceutically acceptable salt thereof, and ii) a dendrimer of formula (I), (II), (III), (IV) or (V), or a pharmaceutically acceptable salt thereof, to said subject.

In one embodiment, disclosed is a method of treating cancer comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating lymphoma comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating Non-Hodgkin's lymphoma comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating DLBCL comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating activated B cell DLBCL (ABC-DLBCL) comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating BTK-sensitive and BTK-insensitive DLBCL comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In some embodiments, disclosed is a method of treating OCI-LY10 DLBCL comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating MCL comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating leukemia comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating CLL comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a method of treating AML comprising administering to a subject in need thereof an effective amount of a dendrimer of formula (I), (II), (III), (IV) or (V), or a pharmaceutically acceptable salt thereof, in combination with an effective amount of acalabrutinib, or a pharmaceutically acceptable salt thereof. In one embodiment, disclosed is a dendrimer of formula (I), (II), (III), (IV) or (V), or a pharmaceutically acceptable salt thereof, for treatment of cancer in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of non-Hodgkin's lymphoma in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of DLBCL in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of activated B-cell DLBCL (ABC-DLBCL) in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of BTK-sensitive and BTK-insensitive DLBCL in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of OCI-LY10 DLBCL in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of MCL in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of leukemia in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of CLL in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is a dendrimer of formula (I), (II), (III), (IV) or (V), or a pharmaceutically acceptable salt thereof, for treatment of AML in a subject, wherein said treatment comprises the separate, sequential or simultaneous administration of i) the dendrimer of formula (I), (II), (III), (IV) or (V), or a pharmaceutically acceptable salt thereof, and ii) acalabrutinib to said subject. In one embodiment, disclosed is acalabrutinib for treatment of cancer in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of DLBCL in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of activated B-cell DLBCL (ABC-DLBCL) in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of BTK-sensitive and BTK-insensitive DLBCL in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of OCI-LY10 DLBCL in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of MCL in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of leukemia in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of CLL in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject. In one embodiment, disclosed is acalabrutinib for treatment of AML in a subject, wherein said treatment comprises the separate, sequential or simultaneous administration of i) acalabrutinib, and ii) a dendrimer of formula (I), (II), (III), (IV) or (V), or a pharmaceutically acceptable salt thereof to said subject.

In one embodiment, disclosed is a method of treating cancer comprising administering to a subject in need thereof an effective amount of a dendrimer of formula (I), (II), (III), (IV) or (V), or a pharmaceutically acceptable salt thereof, in combination with an effective amount of rituximab, or a pharmaceutically acceptable salt thereof. In one embodiment, disclosed is a method of treating lymphoma comprising administering to a subject in need thereof an effective amount of a dendrimer of formula (I), (II), (III), (IV) or (V), or a pharmaceutically acceptable salt thereof, in combination with an effective amount of rituximab, or a pharmaceutically acceptable salt thereof. In one embodiment, disclosed is a method of treating Non-Hodgkin's lymphoma comprising administering to a subject in need thereof an effective amount of a dendrimer of (I), (II), (III), (IV) or (V), or a pharmaceutically acceptable salt thereof, in combination with an effective amount of rituximab, or a pharmaceutically acceptable salt thereof. In one embodiment, disclosed is a method of treating DLBCL comprising administering to a subject in need thereof an effective amount of a dendrimer of formula (I), (II), (III), (IV) or (V), or a pharmaceutically acceptable salt thereof, in combination with an effective amount of rituximab, or a pharmaceutically acceptable salt thereof. In one embodiment, disclosed is a method of treating activated germinal center B cell DLBCL (GCB-DLBCL) comprising administering to a subject in need thereof an effective amount of a dendrimer of formula (I), (II), (III), (IV) or (V), or a pharmaceutically acceptable salt thereof, in combination with an effective amount of rituximab, or a pharmaceutically acceptable salt thereof. In one embodiment, disclosed is a method of treating leukemia comprising administering to a subject in need thereof an effective amount of a dendrimer of formula (I), (II), (III), (IV) or (V), or a pharmaceutically acceptable salt thereof, in combination with an effective amount of rituximab, or a pharmaceutically acceptable salt thereof. In one embodiment, disclosed is a method of treating CLL comprising administering to a subject in need thereof an effective amount of a dendrimer of formula (I), (II), (III), (IV) or (V), or a pharmaceutically acceptable salt thereof, in combination with an effective amount of rituximab, or a pharmaceutically acceptable salt thereof. In one embodiment, disclosed is a method of treating AML comprising administering to a subject in need thereof an effective amount of a dendrimer of formula (I), (II), (III), (IV) or (V), or a pharmaceutically acceptable salt thereof, in combination with an effective amount of rituximab, or a pharmaceutically acceptable salt thereof.

In one embodiment, disclosed is a dendrimer of formula (I), (II), (III), (IV) or (V), or a pharmaceutically acceptable salt thereof, for treatment of cancer in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is a dendrimer of formula (I), (II), (III), (IV) or (V), or a pharmaceutically acceptable salt thereof, for treatment of lymphoma in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is a dendrimer of formula (I), (II), (III), (IV) or (V), or a pharmaceutically acceptable salt thereof, for treatment of non-Hodgkin's lymphoma in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is a dendrimer of formula (I), (II), (III), (IV) or (V), or a pharmaceutically acceptable salt thereof, for treatment of DLBCL in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is a dendrimer of formula (I), (II), (III), (IV) or (V), or a pharmaceutically acceptable salt thereof, for treatment of germinal cell B-cell DLBCL (GCB-DLBCL) in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is a dendrimer of formula (I), (II), (III), (IV) or (V), or a pharmaceutically acceptable salt thereof, for treatment of leukemia in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is a dendrimer of formula (I), (II), (III), (IV) or (V), or a pharmaceutically acceptable salt thereof, for treatment of CLL in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is a dendrimer of formula (I), (II), (III), (IV) or (V), or a pharmaceutically acceptable salt thereof, for treatment of AML in a subject, wherein said treatment comprises the separate, sequential or simultaneous administration of i) the dendrimer of formula (I), (II), (III), (IV) or (V), or a pharmaceutically acceptable salt thereof, and ii) rituximab to said subject. In one embodiment, disclosed is rituximab for treatment of cancer in a subject, wherein said treatment comprises the separate, sequential or simultaneous administration of i) rituximab and ii) a dendrimer of formula (I), (II), (III), (IV) or (V) to said subject. In one embodiment, disclosed is rituximab for treatment of lymphoma in a subject, wherein said treatment comprises the separate, sequential or simultaneous administration of i) rituximab and ii) a dendrimer of formula (I), (II), (III), (IV) or (V) to said subject. In one embodiment, disclosed is rituximab for treatment of non-Hodgkin's in a subject, wherein said treatment comprises the separate, sequential or simultaneous administration of i) rituximab and ii) a dendrimer of formula (I), (II), (III), (IV) or (V) to said subject. In one embodiment, disclosed is rituximab for treatment of DLBCL in a subject, wherein said treatment comprises the separate, sequential or simultaneous administration of i) rituximab and ii) a dendrimer of formula (I), (II), (III), (IV) or (V) to said subject. In one embodiment, disclosed is rituximab for treatment of germinal cell B-cell DLBCL (GBC-DLBCL) in a subject, wherein said treatment comprises the separate, sequential or simultaneous administration of i) rituximab and ii) a dendrimer of formula (I), (II), (III), (IV) or (V) to said subject. In one embodiment, disclosed is rituximab for treatment of leukemia in a subject, wherein said treatment comprises the separate, sequential or simultaneous administration of i) rituximab and ii) a dendrimer of formula (I), (II), (III), (IV) or (V) to said subject. In one embodiment, disclosed is rituximab for treatment of CLL in a subject, wherein said treatment comprises the separate, sequential or simultaneous administration of i) rituximab and ii) a dendrimer of formula (I), (II), (III), (IV) or (V) to said subject. In one embodiment, disclosed is rituximab for treatment of AML in a subject, wherein said treatment comprises the separate, sequential or simultaneous administration of i) rituximab and ii) a dendrimer of formula (I), (II), (III), (IV) or (V) to said subject.

In one embodiment, disclosed are methods of treating cancer comprising administering to a subject in need thereof an effective amount of a dendrimer of formula ((I), (II), (III), (IV) or (V), or a pharmaceutically acceptable salt thereof, in combination with an effective amount of gefitinib, or a pharmaceutically acceptable salt thereof. In one embodiment, disclosed are methods of treating solid tumors comprising administering to a subject in need thereof an effective amount of a dendrimer of formula (I), (II), (III), (IV) or (V), or a pharmaceutically acceptable salt thereof, in combination with an effective amount of gefitinib, or a pharmaceutically acceptable salt thereof. In one embodiment, disclosed is a method of treating NSCLC comprising administering to a subject in need thereof an effective amount of a dendrimer of formula (I), (II), (III), (IV) or (V), or a pharmaceutically acceptable salt thereof, in combination with an effective amount of gefitinib, or a pharmaceutically acceptable salt thereof. In one embodiment, disclosed is a method of treating EGFR mutation-positive NSCLC comprising administering to a subject in need thereof an effective amount of a dendrimer of formula (I), (II), (III), (IV) or (V), or a pharmaceutically acceptable salt thereof, in combination with an effective amount of gefitinib, or a pharmaceutically acceptable salt thereof. In one embodiment, disclosed is a method of treating EGFR mutation-positive non-small cell lung cancer whose tumors have exon 19 deletions or exon 21 (L858R) substitution mutations comprising administering to a subject in need thereof an effective amount of a dendrimer of formula (I), (II), (III), (IV) or (V), or a pharmaceutically acceptable salt thereof, in combination with an effective amount of gefitinib, or a pharmaceutically acceptable salt thereof. In one embodiment, disclosed is a dendrimer of formula (I), (II), (III), (IV) or (V), or a pharmaceutically acceptable salt thereof, for treatment of cancer in a subject, wherein said treatment comprises the separate, sequential or simultaneous administration of i) the dendrimer of formula (I), (II), (III), (IV) or (V), or a pharmaceutically acceptable salt thereof, and ii) gefitinib to said subject. In one embodiment, disclosed is a dendrimer of formula (I), (II), (III), (IV) or (V), or a pharmaceutically acceptable salt thereof, for treatment of solid tumors in a subject, wherein said treatment comprises the separate, sequential or simultaneous administration of i) the dendrimer of formula (I), (II), (III), (IV) or (V), or a pharmaceutically acceptable salt thereof, and ii) gefitinib to said subject. In one embodiment, disclosed is a dendrimer of formula (I), (II), (III), (IV) or (V), or a pharmaceutically acceptable salt thereof, for treatment of EGFR mutation-positive NSCLC in a subject, wherein said treatment comprises the separate, sequential or simultaneous administration of i) the dendrimer of formula (I), (II), (III), (IV) or (V), or a pharmaceutically acceptable salt thereof, and ii) gefitinib to said subject. In one embodiment, disclosed is a dendrimer of formula (I), (II), (III), (IV) or (V), or a pharmaceutically acceptable salt thereof, for treatment of EGFR mutation-positive non-small cell lung cancer whose tumors have exon 19 deletions or exon 21 (L858R) substitution mutations in a subject, wherein said treatment comprises the separate, sequential or simultaneous administration of i) the dendrimer of formula (I), (II), (III), (IV) or (V), or a pharmaceutically acceptable salt thereof, and ii) gefitinib to said subject. In one embodiment, disclosed is gefitinib for treatment of cancer in a subject, wherein said treatment comprises the separate, sequential or simultaneous administration of i) gefitinib and ii) a dendrimer of formula (I), (II), (III), (IV) or (V), or a pharmaceutically acceptable salt thereof, to said subject. In one embodiment, disclosed is gefitinib for treatment of solid tumors in a subject, wherein said treatment comprises the separate, sequential or simultaneous administration of i) gefitinib and ii) a dendrimer of formula (I), (II), (III), (IV) or (V), or a pharmaceutically acceptable salt thereof, to said subject. In one embodiment, disclosed is gefitinib for treatment of NSCLC in a subject, wherein said treatment comprises the separate, sequential or simultaneous administration of i) gefitinib and ii) a dendrimer of formula (I), (II), (III), (IV) or (V), or a pharmaceutically acceptable salt thereof, to said subject. In one embodiment, disclosed is gefitinib for treatment of EGFR mutation-positive NSCLC in a subject, wherein said treatment comprises the separate, sequential or simultaneous administration of i) gefitinib and ii) a dendrimer of formula (I), (II), (III), (IV) or (V), or a pharmaceutically acceptable salt thereof, to said subject. In one embodiment, disclosed is gefitinib for treatment of s in a subject, wherein said treatment comprises the separate, sequential or simultaneous administration of i) gefitinib and ii) a dendrimer of formula (I), (II), (III), (IV) or (V), or a pharmaceutically acceptable salt thereof, to said subject.

In one embodiment, disclosed are methods of treating cancer comprising administering to a subject in need thereof an effective amount of a dendrimer of formula (I), (II), (III), (IV) or (V), or a pharmaceutically acceptable salt thereof, in combination with an effective amount of olaparib, or a pharmaceutically acceptable salt thereof. In one embodiment, disclosed are methods of treating solid tumors comprising administering to a subject in need thereof an effective amount of a dendrimer of formula (I), (II), (III), (IV) or (V), or a pharmaceutically acceptable salt thereof, in combination with an effective amount of olaparib, or a pharmaceutically acceptable salt thereof. In one embodiment, disclosed are methods of treating ovarian cancer comprising administering to a subject in need thereof an effective amount of a dendrimer of formula (I), (II), (III), (IV) or (V), or a pharmaceutically acceptable salt thereof, in combination with an effective amount of olaparib, or a pharmaceutically acceptable salt thereof. In one embodiment, disclosed are methods of treating BRCA-mutated ovarian cancer comprising administering to a subject in need thereof an effective amount of a dendrimer of formula (I), (II), (III), (IV) or (V), or a pharmaceutically acceptable salt thereof, in combination with an effective amount of olaparib, or a pharmaceutically acceptable salt thereof. In one embodiment, disclosed are methods of treating epithelial ovarian cancer comprising administering to a subject in need thereof an effective amount of a dendrimer of formula (I), (II), (III), (IV) or (V), or a pharmaceutically acceptable salt thereof, in combination with an effective amount of olaparib, or a pharmaceutically acceptable salt thereof. In one embodiment, disclosed are methods of treating fallopian tube cancer comprising administering to a subject in need thereof an effective amount of a dendrimer of formula (I), (II), (III), (IV) or (V), or a pharmaceutically acceptable salt thereof, in combination with an effective amount of olaparib, or a pharmaceutically acceptable salt thereof. In one embodiment, disclosed are methods of treating primary peritoneal cancer comprising administering to a subject in need thereof an effective amount of a dendrimer of formula (I), (II), (III), (IV) or (V), or a pharmaceutically acceptable salt thereof, in combination with an effective amount of olaparib, or a pharmaceutically acceptable salt thereof. In one embodiment, disclosed is a dendrimer of formula (I), (II), (III), (IV) or (V), or a pharmaceutically acceptable salt thereof, for treatment of cancer in a subject, wherein said treatment comprises the separate, sequential or simultaneous administration of i) the dendrimer of formula (I), (II), (III), (IV) or (V), or a pharmaceutically acceptable salt thereof, and ii) olaparib, or a pharmaceutically acceptable salt thereof, to said subject. In one embodiment, disclosed is a dendrimer of formula (I), (II), (III), (IV) or (V), or a pharmaceutically acceptable salt thereof, for treatment of solid tumors in a subject, wherein said treatment comprises the separate, sequential or simultaneous administration of i) the dendrimer of formula (I), (II), (III), (IV) or (V), or a pharmaceutically acceptable salt thereof, and ii) olaparib, or a pharmaceutically acceptable salt thereof, to said subject. In one embodiment, disclosed is a dendrimer of formula (I), (II), (III), (IV) or (V), or a pharmaceutically acceptable salt thereof, for treatment of ovarian cancer in a subject, wherein said treatment comprises the separate, sequential or simultaneous administration of i) the dendrimer of formula (I), (II), (III), (IV) or (V), or a pharmaceutically acceptable salt thereof, and ii) olaparib, or a pharmaceutically acceptable salt thereof, to said subject. In one embodiment, disclosed is a dendrimer of formula (I), (II), (III), (IV) or (V), or a pharmaceutically acceptable salt thereof, for treatment of BRCA-mutated ovarian cancer in a subject, wherein said treatment comprises the separate, sequential or simultaneous administration of i) the dendrimer of formula (I), (II), (III), (IV) or (V), or a pharmaceutically acceptable salt thereof, and ii) olaparib, or a pharmaceutically acceptable salt thereof, to said subject. In one embodiment, disclosed is a dendrimer of formula (I), (II), (III), (IV) or (V), or a pharmaceutically acceptable salt thereof, for treatment of epithelial ovarian cancer in a subject, wherein said treatment comprises the separate, sequential or simultaneous administration of i) the dendrimer of formula (I), (II), (III), (IV) or (V), or a pharmaceutically acceptable salt thereof, and ii) olaparib, or a pharmaceutically acceptable salt thereof, to said subject. In one embodiment, disclosed is a dendrimer of formula (I), (II), (III), (IV) or (V), or a pharmaceutically acceptable salt thereof, for treatment of fallopian tube cancer in a subject, wherein said treatment comprises the separate, sequential or simultaneous administration of i) the dendrimer of formula (I), (II), (III), (IV) or (V), or a pharmaceutically acceptable salt thereof, and ii) olaparib, or a pharmaceutically acceptable salt thereof, to said subject. In one embodiment, disclosed is a dendrimer of formula (I), (II), (III), (IV) or (V), or a pharmaceutically acceptable salt thereof, for treatment of primary peritoneal cancer in a subject, wherein said treatment comprises the separate, sequential or simultaneous administration of i) the dendrimer of formula (I), (II), (III), (IV) or (V), or a pharmaceutically acceptable salt thereof, and ii) olaparib, or a pharmaceutically acceptable salt thereof, to said subject. In one embodiment, disclosed is olaparib, or a pharmaceutically acceptable salt thereof, for treatment of cancer in a subject, wherein said treatment comprises the separate, sequential or simultaneous administration of i) olaparib, or a pharmaceutically acceptable salt thereof, and ii) a dendrimer of formula (I), (II), (III), (IV) or (V), or a pharmaceutically acceptable salt thereof, to said subject. In one embodiment, disclosed is olaparib, or a pharmaceutically acceptable salt thereof, for treatment of solid tumors in a subject, wherein said treatment comprises the separate, sequential or simultaneous administration of i) olaparib, or a pharmaceutically acceptable salt thereof, and ii) a dendrimer of formula (I), (II), (III), (IV) or (V), or a pharmaceutically acceptable salt thereof, to said subject. In one embodiment, disclosed is olaparib, or a pharmaceutically acceptable salt thereof, for treatment of ovarian cancer in a subject, wherein said treatment comprises the separate, sequential or simultaneous administration of i) olaparib, or a pharmaceutically acceptable salt thereof, and ii) a dendrimer of formula (I), (II), (III), (IV) or (V), or a pharmaceutically acceptable salt thereof, to said subject. In one embodiment, disclosed is olaparib, or a pharmaceutically acceptable salt thereof, for treatment of BRCA-mutated ovarian cancer in a subject, wherein said treatment comprises the separate, sequential or simultaneous administration of i) olaparib, or a pharmaceutically acceptable salt thereof, and ii) a dendrimer of formula (I), (II), (III), (IV) or (V), or a pharmaceutically acceptable salt thereof, to said subject. In one embodiment, disclosed is olaparib, or a pharmaceutically acceptable salt thereof, for treatment of epithelial ovarian cancer in a subject, wherein said treatment comprises the separate, sequential or simultaneous administration of i) olaparib, or a pharmaceutically acceptable salt thereof, and ii) a dendrimer of formula (I), (II), (III), (IV) or (V), or a pharmaceutically acceptable salt thereof, to said subject. In one embodiment, disclosed is olaparib, or a pharmaceutically acceptable salt thereof, for treatment of fallopian tube cancer in a subject, wherein said treatment comprises the separate, sequential or simultaneous administration of i) olaparib, or a pharmaceutically acceptable salt thereof, and ii) a dendrimer of formula (I), (II), (III), (IV) or (V), or a pharmaceutically acceptable salt thereof, to said subject. In one embodiment, disclosed is olaparib, or a pharmaceutically acceptable salt thereof, for treatment of primary peritoneal cancer in a subject, wherein said treatment comprises the separate, sequential or simultaneous administration of i) olaparib, or a pharmaceutically acceptable salt thereof, and ii) a dendrimer of formula (I), (II), (III), (IV) or (V), or a pharmaceutically acceptable salt thereof, to said subject.

In one embodiment, disclosed are methods of treating cancer comprising administering to a subject in need thereof an effective amount of a dendrimer of formula (I), (II), (III), (IV) or (V), or a pharmaceutically acceptable salt thereof, in combination with an effective amount of an mTOR inhibitor, or a pharmaceutically acceptable salt thereof. In one embodiment, disclosed are methods of treating small cell lung cancer comprising administering to a subject in need thereof an effective amount of a dendrimer of formula (I), (II), (III), (IV) or (V), or a pharmaceutically acceptable salt thereof, in combination with an effective amount of an mTOR inhibitor, or a pharmaceutically acceptable salt thereof. In one embodiment, disclosed is a dendrimer of formula (I), (II), (III), (IV) or (V), or a pharmaceutically acceptable salt thereof, for treatment of cancer in a subject, wherein said treatment comprises the separate, sequential or simultaneous administration of i) the dendrimer of formula (I), (II), (III), (IV) or (V), or a pharmaceutically acceptable salt thereof, and ii) an mTOR inhibitor, or a pharmaceutically acceptable salt thereof, to said subject. In one embodiment, disclosed is a dendrimer of formula (I), (II), (III), (IV) or (V), or a pharmaceutically acceptable salt thereof, for treatment of small-cell lung cancer in a subject, wherein said treatment comprises the separate, sequential or simultaneous administration of i) the dendrimer of formula (I), (II), (III), (IV) or (V), or a pharmaceutically acceptable salt thereof, and ii) an mTOR inhibitor or a pharmaceutically acceptable salt thereof, to said subject. In one embodiment, disclosed is an mTOR inhibitor, or a pharmaceutically acceptable salt thereof, for treatment of cancer in a subject, wherein said treatment comprises the separate, sequential or simultaneous administration of i) an mTOR inhibitor, and ii) a dendrimer of formula (I), (II), (III), (IV) or (V), or a pharmaceutically acceptable salt thereof, to said subject. In one embodiment, disclosed is an mTOR inhibitor, or a pharmaceutically acceptable salt thereof, for treatment of small-cell lung cancer in a subject, wherein said treatment comprises the separate, sequential or simultaneous administration of i) an mTOR inhibitor, and ii) a dendrimer of formula (I), (II), (III), (IV) or (V), or a pharmaceutically acceptable salt thereof, to said subject. In any of the foregoing embodiments, the mTOR inhibitor is AZD2014.

In one embodiment, disclosed are methods of treating cancer comprising administering to a subject in need thereof an effective amount of a dendrimer of formula (I), (II), (III), (IV) or (V), or a pharmaceutically acceptable salt thereof, in combination with an effective amount of an vistusertib, or a pharmaceutically acceptable salt thereof. In one embodiment, disclosed are methods of treating small cell lung cancer comprising administering to a subject in need thereof an effective amount of a dendrimer of formula (I), (II), (III), (IV) or (V), or a pharmaceutically acceptable salt thereof, in combination with an effective amount of vistusertib, or a pharmaceutically acceptable salt thereof. In one embodiment, disclosed is a dendrimer of formula (I), (II), (III), (IV) or (V), or a pharmaceutically acceptable salt thereof, for treatment of cancer in a subject, wherein said treatment comprises the separate, sequential or simultaneous administration of i) the dendrimer of formula (I), (II), (III), (IV) or (V), or a pharmaceutically acceptable salt thereof, and ii) vistusertib, or a pharmaceutically acceptable salt thereof, to said subject. In one embodiment, disclosed is a dendrimer of formula (I), (II), (III), (IV) or (V), or a pharmaceutically acceptable salt thereof, for treatment of small cell lung cancer in a subject, wherein said treatment comprises the separate, sequential or simultaneous administration of i) the dendrimer of formula (I), (II), (III), (IV) or (V), or a pharmaceutically acceptable salt thereof, and ii) vistusertib, or a pharmaceutically acceptable salt thereof, to said subject. In one embodiment, disclosed is vistusertib, or a pharmaceutically acceptable salt thereof, for treatment of cancer in a subject, wherein said treatment comprises the separate, sequential or simultaneous administration of i) vistusertib, or a pharmaceutically acceptable salt thereof, and ii) a dendrimer of formula (I), (II), (III), (IV) or (V), or a pharmaceutically acceptable salt thereof, to said subject. In one embodiment, disclosed is vistusertib, or a pharmaceutically acceptable salt thereof, for treatment of small cell lung cancer in a subject, wherein said treatment comprises the separate, sequential or simultaneous administration of i) vistusertib, or a pharmaceutically acceptable salt thereof, and ii) a dendrimer of formula (I), (II), (III), (IV) or (V), or a pharmaceutically acceptable salt thereof, to said subject.

In one embodiment, disclosed are methods of treating cancer comprising administering to a subject in need thereof an effective amount of a dendrimer of formula (I), (II), (III), (IV) or (V), or a pharmaceutically acceptable salt thereof, in combination with an effective amount of chemotherapy (e.g., topotecan, pemetrexed, paclitaxel, etoposide and/or carboplatin). In one embodiment, disclosed are methods of treating solid tumors comprising administering to a subject in need thereof an effective amount of a dendrimer of formula (I), (II), (III), (IV) or (V), or a pharmaceutically acceptable salt thereof, in combination with an effective amount of chemotherapy (e.g., topotecan, pemetrexed, paclitaxel, etoposide and/or carboplatin). In one embodiment, disclosed are methods of treating NSCLC comprising administering to a subject in need thereof an effective amount of a dendrimer of formula (I), (II), (III), (IV) or (V), or a pharmaceutically acceptable salt thereof, in combination with an effective amount of chemotherapy (e.g., topotecan, pemetrexed, paclitaxel, etoposide and/or carboplatin). In one embodiment, disclosed are methods of treating SCLC cancer comprising administering to a subject in need thereof an effective amount of a dendrimer of formula (I), (II), (III), (IV) or (V), or a pharmaceutically acceptable salt thereof, in combination with an effective amount of chemotherapy (e.g., topotecan, pemetrexed, paclitaxel, etoposide and/or carboplatin). In one embodiment, disclosed are methods of treating breast cancer comprising administering to a subject in need thereof an effective amount of a dendrimer of formula (I), (II), (III), (IV) or (V), or a pharmaceutically acceptable salt thereof, in combination with an effective amount of chemotherapy (e.g., topotecan, pemetrexed, paclitaxel, etoposide and/or carboplatin). In one embodiment, disclosed are methods of treating ovarian cancer comprising administering to a subject in need thereof an effective amount of a dendrimer of formula (I), (II), (III), (IV) or (V), or a pharmaceutically acceptable salt thereof, in combination with an effective amount of chemotherapy (e.g., topotecan, pemetrexed, paclitaxel, etoposide and/or carboplatin).

In one embodiment, disclosed is a dendrimer of formula (I), (II), (III), (IV) or (V), or a pharmaceutically acceptable salt thereof, for treatment of cancer in a subject, wherein said treatment comprises the separate, sequential or simultaneous administration of i) the dendrimer of formula (I), (II), (III), (IV) or (V), or a pharmaceutically acceptable salt thereof, and ii) chemotherapy (e.g., topotecan, pemetrexed, paclitaxel, etoposide and/or carboplatin) to said subject. In one embodiment, disclosed is a dendrimer of formula (I), (II), (III), (IV) or (V), or a pharmaceutically acceptable salt thereof, for treatment of solid tumors in a subject, wherein said treatment comprises the separate, sequential or simultaneous administration of i) the dendrimer of formula (I), (II), (III), (IV) or (V), or a pharmaceutically acceptable salt thereof, and ii) chemotherapy (e.g., topotecan, pemetrexed, paclitaxel, etoposide and/or carboplatin) to said subject. In one embodiment, disclosed is a dendrimer of formula (I), (II), (III), (IV) or (V), or a pharmaceutically acceptable salt thereof, for treatment of NSCLC in a subject, wherein said treatment comprises the separate, sequential or simultaneous administration of i) the dendrimer of formula (I), (II), (III), (IV) or (V), or a pharmaceutically acceptable salt thereof, and ii) chemotherapy (e.g., topotecan, pemetrexed, paclitaxel, etoposide and/or carboplatin) to said subject. In one embodiment, disclosed is a dendrimer of formula (I), (II), (III), (IV) or (V), or a pharmaceutically acceptable salt thereof, for treatment of SCLC in a subject, wherein said treatment comprises the separate, sequential or simultaneous administration of i) the dendrimer of formula (I), (II), (III), (IV) or (V), or a pharmaceutically acceptable salt thereof, and ii) chemotherapy (e.g., topotecan, pemetrexed, paclitaxel, etoposide and/or carboplatin) to said subject. In one embodiment, disclosed is a dendrimer of formula (I), (II), (III), (IV) or (V), or a pharmaceutically acceptable salt thereof, for treatment of breast cancer in a subject, wherein said treatment comprises the separate, sequential or simultaneous administration of i) the dendrimer of formula (I), (II), (III), (IV) or (V), or a pharmaceutically acceptable salt thereof, and ii) chemotherapy (e.g., topotecan, pemetrexed, paclitaxel, etoposide and/or carboplatin) to said subject. In one embodiment, disclosed is a dendrimer of formula (I), (II), (III), (IV) or (V), or a pharmaceutically acceptable salt thereof, for treatment of ovarian cancer in a subject, wherein said treatment comprises the separate, sequential or simultaneous administration of i) the dendrimer of formula (I), (II), (III), (IV) or (V), or a pharmaceutically acceptable salt thereof, and ii) chemotherapy (e.g., topotecan, pemetrexed, paclitaxel, etoposide and/or carboplatin) to said subject. In one embodiment, disclosed is chemotherapy (e.g., topotecan, pemetrexed, paclitaxel, etoposide and/or carboplatin) for treatment of cancer in a subject, wherein said treatment comprises the separate, sequential or simultaneous administration of i) the chemotherapy (e.g., topotecan, pemetrexed, paclitaxel, etoposide and/or carboplatin), and ii) a dendrimer of formula (I), (II), (III), (IV) or (V), or a pharmaceutically acceptable salt thereof, to said subject. In one embodiment, disclosed is chemotherapy (e.g., topotecan, pemetrexed, paclitaxel, etoposide and/or carboplatin) for treatment of solid tumors in a subject, wherein said treatment comprises the separate, sequential or simultaneous administration of i) the chemotherapy (e.g., topotecan, pemetrexed, paclitaxel, etoposide and/or carboplatin), and ii) a dendrimer of formula (I), (II), (III), (IV) or (V), or a pharmaceutically acceptable salt thereof, to said subject. In one embodiment, disclosed is chemotherapy (e.g., topotecan, pemetrexed, paclitaxel, etoposide and/or carboplatin) for treatment of NSCLC in a subject, wherein said treatment comprises the separate, sequential or simultaneous administration of i) the chemotherapy (e.g., topotecan, pemetrexed, paclitaxel, etoposide and/or carboplatin), and ii) a dendrimer of formula (I), (II), (III), (IV) or (V), or a pharmaceutically acceptable salt thereof, to said subject. In one embodiment, disclosed is chemotherapy (e.g., topotecan, pemetrexed, paclitaxel, etoposide and/or carboplatin) for treatment of SCLC in a subject, wherein said treatment comprises the separate, sequential or simultaneous administration of i) the chemotherapy (e.g., topotecan, pemetrexed, paclitaxel, etoposide and/or carboplatin), and ii) a dendrimer of formula (I), (II), (III), (IV) or (V), or a pharmaceutically acceptable salt thereof, to said subject. In one embodiment, disclosed is chemotherapy (e.g., topotecan, pemetrexed, paclitaxel, etoposide and/or carboplatin) for treatment of breast cancer in a subject, wherein said treatment comprises the separate, sequential or simultaneous administration of i) the chemotherapy (e.g., topotecan, pemetrexed, paclitaxel, etoposide and/or carboplatin), and ii) a dendrimer of formula (I), (II), (III), (IV) or (V), or a pharmaceutically acceptable salt thereof, to said subject. In one embodiment, disclosed is chemotherapy (e.g., topotecan, pemetrexed, paclitaxel, etoposide and/or carboplatin) for treatment of ovarian cancer in a subject, wherein said treatment comprises the separate, sequential or simultaneous administration of i) the chemotherapy (e.g., topotecan, pemetrexed, paclitaxel, etoposide and/or carboplatin), and ii) a dendrimer of formula (I), (II), (III), (IV) or (V), or a pharmaceutically acceptable salt thereof, to said subject.

In one aspect, disclosed are methods for inhibiting Bcl-2 and/or Bcl-XL in a subject in need thereof, comprising administering to the subject an effective amount of a dendrimer of formula (I), (II), (III), (IV) or (V), or a pharmaceutically acceptable salt thereof.

In one aspect, disclosed is a dendrimer of formula (I), (II), (III), (IV) or (V), or a pharmaceutically acceptable salt thereof, for use in inhibiting Bcl-2 and/or Bcl-XL.

In one aspect, disclosed is the use of a dendrimer of formula (I), (II), (III), (IV) or (V), or a pharmaceutically acceptable salt thereof, in the manufacture of a medicament for inhibiting Bcl-2 and/or Bcl-XL.

In one aspect, disclosed are pharmaceutical compositions comprising a dendrimer of formula (I), (II), (III), (IV) or (V), or a pharmaceutically acceptable salt thereof, for use in inhibiting Bcl-2 and/or Bcl-XL.

The term "Bcl-2" refers to B-cell lymphoma 2 and the term "Bcl-XL" refers to B-cell lymphoma extra-large, anti-apoptotic members of the BCL-2 family of proteins.

The language "effective amount" includes an amount of a dendrimer of formula (I), (II), (III), (IV) or (V), or a pharmaceutically acceptable salt thereof, or a second anti-cancer agent that will elicit a biological or medical response in a subject, for example, the reduction or inhibition of enzyme or protein activity related to Bcl-2 and/or Bcl-XL or cancer; amelioration of symptoms of cancer; or the slowing or delaying of progression of cancer. In some embodiments, the language "effective amount" includes the amount of a dendrimer of formula (I), (II), (III), (IV) or (V), or a pharmaceutically acceptable salt thereof, or second anti-cancer agent, that when administered to a subject, is effective to at least partially alleviate, inhibit, and/or ameliorate cancer or inhibit Bcl-2 and/or Bcl-XL, and/or reduce or inhibit the growth of a tumor or proliferation of cancerous cells in a subject.

In some embodiments, an effective amount of a dendrimer of formula (I), (II), (III), (IV) or (V), or a pharmaceutically acceptable salt thereof, may be between about 1 and about 500 mg/kg. In some embodiments, an effective amount of a dendrimer of formula (I), (II), (III), (IV) or (V), or a pharmaceutically acceptable salt thereof, may be between about 10 and about 300 mg/kg. In some embodiments, an effective amount of a dendrimer of formula (I), (II), (III), (IV) or (V), or a pharmaceutically acceptable salt thereof, may be between about 10 and about 100 mg/kg. In some embodiments, an effective amount of a dendrimer of formula (I), (II), (III), (IV) or (V), or a pharmaceutically acceptable salt thereof, may be between about 10 and about 60 mg/kg. In some embodiments, an effective amount of a disclosed a dendrimer of formula (I), (II), (III), (IV) or (V), or a pharmaceutically acceptable salt thereof, may be between about 10 and about 30 mg/kg. In some embodiments, an effective amount of a dendrimer of (I), (II), (III), (IV) or (V) may be about 20 to about 100 mg/kg. In some embodiments, an effective amount of a dendrimer of formula (I), (II), (III), (IV) or (V), or a pharmaceutically acceptable salt thereof, may be about 10 mg/kg, about 30 mg/kg, about 40 mg/kg, about 50 mg/kg, about 60 mg/kg, about 70 mg/kg, about 80 mg/kg, about 90 mg/kg, about 100 mg/kg, about 300 mg/kg or about 145 mg/kg.

The a dendrimer of formula (I), (II), (III), (IV) or (V), or a pharmaceutically acceptable salt thereof, may be designed to release the active agent from the surface functional groups of the dendrimer. In some embodiments, the dendrimer of formula (I), (II), (III), (IV) or (V), or a pharmaceutically acceptable salt thereof, releases an effective amount Compound A. In some embodiments, the dendrimer of formula (I), (II), (III), (IV) or (V), or a pharmaceutically acceptable salt thereof, may release between about 1 mg/kg and about 150 mg/kg of Compound A. In some embodiments, the dendrimer of formula (I), (II), (III), (IV) or (V), or a pharmaceutically acceptable salt thereof, may release between about 1 mg/kg and about 90 mg/kg of Compound A. In some embodiments, the dendrimer of formula (I), (II), (III), (IV) or (V), or a pharmaceutically acceptable salt thereof, may release between about 1 mg/kg and about 25 mg/kg of Compound A. In some embodiments, the dendrimer of formula (I), (II), (III), (IV) or (V), or a pharmaceutically acceptable salt thereof, may release between about 1 mg/kg and about 15 mg/kg of Compound A. In some embodiments, the dendrimer of formula (I), (II), (III), (IV) or (V), or a pharmaceutically acceptable salt thereof, may release between about 1 and about 10 mg of Compound A. In some embodiments, the dendrimer of formula (I), (II), (III), (IV) or (V), or a pharmaceutically acceptable salt thereof, may release between about 5 and about 30 mg/kg of Compound A. In some embodiments, the dendrimer of formula (I), (II), (III), (IV) or (V), or a pharmaceutically acceptable salt thereof, may release about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 87 mg/kg or about 145 mg/kg Compound A.

In some embodiments, Compound A may have a release half-life (e.g., time it takes for half of Compound A to be released from the dendrimer) of between about 1 hour and about 360 hours. In some embodiments, Compound A may have a release half-life of between about 2 hours and about 72 hours. In some embodiments, Compound A may have a release half-life of between about 5 hours and about 36 hours. In some embodiments, Compound A may have a release half-life of between about 12 hours and about 30 hours. In some embodiments, Compound A may have a release half-life of between about 16 and about 30 hours. In some embodiments, the release half-life is determined at pH 7.4 in PBS buffer with 10% DMA at 37° C. In some embodiments, the release half-life is determined at pH 4.5 in 0.1M citric acid at 37° C. One of skill in the art could determine the release rate of Compound A in vitro by following the protocols set forth in Examples 11, 12 and Example 14.

In some embodiments, the in vitro release half-life is determined at pH 7.4 in PBS buffer with 10% DMA at 37° C., as described in Example 11. In some embodiments, between about 20 and about 80% of Compound A is released after about 6 hours at pH 7.4 in PBS buffer with 10% DMA at 37° C. In some embodiments, about 80% of Compound A is released after about 6.5 hours at pH 7.4 in PBS buffer with 10% DMA at 37° C. In some embodiments, about 50% of Compound A is released after about 6.5 hours at pH 7.4 in PBS buffer with 10% DMA at 37° C. In some embodiments, about 6% of Compound A is released after about 6.5 hours at pH 7.4 in PBS buffer with 10% DMA at 37° C. In some embodiments, about 4% of Compound A is released after about 6.5 hours at pH 7.4 in PBS buffer with 10%/o DMA at 37° C. In some embodiments, about 24% of Compound A is released after about 6 hours at pH 7.4 in PBS buffer with 10%/o DMA at 37° C.

In some embodiments, the in vitro release half-life is determined at pH 4.5 in 0.1M citric acid at 37° C., as described in Example 12. In some embodiments, between about 3 and about 80% of Compound A is released after about 7 days at pH 4.5 in 0.1M citric acid at 37° C. In some embodiments, about 63% of Compound A is released after about 7 days at pH 4.5 in 0.1 M citric acid at 37° C. In some embodiments, about 30% of Compound A is released after about 7 days at pH 4.5 in 0.1M citric acid at 37° C. In some embodiments, about 3.6% of Compound A is released after about 7 days at pH 4.5 in 0.1M citric acid at 37° C. In some embodiments, about 81% of Compound A is released after about 7 days at pH 4.5 in 0.1M citric acid at 37° C.

In some embodiments, the solubility of the dendrimer can be measured following the protocols set forth in Examples 15 and 16. In some embodiments, the solubility of the dendrimer at pH 7.4 in PBS buffer with 10% DMA is between about 120 and 160 mg/mL. In some embodiments, the solubility of the dendrimer at pH 7.4 in PBS buffer with 10% DMA is about 125 mg/mL. In some embodiments, the solubility of the dendrimer at pH 7.4 in PBS buffer with 10% DMA is about 153 mg/mL. In some embodiments, the solubility of the dendrimer at pH 7.4 in PBS buffer with 10% DMA is about 142 mg/mL. In some embodiments, the solubility of the dendrimer at pH 7.4 in PBS buffer with 10% DMA is about 158 mg/mL.

In some embodiments, the solubility of the dendrimer pH 4.5 in 0.1M citric acid is between about 120 and 166 mg/mL. In some embodiments, the solubility of the dendrimer pH 4.5 in 0.1M citric acid is about 162 mg/mL. In some embodiments, the solubility of the dendrimer pH 4.5 in 0.1M citric acid is about 141 mg/mL. In some embodiments, the solubility of the dendrimer pH 4.5 in 0.1M citric acid is about 157 mg/mL. In some embodiments, the solubility of the dendrimer pH 4.5 in 0.1M citric acid is about 121 mg/mL.

In some embodiments, the solubility of the dendrimer in McIlvane buffer pH 4 is about 0.189 g/g. In some embodiments, the solubility of the dendrimer in McIlvane buffer pH 5 is about 0.224 g/g.

The term "subject" includes warm blooded mammals, for example, primates, dogs, cats, rabbits, rats, and mice. In some embodiments, the subject is a primate, for example, a human. In some embodiments, the subject is suffering from cancer or an immune disorder. In some embodiments, the subject is in need of treatment (e.g., the subject would benefit biologically or medically from treatment). In some embodiments, the subject is suffering from cancer. In some embodiments, the subject is suffering from a EGFR-M positive cancer (e.g., non-small cell lung cancer). In some embodiments, the EGFR-M positive cancer has a predominately T790M-positive mutation. In some embodiments, the EGFR-M positive cancer has a predominately T790M-negative mutation. In some embodiments, the subject is suffering from a hematological (e.g., lymphomas, leukemia) or solid malignancy, such as, for example, acute lymphoblastic lymphoma (ALL), acute myelogenous leukemia (AML), chronic lymphocytic leukemia (CLL), small lymphocytic lymphoma (SLL), chronic myelogenous leukemia (CML), acute monocytic leukemia (AMoL), multiple myeloma, mantle cell lymphoma, diffuse large B cell lymphoma (DLBCL), Burkitt's lymphoma, Non-Hodgkin's lymphoma, follicular lymphoma and solid tumors, for example, non-small cell lung cancer (NSCLC), small cell lung cancer (SCLC), breast cancer, neuroblastoma, prostate cancer, melanoma, pancreatic cancer, uterine, endometrial and colon cancer.

The language "inhibit," "inhibition" or "inhibiting" includes a decrease in the baseline activity of a biological activity or process. In some embodiments, the dendrimers of formula (I), (II), (III) or (IV) inhibit Bcl-2 and/or Bcl-XL.

The language "treat," "treating" and "treatment" includes the reduction or inhibition of enzyme or protein activity related to Bcl-2 and/or Bcl-XL or cancer in a subject, amelioration of one or more symptoms of cancer in a subject, or the slowing or delaying of progression of cancer in a subject. The language "treat," "treating" and "treatment" also includes the reduction or inhibition of the growth of a tumor or proliferation of cancerous cells in a subject.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:
(i) all syntheses were carried out at ambient temperature, i.e. in the range 17 to 25° C. and under an atmosphere of an inert gas such as nitrogen unless otherwise stated;
(ii) evaporations were carried out by rotary evaporation under reduced pressure, using Buchi or Heidolph equipment;
(iii) lyophilisation was carried out using a Labconco FreeZone 6 Plus freeze dry system;
(iv) size exclusion chromatography purifications were performed using columns packed with Sephadex LH-20 beads;
(v) preparative chromatography was performed on a Gilson Prep GX-271 system with UV-triggered collection, using a Waters XBridge BEH C18 (5 µM, 30×150 mm) column;
(vi) ultrafiltration purifications were performed using a Cole-Parmer gear pump drive system connected to a membrane cassette (Merck Millipore Pellicon 3, 0.11 m2, 10 kDa).
(vii) analytical chromatography was performed on a Waters Alliance 2695 Separation Module with PDA detection;
(viii) yields, where present, are not necessarily the maximum attainable;
(ix) in general, the structures of end products of the dendrimers were confirmed by NMR spectroscopy; $^1$H and $^{19}$F NMR chemical shift values were measured on the delta scale, [proton magnetic resonance spectra were determined using a Bruker Avance 300 (300 MHz) instrument]; measurements were taken at ambient temperature unless otherwise specified; 1H NMR use the solvent residual peak as the internal standard and the following abbreviations: s, singlet; d, doublet; t, triplet; q, quartet; m, multiplet; dd, doublet of doublets; ddd, doublet of doublet of doublet; dt, doublet of triplets; br s, broad singlet;
(x) in general, dendrimer end products were also characterized by HPLC, using a Waters Alliance 2695 Separation Module with PDA detection, connected to either a Waters XBridge C8 (3.5 µm, 3×100 mm) or a Phenomenex Aeris C8 (3.6 µm, 2.1×100 mm) column;
(xi) intermediate purity was assessed by mass spectroscopy following liquid chromatography (LC-MS); using a Waters UPLC fitted with a Waters SQ mass spectrometer (Column temp 40° C., UV=220-300 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 µm, 2.1×50 mm), for basic analysis the column used was a Waters Acquity BEH C18 (1.7 µm, 2.1×50 mm). Alternatively, UPLC was carried out using a Waters UPLC fitted with a Waters SQ mass spectrometer (Column temp 30° C., UV=210-400 nm, Mass Spec=ESI with positive/negative switching) at a flow rate of 1 mL/min using a solvent gradient of 2 to 98% B over 1.5 min (total run time with equilibration back to starting conditions 2 min), where A=0.1% formic acid in water and B=0.1% formic acid in acetonitrile (for acidic work) or A=0.1% ammonium hydroxide in water and B=acetonitrile (for basic work). For acidic analysis the column used was a Waters Acquity HSS T3 (1.8 µm, 2.1×30 mm), for basic analysis the column used was a Waters Acquity BEH C18 (1.7 µm, 2.1×30 mm); The reported molecular ion corresponds to the [M+H]+ unless otherwise specified; for molecules with multiple isotopic patterns (Br, Cl, etc.) the reported value is the one obtained with highest intensity unless otherwise specified.

(xii) the following abbreviations have been used:
ACN Acetonitrile
BHA Benzhydrylamine
BOC tert-butyloxycarbonyl
CoA Certificate of Analysis
DGA Diglycolic acid
DIPEA Diisopropylethylamine
DMF Dimethylformamide
DMSO Dimethylsulfoxide
FBA 4-Fluorobenzoic acid
Glu Glutaric
HP-β-CD hydroxypropyl-beta-cyclodextrin
MeOH Methanol
MIDA Methyliminodiacetic acid
MSA Methanesulfonic acid
MTBE Methyl tert-butyl ether
MW Molecular Weight
NMM N-Methylmorpholine
PBS Phosphate buffered saline
PEG Polyethylene Glycol PTFE Polytetrafluoroethylene PyBOP Benzotriazol-1-yl-oxytripyrrolidinophosphonium hexafluorophosphate QS/qs Quantum sufficit (the amount which is needed)

SBE-β-CD Sulfobutyl ether beta-cyclodextrin (Captisol®)

TDA Thiodiglycolic acid

TFA Trifluoroacetic acid

WFI Water for injection WFI

As used in the Examples, the term "BHALys" refers to 2,6-diamino-N-benzhydrylhexanamide linked to lysine. BHA has the structure:

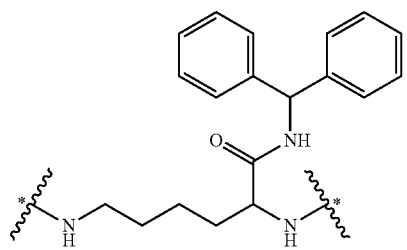 [SMILES: *NCCCCC(N*)C(=O)NC(c1ccccc1)c1ccccc1]

wherein * indicates a covalent attachment to the lysine building blocks. The term "Lys" refers to the building units of the dendrimer and has the structure:

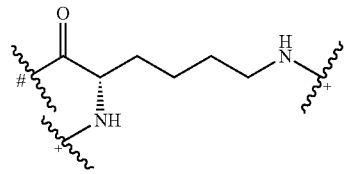 [SMILES: *NCCCC[C@H](N*)C(*)=O]

in which # indicates covalent attachment to an amine moiety of BHALys or an amino moiety of a Lys building unit, and + indicates a covalent attachment to a carbonyl moiety of a Lys building unit or a covalent attachment to PEG or the linker attached to the active agent.

For convenience, only the surface generation of building units in the dendrimers of the Examples is included in the name of the dendrimer. In addition, the symbol ‡ in the name refers to the theoretical number of ε-amino groups available for conjugation to PEG and the symbol † in the name refers to the theoretical number of α-amino groups on the dendrimer available for conjugation to the linker attached to the active agent, respectively. As an example, the name "BHALys[Lys]$_{32†}$[α-TDA-Compound A]$_{32}$[ε-PEG$_{2100, 2200}$]$_{32‡}$" refers to a fifth generation dendrimer with the BHALys core, Lys building units in the surface (fifth) layer, approximately 32 Compound A conjugated to the α-amino groups of the Lys surface building units with thiodiacetic acid linkers, approximately 32 PEG groups with and average molecular weight of between 2100 and 2200 conjugated to the ε-amino groups of the Lys surface building units.

Example 1: Physicochemical Properties of to 4-(4-((R)-(4'-chlorobiphenyl-2-yl)(hydroxy)methyl)piperidin-1-yl)-N-(4-((R)-4-((2-hydroxyethyl)(methyl)amino)-1-(phenylthio)butan-2-ylamino)-3-(trifluoromethylsulfonyl)phenylsulfonyl)benzamide (Compound A)

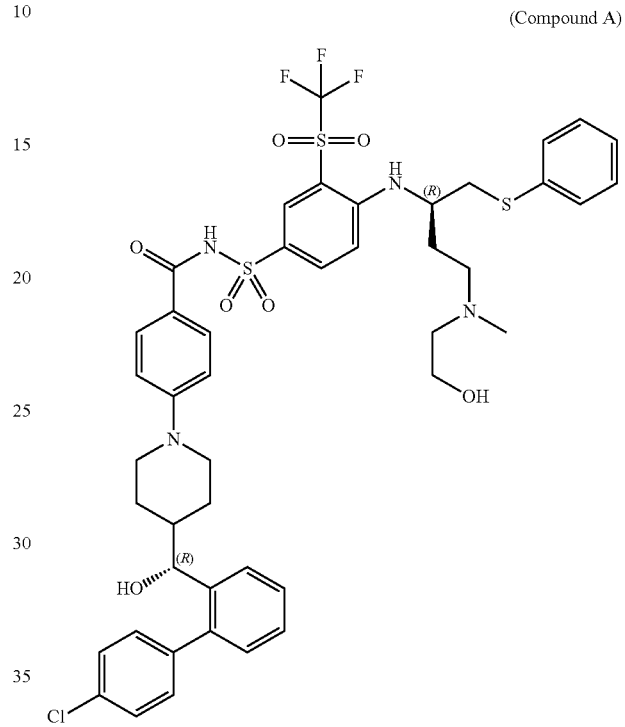

(Compound A)

The synthesis of Compound A is found in U.S. Pat. No. 9,018,381.

Preparation of Compound A, Form B

Figure 2:
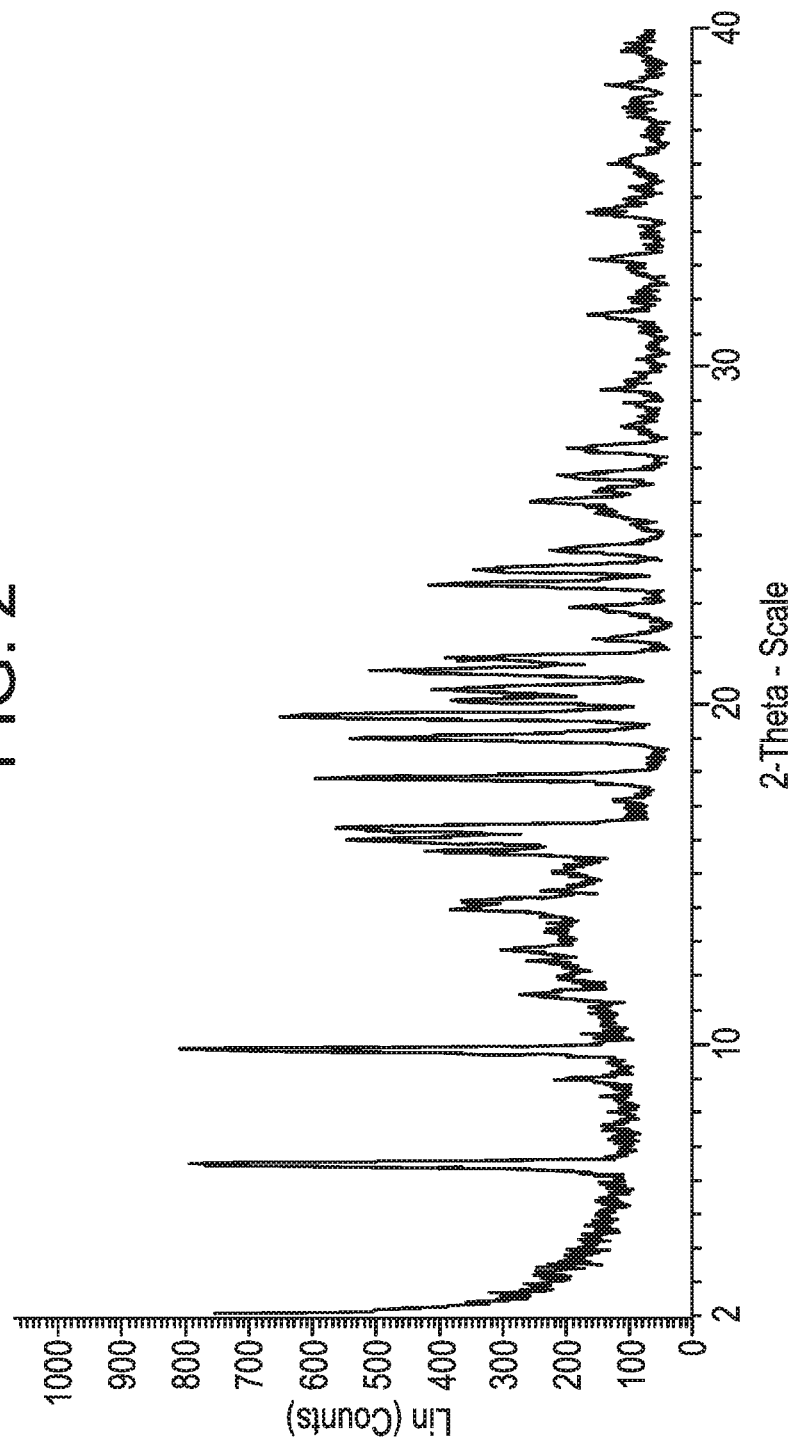
FIG. 2 is an XRPD diffractogram for Form B of Compound A.

A suspension of crude Compound A (900 g) in DMSO (450 mL) and Ethanol (2250 ml) was stirred at 50° C. until a solution was achieved. The solution was passed through an in-line filter and heated to 60° C. Ethanol anti-solvent (2700 mL) was added to the solution over 35 minutes. Once the addition was complete the solution was cooled to 50° C., seeded with Compound A Form B (18 g) and agitated at 50° C. for 18 hours. The batch was then cooled to 20° C. on a linear ramp over 17.5 hours and held at 20° C. for a further 4.5 hours. The resulting solid was collected by filtration, washed with 2 portions of ethanol (1350 mL and 1350 mL). The resulting solid was dried in the oven (40° C., 5 mbar) to afford Compound A Form B (764 g, 81.49% yield). An XRPD Diffractogram for Compound A form B is provided in FIG. 2.

Solubility

Compound A has very low aqueous solubility as illustrated by data shown in Table 1. The solubility is low across the physiological pH range of pH 4-9. Form B is the most stable crystalline form of Compound A found to date and this form has poor wetting and dissolution characteristics. Salt screening was undertaken with the aim of finding a salt with improved dissolution kinetics, but a crystalline salt form was not identified.

The solubility of Compound A (Form B) was determined in water and propylene glycol. The solubility was determined using a shake flask method allowing the drug substance to equilibrate at room temperature for 24 hours, with some sedimentation in the vials showing presence of excess drug substance. The solutions were centrifuged using ultra centrifuge for 30 min at 40,000 rpm, supernatant were transferred to a new centrifuge tube and centrifuged for another 30 min at 40,000 rpm. The propylene glycol supernatant was then assayed using a UV-HPLC method. The water supernatant was ultra-centrifuged for a third time before assay. The results are reported in Table 1.

TABLE 1

Compound A crystalline Form B Solubility Data

| Solvent | Final pH | Solubility (mg/mL) |
|---|---|---|
| Water | 8.7 | <1 μg/ml* |
| Propylene Glycol | — | 6.12 mg/ml |

*Accurately measuring the solubility of Compound A in water is a significant challenge due to the following reasons: 1) The solubility is extremely low and when solutions are transferred from centrifuge vials into pipettes/LC vials etc. it is likely that some Compound A is lost due to binding to glass/plastic components. 2) Compound A is light sensitive and at such a low concentration the rate of light degradation becomes significant. Although efforts were made to minimize the amount of light the aqueous solution was exposed to, a small amount of exposure to light could significantly affect the solubility measurement.

Log D

Lipophilicity (Log D) of Compound A was measured using octanol/water shake-flask principles. The aqueous solution used was a 10 mM sodium phosphate buffer with pH adjusted to 7.4. Octanol was used as the organic partitioning layer. The method was validated for log D ranging from −2 to 5.0. The measured Log D value for Compound A was >3.5, indicating that it is a highly lipophilic molecule.

Caco2 Permeability

Caco-2 cell lines are derived from a human colorectal adenocarcinoma. Seeding under conventional cell culture conditions, differentiation and the formation of tight cell monolayers (on porous polycarbonate membranes) allows Caco-2 cells to resemble those of the intestinal (absorptive) enterocytes. Caco-2 cells express a range of efflux transporters, including human multidrug resistance 1 (hMDR1), human multidrug resistance-associated protein 2 (hMRP2) and human breast cancer resistance protein (hBCRP). Caco-2 cells are used in a 96-well format to assess permeability and efflux of new chemical entities. The data was generated via routine LC-MS/MS, however no value was reported. Poor recovery was likely due to solubility limitations of Compound A.

Plasma Protein Binding:

Protein binding of Compound A (prepared as DMSO stock solutions and spiked into plasma at nominal incubation concentrations of 0.1, 1, 10 and 100 μmol/L) was evaluated in pooled frozen plasma obtained from male CD-1 mice, male Han Wistar rats, female New Zealand White rabbits, male Beagle dogs and male humans in triplicate using Equilibrium Dialysis RED device methodology (Waters N J et al., Validation of a Rapid Equilibrium Dialysis Approach for the Measurement of Plasma Protein Binding, Journal of Pharmaceutical Sciences; 2008; Volume 97; Issue 10; Pages 4586-4595, 2008). Incubations were conducted over an equilibration time of 30 hours at 37° C. Sample analysis was by HPLC-MS/MS and employed an [$^{13}$C, $^{2}$H$_7$] Compound A internal standard using the following bioanalytical method:

LC-MS/MS Apparatus

UHPLC: Shimadzu CC-30A

MS/MS instrument: API 4000 (AB Sciex, USA).

LC-MS/MS Conditions

1. Chromatographic Conditions

Column: Phenomenex Kinetex 1.7μ C18 (2.1×30 mm)

Mobile phase: 0.1% formic acid in acetonitrile (B) and 0.1% formic acid in water (A)

TABLE 2

Gradient of formic acid in water

| | Time (min) | | | | | |
|---|---|---|---|---|---|---|
| | 0 | 0.5 | 1.2 | 2.0 | 2.1 | 2.5 |
| % B | 5 | 5 | 100 | 100 | 5 | 5 |

Elution rate: 0.6 mL/min,
Column temperature: Room temperature,
Injection volume: 10 μL Mass Conditions Ion source: Turbo spray Ionization mode: ESI Scan type: MRM Other Parameters

TABLE 3

| | Q1 | Q3 | DP (v) | EP (v) | CE (v) | CXP (v) |
|---|---|---|---|---|---|---|
| Compound A | 945.2 | 404.3 | 120 | 10 | 55 | 12 |
| [$^{13}$C,$^{2}$H$_7$] Compound A | 953.2 | 404.3 | 120 | 10 | 55 | 12 |

The percentage unbound Compound A in mouse, rabbit and human was found to be 0.00235%, 0.00153% and 0.00196% respectively at a Compound A concentration of 100 μmol/L. The % unbound Compound A in rat and dog plasma was <0.001% at a Compound A concentration of 100 μmol/L however detectable levels of Compound A were observed in the buffer component, but these were not quantifiable (<1 nmol/L). At Compound A concentrations of 0.1, 1 and 10 μmol/L the % unbound Compound A could not be determined in any species as concentrations in the buffer component were not quantifiable (<1 nmol/L). This data illustrates that Compound A is extremely highly bound to mouse, rat, rabbit, dog and human plasma proteins.

Example 2: Preparation of Formulations of Compound A

The compositions of the formulations prepared are shown in Table 4 (10 mL scale) and Table 5 (larger scale, 500 and 1200 mL scale). The concentrations shown are the concentration of Compound A in each of the formulations.

TABLE 4

Example Formulation Compositions for 10 mL scale

| Ingredients | 30% w/v HP-β-CD pH 4 (1 mg/mL) | 30% w/v HP-β-CD pH 4 (0.4 mg/mL) | 5% w/v Cremophor EL ph 4 (2 mg/mL) | 0.5% w/v Tween 80 pH 9 (1 mg/mL) | 0.5% w/v Tween 80 pH 9 (0.4 mg/mL) | 10.6% w/v Captisol pH 9 (1 mg/mL) | 10.2% w/v Captisol pH 9 (0.4 mg/mL) |
|---|---|---|---|---|---|---|---|
| WFI | qs 10 mL | qs 10 mL | qs 10 mL | qs 10 mL (with saline) | qs 10 mL (with saline) | qs 10 mL | qs 10 mL |
| HP-β-CD (excipient) | 3.0 g | 3.0 g | — | — | — | — | — |
| Captisol (excipient) | — | — | — | — | — | 1.06 g | 1.02 g |
| Cremophor EL (excipient) | — | — | 0.5 g | — | — | — | — |
| Tween 80 (excipient) | — | — | — | 0.05 g | 0.05 g | — | — |
| PEG 400 (excipient) | — | — | 1.5 mL | — | — | — | — |
| Compound A (active) | 0.01 g | 0.004 g | 0.02 g | 0.01 g | 0.004 g | 0.01 g | 0.004 g |
| 1M Meglumine (pH modifier) | — | — | — | 0.04 mL (4 molar equiv. to active) | 0.04 mL (4 molar equiv. to active) | 0.02 mL (2 molar equiv. to active) | 0.02 mL (2 molar equiv. to active) |
| 1M MSA (pH modifier) | enough to modify the pH to 4 | enough to modify the pH to 4 | 0.024 mL (and enough to modify final pH to 4) | — | — | — | — |
| 1M HCl (pH modifier) | — | — | — | enough to modify the pH to 9 | enough to modify the pH to 9 | enough to modify the pH to 9 | enough to modify the pH to 9 |
| 1M NaOH (pH modifier) | enough to modify the pH to 4 (if required) | enough to modify the pH to 4 (if required) | enough to modify the pH to 4 (if required) | — | — | — | — |
| Ethanol (co-solvent) | — | — | 0.5 mL | — | — | — | — |

Method of Preparation for 30% w/v HP-β-CD Formulations (Used as "Vehicle 1" in Example 3)

30% w/v HP-β-CD vehicle was prepared. 3 g HP-β-CD (Roquette Kleptose, parenteral grade) was weighed into a 10 mL volumetric flask and 8 mL WFI added and stirred (or sonicated) to dissolve. Once dissolved the volume was made up to 10 mL with WFI.

The appropriate amount of Compound A was weighed into a 10 mL volumetric flask. 8 mL of 30% w/v HP-β-CD vehicle was then added and the formulation stirred. 1M MSA was added dropwise until the pH was reduced to about 2. The formulation was then stirred until the compound dissolved entirely. The pH was measured and adjusted to pH 4, dropwise using 1M MSA or NaOH. The formulation was then stirred to make sure a clear solution (with possible haze) was obtained. The volume was then made up to 10 mL with 30% w/v HP-β-CD vehicle and stirred. The final pH was measured and recorded and the formulation filtered through a 0.22 uM filter prior to administration. Other formulation strengths were prepared by diluting the Compound A in 30% w/v HP-β-CD with an appropriate amount of 30% w/v HP-β-CD vehicle.

Method of Preparation for 10.6% w/v Captisol Formulation (Used as "Vehicle 2" in Example 3)

20% w/v Captisol vehicle was prepared. 2 g of Captisol (research grade, Ligand) was weighed into a 10 mL volumetric flask and 8 mL WFI added and stirred (or sonicated) to dissolve. Once dissolved the volume was made up to 10 mL with WFI. The 7.5% w/v Captisol vehicle was prepared by diluting the 20% w/v Captisol vehicle 3.75 mL to 10 mL with WFI. The 10.0% w/v Captisol vehicle was prepared by diluting the 20% w/v Captisol vehicle 5 mL to 10 mL with WFI.

A stock solution of 4 mg/mL Compound A in 20% w/v Captisol, pH 9 was prepared. 0.04 g Compound A was weighed into a volumetric flask. 8 mL of 20% w/v Captisol vehicle was then added and the formulation stirred. The relevant volume of 1M meglumine was added. The formulation was then stirred until the compound dissolved entirely. The pH was then measured and adjusted to pH 9, dropwise using 1M HCl. The volume was then made up to 10 mL with 20% w/v Captisol vehicle and stirred. The final pH was measured and recorded, and the formulation filtered through a 0.22 uM filter.

The 1 mg/mL Compound A in 10.6% w/v Captisol formulation (as used in Example 3) was made by diluting the stock 4 mg/mL Compound A in 20% w/v Captisol 2.5 mL to 10 mL with 7.5% w/v Captisol vehicle.

Method of Preparation for 0.5% w/v Tween 80 Formulation (Used as "Vehicle 3" in Example 3)

5% w/v Tween 80 vehicle was prepared. 0.5 g of Tween 80 (super-refined, Fisher Scientific) was weighed into a 10 mL volumetric flask and 8 mL WFI was added and stirred (or sonicated) to dissolve. Once dissolved the volume was made up to 10 mL with WFI. The 0.5% w/v Tween 80 vehicle was prepared by diluting the 5% w/v Tween vehicle 1 mL to 10 mL with saline.

A stock solution of 10 mg/mL Compound A in 5% w/v Tween 80, pH 9 was prepared. 0.1 g Compound A was weighed into a volumetric flask. 8 mL of the 5% w/v Tween 80 vehicle was then added and the formulation stirred. The relevant volume of 1M meglumine was added. The formulation was then stirred until the compound dissolved entirely. The pH was then measured and adjusted to pH 9, dropwise using 1M HCl. The volume was then made up to 10 mL with the 5% w/v Tween 80 vehicle and stirred. The final pH was measured and recorded, and the formulation filtered through a 0.22 uM filter.

The 1 mg/mL Compound A in 0.5% w/v Tween formulation was made by diluting the stock 10 mg/mL Compound A in 5% w/v Tween 1 mL to 10 mL with saline. Preparation of 0.4 mg/mL Compound A in 0.5% w/v Tween was made by diluting the 1 mg/mL Compound A in 0.5% w/v Tween formulation 4 mL to 10 mL with 0.5% w/v Tween 80 vehicle.

Method of Preparation for 5% w/v Cremophor EL Formulation (Used as "Vehicle 4" in Example 3)

20% w/v Cremophor vehicle was prepared. 2 g of Cremophor EL (Kolliphor EL®, BASF) (viscous liquid) was weighed into a 10 mL volumetric flask. 5 mL of WFI was then added and sonicated or stirred to dissolve. Once dissolved, the volume was made up to volume with WFI.

0.02 g Compound A was weighed into a 10 mL volumetric flask. 0.5 mL of ethanol, 1.5 mL PEG 400 (Fischer Scientific) and 0.024 mL of 1M MSA were added. The formulation was then stirred until the drug dissolved entirely. The pH was measured and adjusted to pH 4.0 with concentrated 1M NaOH or 1M MSA if required. 2.5 mL of 20% w/v Cremophor vehicle was added and the volume was then made up to 10 mL with WFI to make a clear solution. The formulation was filtered through a 0.22 uM filter prior to administration.

Method of Preparation for 10.2% w/v Captisol Formulation

Preparation of 0.4 mg/mL Compound A in 10.2% w/v Captisol was made by diluting a 1 mg/mL Compound A in 10.6% w/v Captisol formulation (see the preceding section for method of preparation) 4 mL to 10 mL with 10.0% w/v Captisol vehicle.

and the washings were added to the 1 L beaker to achieve 95% of the final target volume. The suspension was protected from light and stirred overnight, resulting in a yellow, slightly hazy solution. The hazy solution was pH adjusted to 9.5 using 1M meglumine, made up to the target volume using 28% w/v HP-β-CD vehicle and stirred for 30 minutes. The final pH was measured and recorded, and the formulation filtered through a 0.22 uM filter prior to filling into clean, sterile vials that were stoppered and crimped.

Method of Preparation for 14% w/v Captisol Formulation

The preparation was carried out in a clean room and clean, sterile equipment was used. A concentrated 42% w/v Captisol vehicle was first prepared to aid dissolution of Compound A. (later in the preparation the formulation was diluted with WFI to produce a final formulation of 14% w/v Captisol.) 579.86 g WFI was weighed into a 3 L beaker, 352.94 g Captisol was added whilst stirring and then the mixture was stirred with a large vortex until the Captisol had fully dissolved.

233.2 g 42% w/v Captisol was added to a 600 mL beaker. Subsequently 1.365 g of 1M meglumine was added whilst stirring, followed by 0.60 g of Compound A whilst stirring. The suspension was homogenised for 30 minutes, resulting in a yellow, slightly hazy solution. The homogenizer head was washed with 42% w/v Captisol. The homogenized solution and washings were transferred to a 2 L beaker and made up to a total volume of 400 mL with 42% w/v Captisol. The solution was protected from light and stirred overnight. The slightly hazy solution was diluted with 740 g WFI to 95% of the final target volume and stirred for 30 minutes. The solution was pH adjusted to 9.5 using 1M meglumine, made up to the target volume using WFI and stirred for 30 minutes. The final pH was measured and recorded, and the formulation filtered through a 0.22 uM filter prior to filling into clean, sterile vials that were stoppered and crimped.

Stability of Captisol and HP-β-CD Formulations

The physical stabilities of the 0.5 mg/mL Compound A/14% w/v Captisol formulation and the 5.0 mg/mL Com-

TABLE 5

Formulation Compositions for large scale

| Ingredients | 28% w/v HP-β-CD formulation pH 9.5 (5 mg/mL Compound A) | 14% w/v Captisol formulation pH 9.5 (0.5 mg/mL Compound A) |
| --- | --- | --- |
| WFI | qs 500 mL | qs 1200 mL |
| HP-β-CD (excipient) | 140.0 g | — |
| Captisol (excipient) | — | 168.0 g |
| Compound A (active) | 2.5 g | 0.60 g |
| 1M Meglumine (pH modifier) | 5.42 mL (2 molar equiv. to active) and enough to modify final pH to 9.5 | 1.30 mL (2 molar equiv. to active) and enough to modify final pH to 9.5 |
| 1M HCl (pH modifier) | enough to modify the pH to 9.5 | enough to modify the pH to 9.5 |

Method of Preparation for 28% w/v HP-β-CD Formulation

The preparation was carried out in a clean room and clean, sterile equipment was used. 28% w/v HP-β-CD vehicle was prepared. 145.60 g HP-β-CD was weighed into a 2 L beaker and 412.88 g WFI was added and stirred until the HP-β-CD had fully dissolved.

279.2 g of 28% w/v HP-β-CD was added to a 1 L beaker. Subsequently 5.689 g of 1 M meglumine was added whilst stirring, followed by 2.50 g of Compound A whilst stirring. The suspension was homogenized for 30 minutes. The homogenizer head was then washed with 28% w/v HP-β-CD pound A/28% w/v HP-β-CD formulation were assessed. A very small amount of precipitate, just visible to the naked eye, formed in each formulation within 24 hours of storage at ambient temperature. For the Captisol-based formulation it was noted that the precipitate formed rapidly when the formulation system was perturbed (e.g., filtered), but the precipitate did not continue to grow at a rapid rate when the formulation was stored at 5° C. and 25° C. for 6 months.

Chemical stability data indicates that a Captisol-based formulation would need to be stored at 5° C., or frozen to provide an acceptable shelf life (>6 months) for clinical studies.

Due to the low solubility of Compound A in aqueous vehicles, a high level of Captisol or HP-β-CD, in addition to a high pH and a high infusion volume, would be needed to solubilize the doses of Compound A required to conduct clinical safety studies.

Example 3: Xenograft Efficacy Study for Formulations of Compound A

Figure 3B:
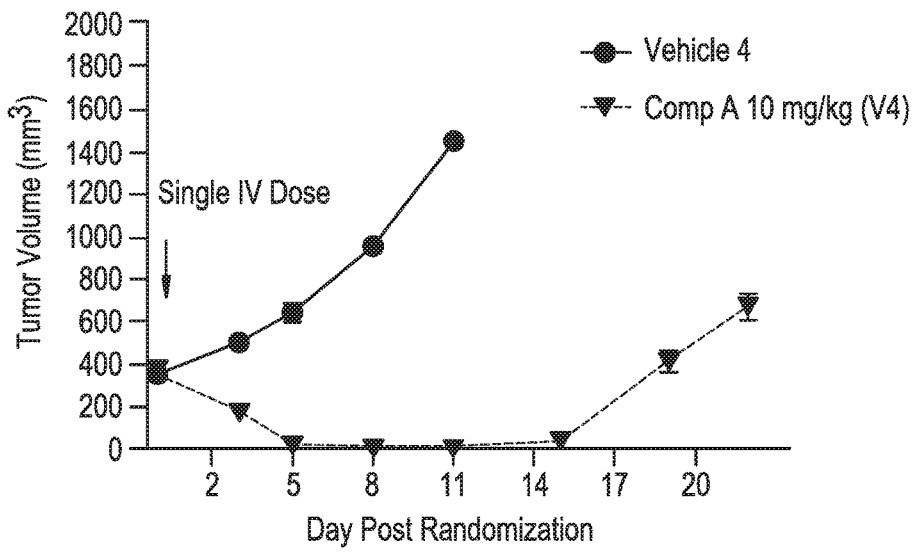
FIG. 3B displays an Acute Lymphoblastic Leukemia (ALL) Xenograft model in SCID mice using human acute lymphoblastic leukemia cells (RS4:11) for a formulation of Compound A with Cremophor. The efficacy evaluation of Compound A formulated with Cremophor (V4) compared to the corresponding vehicle; Vehicle 4 (V4, 5% w/v Cremophor EL, pH4) is shown. See Example 2.

The formulations used in the xenograft efficacy were prepared according to the procedures of Example 2 above. Efficacy Evaluation of Compound a in RS4:11 Acute Lymphoblastic Leukemia (ALL) Xenograft Model in Mice Human acute lymphoblastic leukemia cells (RS4;11) were used to test the activity of Compound A in different formulations (FIG. 3A). RS4;11 cells were injected via the subcutaneous route into the right flank of female CB-17/ICr-Prkdcscid/IcrIcoCrI SCID mice (Charles River Laboratories) at 5×10$^6$ cells/mouse. When tumors reached a target size of 300-400 mm$^3$, mice were randomized to vehicle control; Vehicle 1 (30% HP-β-CD, pH 4), Vehicle 2 (10.6% Captisol, pH 9), Vehicle 3 (0.5% Tween, pH 9) or a treatment of Compound A (2 and 5 mg/kg formulated in Vehicle 1, 2 or 3). Additionally, in a separate experiment, the activity of Compound A in a Cremophor formulation, Vehicle 4 was investigated (FIG. 3B). All formulations were administered as single IV bolus. To assess efficacy, tumor volume was measured twice weekly and calculated as: Tumor Volume=(A×B$^2$)/2 where A and B are the tumor length and width (in mm), respectively for up to a 4 week period post-dosing.

Figure 4:
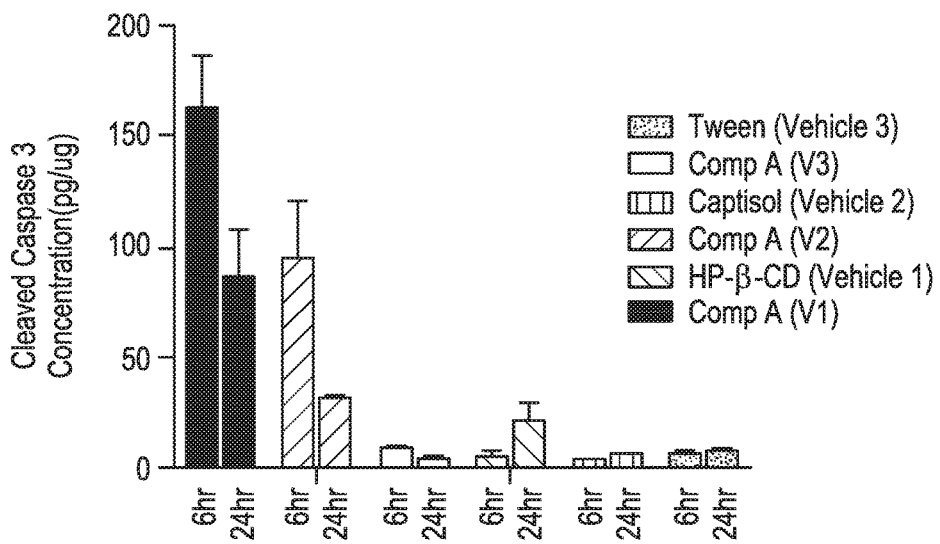
FIG. 4 displays the cell death (apoptosis) at 6 h and 24 hr post a single dose of Compound A formulated in each of HP-β-CD (V1), Captisol (V2) and Tween (V3) compared to the corresponding vehicles; Vehicle 1 (V1, 30% HP-β-CD, pH4), Vehicle 2 (V2, 10.6% Captisol, pH9) and Vehicle 3 (V3, 0.5% Tween, pH9). Cleaved Caspase 3 (CC3) response was used as a measure of cell death and was determined using the Cell Signaling Pathscan ELISA Kit. See Example 2.

To assess the single dose pharmacodynamic (PD) response (FIG. 4), the mice were culled at appropriate time points, tumors removed, and half of the tumor processed and analyzed for Cleaved Caspase 3 response (CC3) as a marker of apoptosis induction using the Cell Signaling Pathscan ELISA Kit. To assess single dose tumor exposure (PK) (FIG. 5), the remaining half of the tumor was processed and drug concentration was measured.

Figure 5:
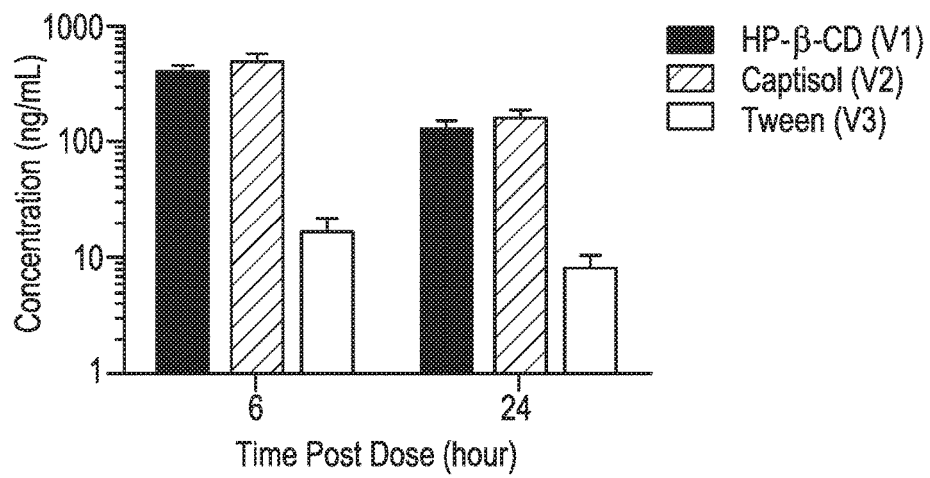
FIG. 5 displays the single dose tumor exposure for Compound A formulated in each of HP-β-CD (V1), Captisol (V2) and Tween (V3). Concentrations of Compound A in the tumor after 6 h and 24 hrs post a single dose were determined using LC-MS/MS. See Example 2.

Captisol and HP-β-CD formulations showed statistically equivalent efficacy over 33 days. The Tween 80 formulation on the other hand, showed no/minimal efficacy (FIG. 3A). Both Captisol and HP-β-CD formulations showed similar tumor exposures at 6 and 24 hrs (FIG. 5). The HP-β-CD formulation however triggered more cell death, as measured by the level of Cleaved Caspase 3 response, than the Captisol formulation (FIG. 4) although efficacy and exposure appeared equivalent. The Tween 80 formulation showed lower tumor exposure and no evidence of Cleaved Caspase 3 induction. In summary, efficacy of Compound A is dependent on the presence of cyclodextrin, either HP-β-CD or Captisol. Reduced efficacy was observed with other vehicles (e.g., Tween or Cremophor).
Efficacy Evaluation of Compound a (HP-β-CD) at a Different Infusion Length in RS4:11 Acute Lymphoblastic Leukemia Xenograft Model in Rats Rag2-/- rats purchased from (SAGE) were inoculated with RS4;1 (10×10$^6$ cells/rat). When tumors grew to approximately 4500-6000 mm$^3$, rats were randomized to vehicle control (30% HP-β-CD) or Compound A 5 mg/kg in Vehicle 1) delivered as a single IV 30 min infusion (FIG. 6) and Vehicle control (30% HP-β-CD) or Compound A 5 mg/kg, 3 mg/kg and 1 mg/kg in Vehicle 1 delivered as a single IV 5 hr infusion (FIG. 7). The tumor sizes were measured twice a week and calculated as: Tumor Volume=(A×B$^2$)/2 where A and B are the tumor length and width (in mm), respectively.

Figure 6:
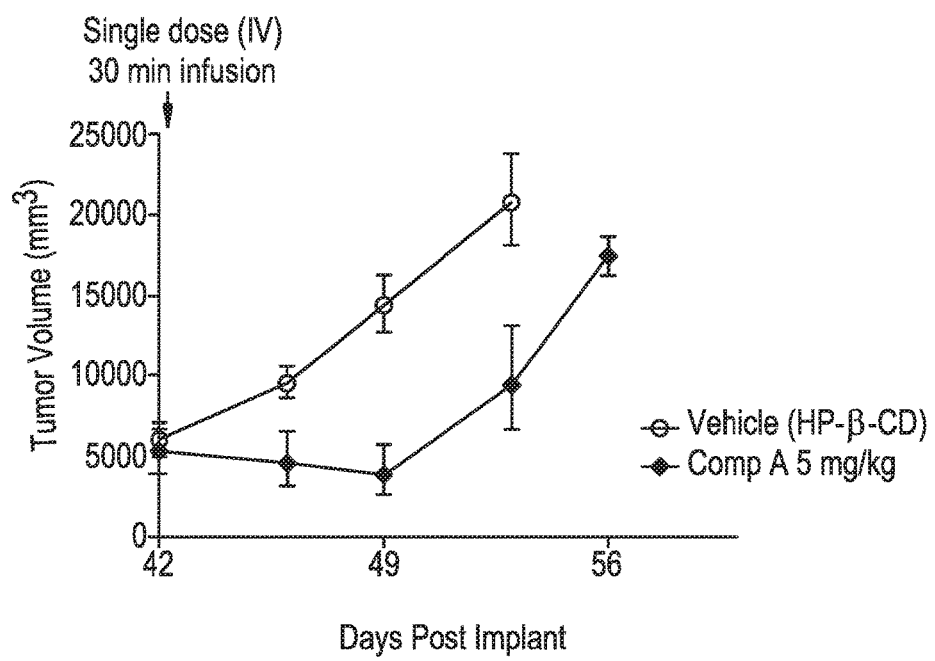
FIG. 6 displays an Acute Lymphoblastic Leukemia (ALL) Xenograft model in Rag2−/− rats using human acute lymphoblastic leukemia cells (RS4:11). When tumors grew to approximately 4500-6000 mm$^3$ rat were randomized to Vehicle 1 (30% HP-β-CD, pH4) or Compound A 5 mg/kg IV 30 min infusion once. The efficacy evaluation of Compound A formulated with 30% HP-β-CD (V1) compared to the corresponding vehicle (V1) is shown. See Example 2.
Figure 7:
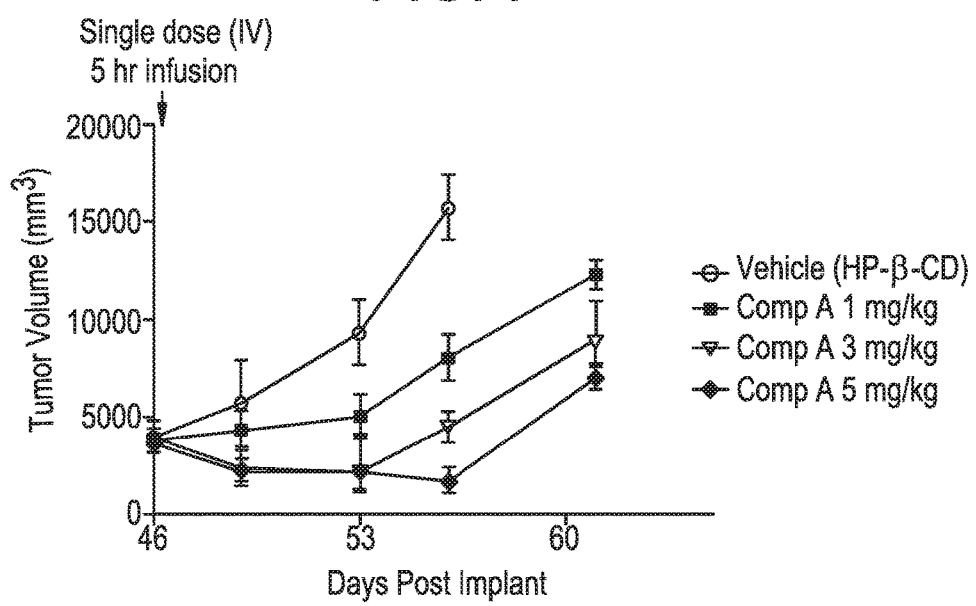
FIG. 7 displays an Acute Lymphoblastic Leukemia (ALL) Xenograft model in Rag2−/− rats using human acute lymphoblastic leukemia cells (RS4:11). When tumors grew to approximately 4500-6000 mm$^3$ rat were randomized to Vehicle 1 (30% HP-β-CD, pH4) or Compound A 5 mg/kg, Compound A 3 mg/kg and Compound A 1 mg/kg, IV 30 min infusion once. The dose response efficacy evaluation of Compound A formulated with 30% HP-β-CD (V1) at 5 mg/kg, 3 mg/kg and 1 mg/kg compared to the corresponding vehicle (V1) is shown. See Example 2.

The results are shown in FIGS. 6 and 7. Compound A at 5 mg/kg at 30 min infusion inhibited tumor growth for ~9 days post a single treatment compared to vehicle. Comparable efficacy was observed when the infusion was prolonged to 5 hrs. In summary, prolonging the infusion time doesn't affect the activity of Compound A in this formulation.

Example 4: Preparation and Characterization of BHALys[Lys]$_{32}$[α-NH$_2$TFA]$_{32}$[ε-PEG~2000]$_{32‡}$ Note.

32‡ relates to the theoretical number of ε-amino groups available for substitution with PEG$_{~2000}$. The actual mean number of PEG$_{~200}$ groups attached to the BHALys[Lys]$_{32}$ was determined experimentally by $^1$H NMR (see below section in the present Example entitled Characterization of BHALys[Lys]$_{32}$[α-NH$_2$-TFA]$_{32}$[ε-PEG~2000]$_{32‡}$).
Preparation of BHALys[Lys]$_{32}$[α-NH$_2$TFA]$_{32}$[ε-PEG~2000]$_{32‡}$
BHALys[Boc]$_2$ Solid α,ε-(t-Boc)$_2$-(L)-lysine p-nitrophenol ester (2.787 kg, 5.96 mol) was added to a solution of aminodiphenylmethane (benzhydrylamine) (0.99 kg, 5.4 mol) in anhydrous acetonitrile (4.0 L), DMF (1.0 L) and triethylamine (1.09 kg) over a period of 15 min. The reaction mixture was agitated at 20° C. overnight. The reaction mixture was then warmed to 35° C. and aqueous sodium hydroxide (0.5 N, 10 L) was added slowly over 30 min. The mixture was stirred for an additional 30 min then filtered. The solid cake was washed with water and dried to a constant weight (2.76 kg, 5.4 mol) in 100% yield. $^1$H NMR (CD$_3$OD) δ 7.3 (m, 10H, Ph Calc 10H); 6.2 (s, 1H, CH-Ph$_2$ Calc 1H); 4.08 (m, α-CH, 1H), 3.18 (br, ε-CH$_2$) and 2.99 (m, ε-CH$_2$ 2H); 1.7-1.2 (br, β,γ,δ-CH$_2$) and 1.43 (s, tBu) total for β,γ,δ-CH$_2$ and tBu 25H Calc 24H. MS (ESI +ve) found 534.2 [M+Na]$^+$ calc for C$_{29}$H$_{41}$N$_3$O$_5$Na [M+Na]$^+$ 534.7.
BHALys[HCl]$_2$ A solution of concentrated HCl (1.5 L) in methanol (1.5 L) was added slowly, in three portions, to a stirred suspension of BHALys[Boc]$_2$ (780.5 g, 1.52 mol) in methanol (1.5 L) at a rate to minimize excessive frothing. The reaction mixture was stirred for an additional 30 min, then concentrated under vacuum at 35° C. The residue was taken up in water (3.4 L) and concentrated under vacuum at 35° C. twice, then stored under vacuum overnight. Acetonitrile (3.4 L) was then added and the residue was again concentrated under vacuum at 35° C. to give BHALys[HCl]$_2$ as a white solid (586 g, 1.52 mol) in 100% yield. $^1$H NMR (D$_2$O) δ 7.23 (br m, 10H, Ph Calc 10H); 5.99 (s, 1H, CH-Ph$_2$ Calc 1H); 3.92 (t, J=6.5 Hz, α-CH, 1H, Calc 1H); 2.71 (t, J=7.8 Hz, ε-CH$_2$, 2H, Calc 2H); 1.78 (m, β,γ,δ-CH$_2$, 2H), 1.47 (m, β,γ,δ-CH$_2$, 2H), and 1.17 (m, β,γ,δ-CH$_2$, 2H, total 6H Calc 6H). MS (ESI +ve) found 312 [M+H]+ calc for C$_{19}$H$_{26}$N$_3$O [M+H]+ 312.
BHALys[Lys]$_2$[Boc]$_4$ To a suspension of BHALys[HCl]$_2$ (586 g, 1.52 mmol) in anhydrous DMF (3.8 L) was added triethylamine (1.08 kg) slowly to maintain the reaction temperature below 30° C. Solid α,ε-(t-Boc)$_2$-(L)-lysine p-nitrophenol ester (1.49 kg) was added in three portions, slowly and with stirring for 2 hours between additions. The reaction was allowed to stir overnight. An aqueous solution of sodium hydroxide (0.5 M, 17 L) was added slowly to the well stirred mixture, and stirring was maintained until the solid precipitate was freely moving. The precipitate was collected by filtration, and the solid cake was washed well with water (2×4 L) then acetone/water (1:4, 2×4 L). The solid was slurried again with water then filtered and dried under vacuum overnight to give BHALys [Lys]$_2$[Boc]$_4$ (1.51 kg) in 100% yield. $^1$H NMR (CD$_3$OD) δ 7.3 (m, 10H, Ph Calc 10H); 6.2 (s, 1H, CH-Ph$_2$ Calc 1H); 4.21 (m, α-CH), 4.02 (m, α-CH) and 3.93 (m, α-CH, total 3H, Calc 3H); 3.15 (m, ε-CH$_2$) and 3.00 (m, ε-CH$_2$ total 6H, Calc 6H); 1.7-1.3 (br, β,γ,δ-CH$_2$) and 1.43 (s, tBu) total for β,γ,δ-CH$_2$ and tBu 57H, Calc 54H. MS (ESI +ve) found 868.6 [M-Boc]$^+$; 990.7 [M+Na]$^+$ calc for C$_{51}$H$_{81}$N$_7$O$_{11}$Na [M+Na]+ 991.1.

BHALys[Lys]$_2$[HCl]$_4$

BHALys[Lys]$_2$[Boc]$_4$ (1.41 kg, 1.46 mol) was suspended in methanol (1.7 L) with agitation at 35° C. Hydrochloric acid (1.7 L) was mixed with methanol (1.7 L), and the resulting solution was added in four portions to the dendrimer suspension and left to stir for 30 min. The solvent was removed under reduced pressure and worked up with two successive water (3.5 L) strips followed by two successive acetonitrile (4 L) strips to give BHALys[Lys]$_2$[HCl]$_4$ (1.05 Kg, 1.46 mmol) in 102% yield. $^1$H NMR (D$_2$O) δ 7.4 (br m, 10H, Ph Calc 10H); 6.14 (s, 1H, CH-Ph$_2$ Calc 1H); 4.47 (t, J=7.5 Hz, α-CH, 1H), 4.04 (t, J=6.5 Hz, α-CH, 1H), 3.91 (t, J=6.8 Hz, α-CH, 1H, total 3H, Calc 3H); 3.21 (t, J=7.4 Hz, ε-CH$_2$, 2H), 3.01 (t, J=7.8 Hz, ε-CH$_2$, 2H) and 2.74 (t, J=7.8 Hz, ε-CH$_2$, 2H, total 6H, Calc 6H); 1.88 (m, β,γ,δ-CH$_2$), 1.71 (m, β,γ,δ-CH$_2$), 1.57 (m, β,γ,δ-CH$_2$) and 1.35 (m, β,γ,δ-CH$_2$ total 19H, Calc 18H).

BHALys[Lys]$_4$[Boc]$_8$

BHALys[Lys]$_2$[HCl]$_4$ (1.05 Kg, 1.47 mol) was dissolved in DMF (5.6 L) and triethylamine (2.19 L). The α,ε-(t-Boc)$_2$-(L)-lysine p-nitrophenol ester (2.35 Kg, 5.03 mol) was added in three portions and the reaction stirred overnight at 25° C. A NaOH (0.5M, 22 L) solution was added and the resulting mixture filtered, washed with water (42 L) and then air dried. The solid was dried under vacuum at 45° C. to give BHALys [Lys]$_4$[Boc]$_8$ (2.09 Kg, 1.11 mol) in 76% yield. $^1$H NMR (CD$_3$OD) δ 7.3 (m, 10H, Ph Calc 10H); 6.2 (s, 1H, CH-Ph$_2$ Calc 1H); 4.43 (m, α-CH), 4.34 (m, α-CH), 4.25 (m, α-CH) and 3.98 (br, α-CH, total 7H, Calc 7H); 3.15 (br, ε-CH$_2$) and 3.02 (br, ε-CH$_2$ total 14H, Calc 14H); 1.9-1.2 (br, β,γ,δ-CH$_2$) and 1.44 (br s, tBu) total for β,γ,δ-CH$_2$ and tBu 122H, Calc 144H.

BHALys[Lys]$_4$[TFA]$_8$

To a stirred suspension of BHALys[Lys]$_4$[Boc]$_8$ (4 g, 2.13 mmol) in DCM (18 mL) was added TFA (13 mL) at 0° C. The solids dissolved, and the solution was stirred overnight under an atmosphere of argon. The solvents were removed under vacuum, and residual TFA was removed by trituration with diethyl ether (100 mL). The product was redissolved in water then freeze dried to give BHALys[Lys]$_4$[TFA]$_8$ as an off-white solid (4.27 g, 2.14 mmol) in 101% yield. $^1$H NMR (D$_2$O) δ 7.21 (br m, 10H, Ph Calc 10H); 5.91 (s, 1H, CH-Ph$_2$ Calc 1H); 4.17 (t, J=7.4 Hz, α-CH, 1H), 4.09 (t, J=7.1 Hz, α-CH, 1H), 4.02 (t, J=7.2 Hz, α-CH, 1H, 3.84 (t, J=6.5 Hz, α-CH, 2H), 3.73 (t, J=6.7 Hz, α-CH, 1H), 3.67 (t, J=6.7 Hz, α-CH, 1H, total 7H, Calc 7H); 3.0 (m, ε-CH$_2$), 2.93 (m, ε-CH$_2$) and 2.79 (b, ε-CH$_2$, total 15H, Calc 14H); 1.7 (br, β,γ,δ-CH$_2$), 1.5 (br, β,γ,δ-CH2), 1.57 (m, β,γ,δ-CH$_2$) and 1.25 (br, β,γ,δ-CH2 total 45H, Calc 42H). MS (ESI +ve) found 541.4 [M+2H]$^{2+}$; calc for C$_{55}$H$_{99}$N$_{15}$O$_7$ [M+2H]$^{2+}$ 541.2.

BHALys[Lys]$_8$[Boc]$_{16}$

A solution of α,ε-(t-Boc)$_2$-(L)-lysine p-nitrophenol ester (1.89 g, 4.05 mmol) in DMF (25 mL) was added to a solution of BHALys [Lys]$_4$[NH$_2$TFA]$_8$ (644 mg, 0.32 mmol) and triethylamine (0.72 mL, 5.2 mmol) in DMF (25 mL) and the reaction was left to stir overnight under an argon atmosphere. The reaction mixture was poured onto ice/water (500 mL) then filtered and the collected solid was dried overnight under vacuum. The dried solid was washed thoroughly with acetonitrile to give BHALys[Lys]$_8$[Boc]$_{16}$ as an off white solid (0.82 g, 0.22 mmol) in 68% yield. $^1$H NMR (CD$_3$OD) δ 7.3 (m, 1 OH, Ph Calc 1 OH); 6.2 (br s, 1H, CH-Ph$_2$ Calc 1H); 4.48 (br, α-CH), 4.30 (br, α-CH) and 4.05 (br, α-CH, total 16H Calc 15H); 3.18 (br, ε-CH$_2$) and 3.02 (m, ε-CH$_2$ total 31H, Calc 30H); 1.9-1.4 (br, β,γ,δ-CH$_2$) and 1.47 (br s, tBu) total for β,γ,δ-CH$_2$ and tBu 240H, Calc 234H. MS (ESI +ve) found 3509 [M+H-(Boc)$_2$]$^+$ calc for C$_{173}$H$_{306}$N$_{31}$O$_{43}$ [M+H-(Boc)$_2$]$^+$ 3508.5; 3408 [M+H-(Boc)$_3$]$^+$ calc for C$_{168}$H$_{298}$N$_{31}$O$_{41}$ [M+H-(Boc)$_3$]$^+$ 3408.4.

BHALys[Lys]$_8$[TFA]$_{16}$

A solution of TFA/DCM (1:1, 19 mL) was added slowly to a stirred suspension of BHALys[Lys]$_8$[Boc]$_{16}$ (800 mg, 0.22 mmol) in DCM (25 mL). The solids dissolved, and the solution was stirred overnight under an atmosphere of argon. The solvents were removed under vacuum, and residual TFA was removed by repetitive freeze drying of the residue, to give BHALys [Lys]$_8$[TFA]$_{16}$ as an off-white lyophylate (848 mg, 0.22 mmol) in 100% yield. $^1$H NMR (D$_2$O) δ 7.3 (br m, 10H, Ph Calc 10H); 6.08 (s, 1H, CH-Ph$_2$ Calc 1H); 4.3 (m, α-CH), 4.18 (m, α-CH), 4.0 (m, α-CH) and 3.89 (m, α-CH, total 16H, Calc 15H); 3.18 (br, ε-CH$_2$) and 2.94 (m, ε-CH$_2$ total 32H, Calc 30H); 1.9 (m, β,γ,δ-CH$_2$), 1.68 (m, β,γ,δ-CH$_2$) and 1.4 (m, β,γ,δ-CH$_2$ total 99H, Calc 90H). MS (ESI +ve) found 2106 [M+H]$^+$ calc for C$_{103}$H$_{194}$N$_{31}$O$_{15}$ [M+H]$^+$ 2106.9.

BHALys[Lys]$_{16}$[Boc]$_{32}$

A solution of α,ε-(t-Boc)$_2$-(L)-lysine p-nitrophenol ester (1.89 g, 4.05 mmol) in DMF (25 mL) was added to a solution of BHALys [Lys]$_8$[TFA]$_{16}$ (644 mg, 0.32 mmol) and triethylamine (0.72 mL, 5.2 mmol) in DMF (25 mL) and the reaction was left to stir overnight under an argon atmosphere. The reaction was poured onto ice/water (500 mL) then filtered and the collected solid was dried overnight under vacuum. The dried solid was washed thoroughly with acetonitrile to give BHALys[Lys]$_{16}$[Boc]$_{32}$ as an off white solid (0.82 g, 0.2 2 mmol) in 68% yield. $^1$H NMR (CD$_3$OD) δ 7.28 (m, 9H, Ph Calc 10H); 6.2 (br s, 1H, CH-Ph$_2$ Calc 1H); 4.53 (br, α-CH), 4.32 (br, α-CH) and 4.05 (br, α-CH, total 35H, Calc 31H); 3.18 (br, ε-CH$_2$) and 3.04 (m, ε-CH$_2$ total 67H, Calc 62H); 1.9-1.5 (br, β,γ,δ-CH$_2$) and 1.47 (br s, tBu) total for β,γ,δ-CH$_2$ and tBu 474H Calc, 474H. MS (ESI +ve) found 6963 [M+H-(Boc)$_4$]$^+$ calc for C$_{339}$H$_{610}$N$_{63}$O$_7$ [M+H-(Boc)$_4$]$^+$ 6960.9; 6862 [M+H-(Boc)$_5$]$^+$ calc for C$_{334}$H$_{604}$N$_{63}$O$_{85}$ [M+H-(Boc)$_5$]$^+$ 6860.8.

BHALys[Lys]$_{16}$[TFA]$_{32}$

A solution of TFA/DCM (1:1, 19 mL) was added slowly to a stirred suspension of BHALys[Lys]$_{16}$[Boc]$_{32}$ (800 mg, 0.1 1 mmol) in DCM (25 mL). The solids dissolved, and the solution was stirred overnight under an atmosphere of argon. The solvents were removed under vacuum, and residual TFA was removed by repetitive freeze drying of the residue, to give BHALys[Lys]$_{16}$[TFA]32 as an off-white lyophylate (847 mg, 0.11 mmol) in 100% yield. $^1$H NMR (D$_2$O) δ 7.3 (br m, 11H, Ph Calc 10H); 6.06 (s, 1H, CH-Ph$_2$ Calc 1H); 4.3 (m, α-CH), 4.19 (m, α-CH), 4.0 (m, α-CH) and 3.88 (m, α-CH, total 35H, Calc 31H); 3.15 (br, ε-CH$_2$) and 2.98 (m, ε-CH$_2$ total 69H, Calc 62H); 1.88 (m, β,γ,δ-CH$_2$), 1.7 (m, β,γ,δ-CH$_2$) and 1.42 (m, β,γ,δ-CH$_2$ total 215H, Calc 186H). MS (ESI +ve) found 4158 [M+H]$^+$ calc for C$_{199}$H$_{386}$N$_{63}$O$_{31}$ [M+H]+ 4157.6.

HO-Lys(α-BOC)(ε-PEG$_{2100}$)

DIPEA (0.37 mL, 2.10 mmol) was added to an ice-cooled mixture of NHS-PEG$_{2100}$ (2.29 g, 1.05 mmol) and N-α-t-BOC-L-lysine (0.26 g, 1.05 mmol) in DMF (20 mL). The stirred mixture was allowed to warm to room temperature overnight then any remaining solids were filtered (0.45 µm PALL acrodisc) before removing the solvent in vacuo. The residue was taken up in ACN/H$_2$O (1:3, 54 mL) and purified by PREP HPLC (Waters XBridge C18, 5 µm, 19×150 mm, 25 to 32% ACN (5-15 min), 32 to 60% ACN (15 to 20 min), no buffer, 8 mL/min, RT=17 min), providing 1.41 g (56%) of HO-Lys(BOC)(PEG$_{2100}$). $^1$H NMR (CD$_3$OD) δ 3.96-4.09 (m, 1H), 3.34-3.87 (m, 188H); 3.32 (s, 3H), 3.15 (q, J=6.0 Hz, 2H), 2.40 (t, J=6.2 Hz, 2H), 1.28-1.88 (m, 6H), 1.41 (s, 9H).

BHALys[Lys]$_{32}$[α-BOC]$_{32}$[ε-PEG2100]$_{32}$ ‡

To a stirred mixture of BHALys[Lys]$_{16}$[TFA]$_{32}$ (0.19 g, 24 µmol) in DMF (20 mL) was added DIPEA (0.86 mL, 4.86 mmol). This mixture was then added dropwise to a stirred mixture of PyBOP (0.62 g, 1.20 mmol) and Lys(BOC)(PEG$_{2100}$) (2.94 g, 1.20 mmol) in DMF (20 mL) at room temperature. The reaction mixture was left to stir overnight, then diluted with water (200 mL). The aqueous mixture was subjected to a centramate filtration (5 k membrane, 20 L water). The retentate was freeze dried, providing 1.27 g (73%) of desired dendrimer. HPLC (C8 XBridge, 3×100 mm, gradient: 5% ACN (0-1 min), 5-80% ACN/H2O) (1-7 min), 80% ACN (7-12 min), 80-5% ACN (12-13 min), 5% ACN (13-15 min), 214 nm, 0.1% TFA) Rf (min)=8.52. 1H-nmr (300 MHz, D$_2$O) δ (ppm): 1.10-2.10 (m, Lys CH$_2$ (β, χ, δ) and BOC, 666H), 3.02-3.36 (m, Lys CH$_2$ (ε), 11 OH), 3.40 (s, PEG-OMe, 98H), 3.40-4.20 (m, PEG-OCH$_2$, 5750H+Lys CH surface, 32H), 4.20-4.50 (m, Lys, CH internal 32H), 7.20-7.54 (m, BHA, 8H). $^1$H NMR indicates approximately 29 PEGs.

BHALys[Lys]$_{32}$[α-TFA]$_{32}$[ε-PEG$_{2100}$]$_{32}$‡

1.27 g (17.4 mol) of BHALys[Lys]$_{32}$[α-BOC]$_{32}$[ε-PEG$_{2100}$]$_{32}$ was stirred in TFA/DCM (1:1, 20 mL) at room temperature overnight. The volatiles were removed in vacuo, then the residue was taken up in water (30 mL). The mixture was then concentrated. This process was repeated two more times before being freeze dried, providing 1.35 g (106%) of desired product as a viscous colourless oil. HPLC (C8 XBridge, 3×100 mm, gradient: 5% ACN (0-1 min), 5-80% ACN/H$_2$O) (1-7 min), 80% ACN (7-12 min), 80-5% ACN (12-13 min), 5% ACN (13-15 min), 214 nm, 0.1% TFA) Rf (min)=8.51. $^1$H-nmr (300 MHz, D$_2$O) δ (ppm): 1.22-2.08 (Lys CH$_2$ ((β, χ, δ), 378H), 3.00-3.26 (Lys CH2 (ε), 129H), 3.40 (PEG-OMe, 96H), 3.45-4.18 (PEG-OCH$_2$, 5610H+Lys CH surface, 32H), 4.20-4.46 (Lys, CH internal, 33H), 7.24-7.48 (8H, BHA). $^1$H NMR indicates approximately 29 PEGs.

Characterization of BHALys[Lys]$_{32}$[α-NH$_2$TFA]$_{32}$[ε-PEG$_{\sim 2000}$]$_{32}$‡

Table 6 illustrates the various batches of BHALys[Lys]$_{32}$[α-NH$_2$TFA]$_{32}$[ε-PEG$_{\sim 2000}$]$_{32}$™ were used in Examples 5-9 below, which have slightly different PEG lengths. The actual number of PEG chains on the dendrimer is also calculated by proton NMR.

TABLE 6

Various Batches of BHALys[Lys]$_{32}$[α-NH$_2$TFA]$_{32}$[ε-PEG$_{\sim 2000}$]$_{32}$‡

| Batch | Scale | PEG length from CoA (Da) | Number of PEGs (x) on BHALys[Lys]$_{32}$[α-NH$_2$•TFA]$_{32}$[ε-PEG$_{\sim 2000}$]$_x$ (from proton NMR*) | Estimated MW** (kDa) |
|---|---|---|---|---|
| 1 | 101 mg | 2200 | 29 | 75.7 |
| 2 | 98 mg | 2200 | 29 | 75.7 |
| 3 | 74.8 g | 2100 | 29 | 72.8 |
| 4 | 137 mg | 2200 | 29 | 75.7 |
| 5 | 1.19 g | 2100 | 31 | 77.0 |
| 6 | 18.98 g | 2100 | 29 | 72.8 |

*Number of PEGs is calculated from the proton NMR. For batch 1: No. of PEGs = Number (integration) of protons in PEG region of NMR (3.4-4.2 ppm)/Average (mean) number of protons per PEG chain (CoA PEG/44Da × 4H) = 5706H/(2200/44 × 4) = 28.53 (approx. 29 PEG units)

**Molecular Weight estimated by adding MW of various components. For batch 1: Total MW = Mw of dendrimer + Mw of TFA + Mw of PEG = BHALys[Lys]$_{32}$ + 32 (TFA) + 29 (PEG) = 8,258 + 3,648 + 63800 = ~75.7 kDa The proton NMR for the various batches of BHALys[Lys]$_{32}$[α-NH$_2$TFA]$_{32}$[ε-PEG$_{\sim 2000}$]$_{32}$‡ is presented in the Table 7:

TABLE 7

Proton NMR Data for Various Batches of BHALys[Lys]$_{32}$[α-NH$_2$TFA]$_{32}$[ε-PEG$_{\sim 2000}$]$_{32}$‡

| Batch | Scale | Proton NMR of BHALys[Lys]$_{32}$[α-NH$_2$•TFA]$_{32}$[ε-PEG$_{\sim 2000}$]$_x$ |
|---|---|---|
| 1 | 101 mg | 1.22-2.08 (Lys CH$_2$(β,χ,δ), 378H), 3.00-3.26 (Lys CH$_2$ (α), 129H), 3.40 (PEG-OMe, 96H), 3.45-4.18 (PEG-OCH$_2$, 5610H + Lys CH surface, 32H), 4.20-4.46 (Lys, CH internal, 33H), 7.24-7.48 (8H, BHA). |
| 2 | 98 mg | As for batch 1 |
| 3 | 74.8 g | 1.02-2.18 (Lys CH$_2$(β,χ,δ), 378H), 2.94-3.36 (Lys CH$_2$ (α), 129H), 3.41 (PEG-OMe, 93H), 3.45-4.18 (PEG-OCH$_2$, 5432H + Lys CH surface, 32H), 4.18-4.50 (Lys, CH internal, 32H), 7.12-7.64 (9H, BHA). |
| 4 | 137 mg | As for batch 1 |
| 5 | 1.19 g | 1.02-2.16 (Lys CH$_2$(β,χ,δ), 378H), 2.93-3.36 (Lys CH$_2$ (α), 129H), 3.41 (PEG-OMe, 101H), 3.45-4.18 (PEG-OCH$_2$, 5908H + Lys CH surface, 32H), 4.18-4.50 (Lys, CH internal, 32H), 7.21-7.54 (9H, BHA). |
| 6 | 18.98 g | As for batch 3 |

Example 5: Preparation of BHALys[Lys]$_{32}$[α-Glu-Compound A]$_{32}$†[ε-PEG$_{2200}$]$_{32}$‡

Note.

32† relates to the theoretical number of α-amino groups on the dendrimer available for substitution with Glu-Compound A. The actual mean number of Glu-Compound A groups attached to BHALys[Lys]$_{32}$ was determined experimentally by $^1$H NMR (see Example 10). 32‡ relates to the theoretical number of ε-amino groups on the dendrimer available for substitution with PEG$_{2200}$. The actual mean number of PEG$_{2200}$ groups attached to BHALys[Lys]$_{32}$ was determined experimentally by $^1$H NMR (see Example 4, Batch 1).

Preparation of Glu-Compound A

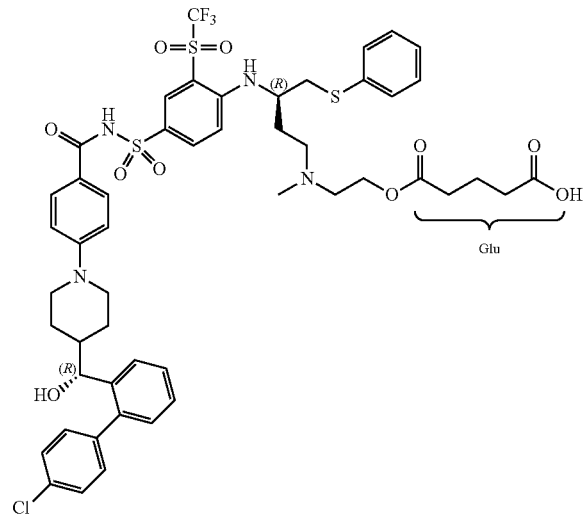

To a magnetically stirred suspension of Compound A (200 mg, 0.21 mmol) in DCM (10 mL) at room temperature was added glutaric anhydride (29 mg, 0.25 mmol), DMAP (26 mg, 0.21 mmol) and DIPEA (93 μL, 0.53 mmol). The suspension dissolved quickly and the mixture was left to stir at room temperature overnight. Additional glutaric anhydride was added over the following 24 hours until the reaction was judged >80% complete by HPLC. The volatiles were then removed in vacuo and the residue purified by preparative HPLC (BEH 300 Waters XBridge C18, 5 μM, 30×150 mm, 60-80% ACN/water (5-40 min), 0.1% TFA, RT=22 min) providing 117 mg (52%) of product as a white solid. LCMS (C18, gradient: 50-60% ACN/H$_2$O (1-10 min), 60% ACN (10-11 min), 60-50% ACN (11-13 min), 50% ACN (13-15 min), 0.1% formic acid, 0.4 mL/min, Rf (min)=6.30. ESI (+ve) observed [M+H]$^+$=1059. Calculated for $C_{50}H_{54}ClF_3N_4O_{10}S_3$=1058.26 Da. 1H-NMR (300 MHz, CD$_3$OD) δ (ppm): 0.65-1.40 (m, 4H), 1.70-2.30 (m, 6H), 2.34 (t, J=6.9 Hz, 2H), 2.42 (t, J=7.5 Hz, 2H), 2.65 (t, J=12.3 Hz, 1H), 2.79 (t, J=12.6 Hz, 1H), 2.91 (s, 3H), 3.14-3.29 (m, 2H), 3.33-3.38 (m, 3H), 3.38-3.52 (m, 3H), 3.71 (d, J=12.9 Hz, 1H), 3.89 (d, J=12.9 Hz, 1H), 4.10 (m, 1H), 4.34-4.48 (m, 3H), 6.80-6.96 (m, 3H), 7.01 (d, J=9.0 Hz, 1H), 7.09-7.24 (m, 4H), 7.26-7.46 (m, 8H), 7.61 (d, J=7.8 Hz, 1H), 7.68 (d, J=9.0 Hz, 2H), 8.07 (dd, J=9.3, 2.1 Hz, 1H), 8.31 (d, J=3.0 Hz, 1H).

Preparation of BHALys[Lys]$_{32}$ [α-Glu-Compound A]$_{31}$[ε-PEG$_{2200}$]$_{29}$

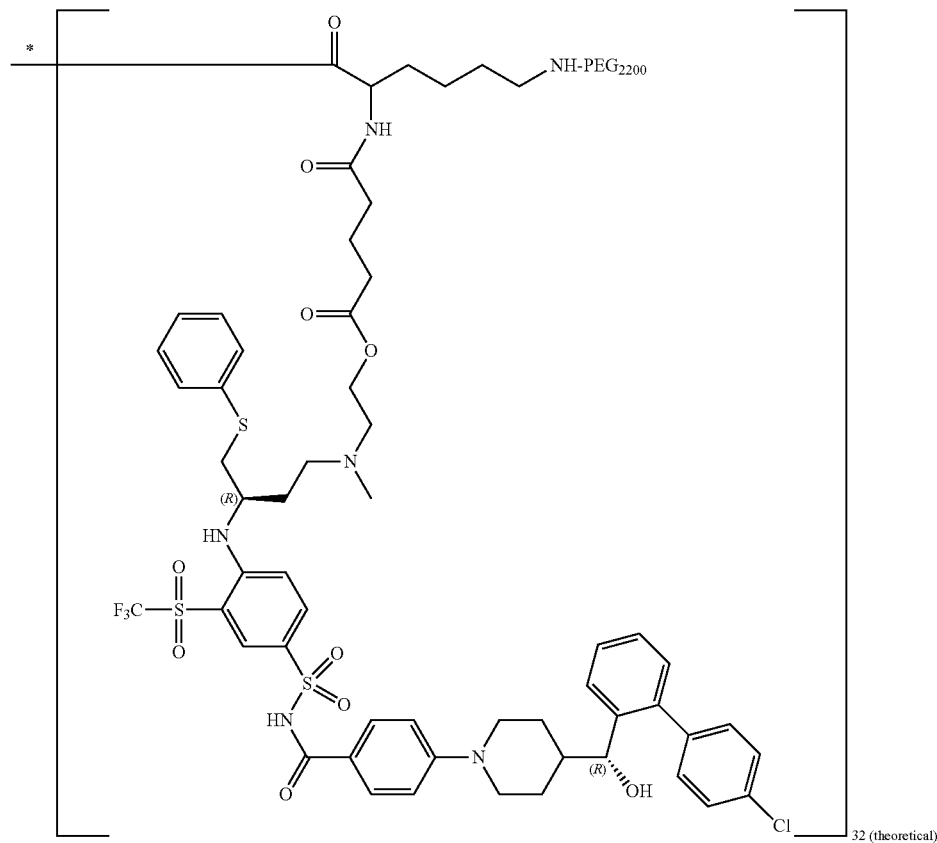

* = BHALys[Lys]$_{16}$

To a magnetically stirred mixture of Compound A-Glu (67 mg, 63 µmol) and PyBOP (33 mg, 63.3 µmol) in DMF (1 mL) at room temperature was added a mixture of BHALys[Lys]$_{32}$[α-NH$_2$TFA]$_{32}$[ε-PEG$_{2200}$]$_{29}$ (99 mg, 1.32 µmol, Batch 1 of Example 4) and NMM (23 µL, 0.21 mmol), also in DMF (2 mL). After 16 hours at room temperature the volatiles were removed and the residue purified by size exclusion chromatography (sephadex, LH20, MeOH). The appropriate fractions, as judged by HPLC, were combined and concentrated. The residue was then taken up in water, filtered (0.22 µm) and lyophilised, providing 101 mg (73%) of desired material as a pale pink solid. HPLC (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate) Rf (min)=10.18. $^1$H-NMR (300 MHz, CD$_3$OD) δ (ppm): 0.65-2.08 (m, 585H), 2.10-2.50 (m, 144H), 2.50-2.80 (m, 71H), 2.82-3.02 (m, 80H), 3.04-3.27 (m, 137H), 3.35 (s, 108H), 3.40-4.06 (m, 5824H), 4.08-4.62 (m, 181H), 6.54-8.40 (m, 632H).

Example 6: Preparation of BHALys[Lys]$_{32}$[α-TDA-Compound A]$_{32\dagger}$[ε-PEG$_{2100, 2200}$]$_{32}$ ‡

Note:

32† relates to the theoretical number of α-amino groups on the dendrimer available for substitution with TDA-Compound A. The actual mean number of TDA-Compound A groups attached to BHALys[Lys]$_{32}$ was determined experimentally by $^1$H NMR (see Example 10). 32‡ relates to the theoretical number of ε-amino groups on the dendrimer available for substitution with PEG$_{2100, 2200}$. The actual mean number of PEG$_{2100, 2200}$ groups attached to the BHALys[Lys]$_{32}$ was determined experimentally by $^1$H NMR (see Example 4, Batch 2 and Batch 3).

Preparation of TDA-Compound A

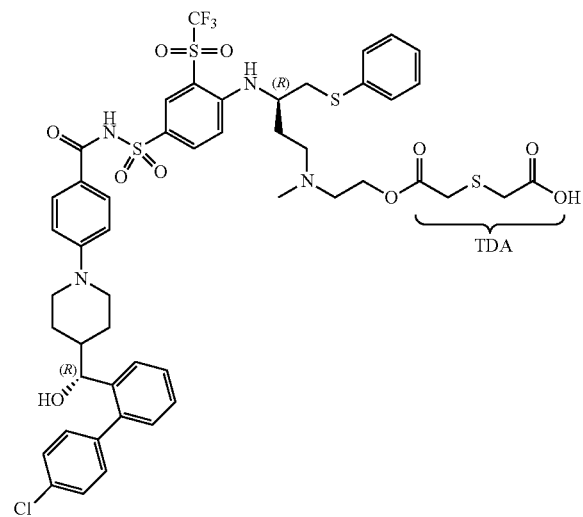

To a magnetically stirred suspension of Compound A (70 mg, 74.1 µmol) in DCM (5 mL) at room temperature was added thiodiglycolic anhydride (TDA, 10 mg, 74.1 µmol) and DIPEA (33 µL, 185 µmol). The suspension dissolved quickly and the mixture was left to stir at room temperature overnight. Additional thiodiglycolic anhydride was added over the following 24 hours until the reaction was judged >80% complete by HPLC. The volatiles were then removed in vacuo and the residue purified by preparative HPLC (BEH 300 Waters XBridge C18, 5 µM, 30×150 mm, 60-80% ACN/water (5-40 min), 0.1% TFA, RT=22 min) providing 63 mg (70%) of product as a white solid. LCMS (C18, gradient: 50-60% ACN/H$_2$O (1-10 min), 60%/0 ACN (10-11 min), 60-50% ACN (11-13 min), 50% ACN (13-15 min), 0.1% formic acid, 0.4 mL/min, Rf (min)=7.33. ESI (+ve) observed [M+H]$^+$=1077. Calculated for C$_{49}$H$_{52}$ClF$_3$N$_4$O$_{10}$S$_4$=1076.22 Da. $^1$H-NMR (300 MHz, CD$_3$OD) δ (ppm): 0.87-1.04 (m, 1H), 1.08-1.36 (m, 3H), 1.71-1.90 (m, 1H), 1.96-2.40 (m, 3H), 2.64 (t, J=12.0 Hz, 1H), 2.77 (t, J=12.6 Hz, 1H), 2.94 (s, 3H), 3.18-3.30 (m, 2H), 3.35 (s, 2H), 3.40 (s, 2H), 3.46-3.55 (m, 2H), 3.73 (d, J=13.5 Hz, 1H), 3.90 (d, J=12.9 Hz, 1H), 4.02-4.15 (m, 1H), 4.40-4.48 (m, 3H), 6.86 (d, J=9.3 Hz, 2H), 6.92 (d, J=9.6 Hz, 1H), 7.02 (d, J=9.0 Hz, 1H), 7.08-7.46 (m, 13H), 7.61 (d, J=7.8 Hz, 1H), 7.67 (d, J=9.0 Hz, 2H), 8.08 (dd, J=9.3, 2.1 Hz, 1H), 8.31 (d, J=2.1 Hz, 1H).

Alternative Method of Preparation

Compound A (25.50 g, 2.70×10$^{-2}$ mol) and TDA (4.81 g, 3.64×10$^{-2}$ mol, 1.35 equiv.) were charged into a 3-neck reaction vessel fitted with an internal temperature probe and pressure equalizing dropping funnel under an atmosphere of N$_2$. DCM (255 mL, 10 vol.) was introduced, and the ensuing suspension was cooled to −10° C. 0.29M TEA in DCM, (100 mL, 3.77×10$^{-2}$ mol, 1.4 equiv.) was introduced over a 40 minute period whilst maintaining the temperature at −10° C. Reaction in-process controls (IPC's) were taken hourly. The reaction was deemed complete when Compound A was <10% area by HPLC (typically 4.5 h after the end of addition). The reaction mixture was diluted with DCM (1.66 L, 65 vol.) and washed three times with aq. phosphate buffered saline (PBS) solution (1.02 L, 40 vol.). The combined organic extracts were dried over MgSO$_4$ (100 g, 5% w/v), affording a pale yellow solid after concentration in vacuo (0.2 bar, 25° C.) overnight (typically 24.5 g, 85% yield, 86.83% by HPLC).

Preparation of BHALys[Lys]$_{32}$[α-TDA-Compound A]$_{32}$ †[ε-PEG$_{2100, 2200}$]$_{32}$‡

Small Scale Method of Preparation

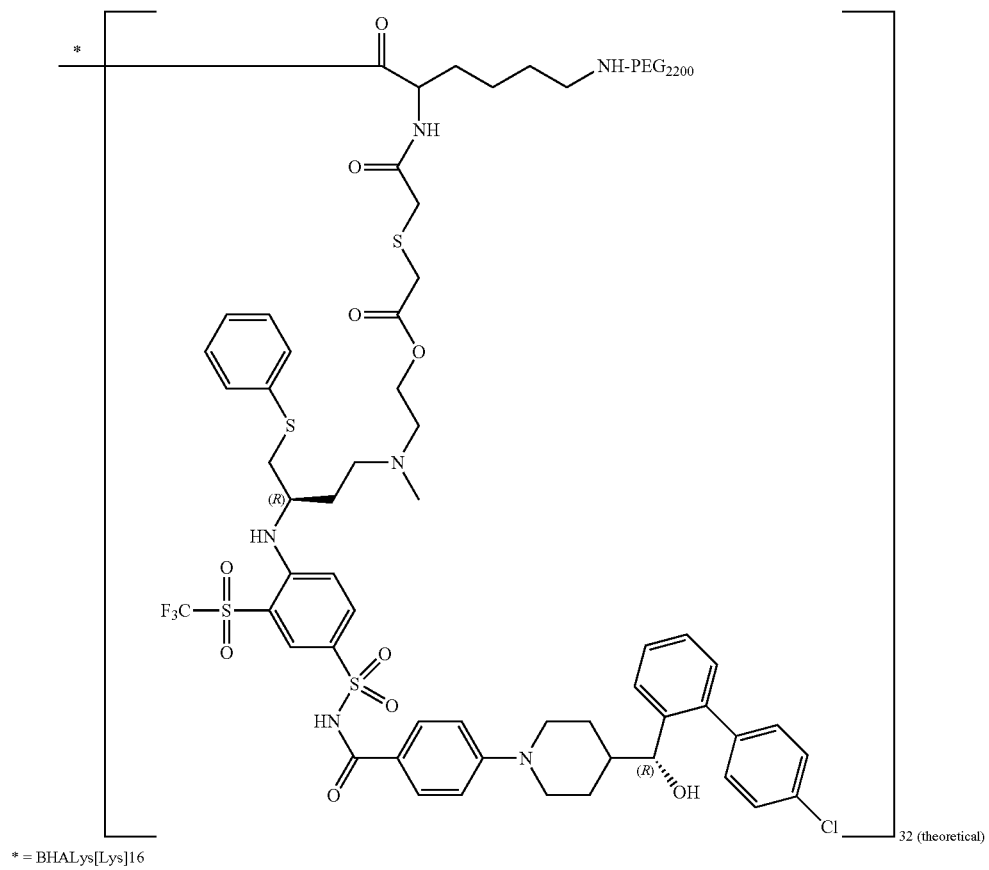

* = BHALys[Lys]16

To a magnetically stirred mixture of Compound A-TDA (62 mg, 58 μmol) and PyBOP (30 mg, 58 μmol) in DMF (1 mL) at room temperature was added a mixture of BHALys [Lys]$_{32}$[α-NH$_2$TFA]$_{32}$[ε-PEG$_{2200}$]$_{29}$ (97 mg, 1.28 μmol, Batch 2 of Example 4) and NMM (27 μL, 0.24 mmol), also in DMF (2 mL). After 16 hours at room temperature the volatiles were removed and the residue purified by size exclusion chromatography (sephadex, LH20, MeOH). The appropriate fractions, as judged by HPLC, were combined and concentrated. The residue was then taken up in water, filtered (0.22 μm) and lyophilized, providing 98 mg (72%) of desired material as a pale pink solid. HPLC (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate) Rf (min)=10.24. $^1$H-NMR (300 MHz, CD$_3$OD) δ (ppm): 0.62-2.33 (m, 589H), 2.37-2.69 (m, 87H), 2.69-2.92 (m, 98H), 2.94-3.27 (m, 202H), 3.35 (s, 113H), 3.37-4.10 (m, 5781H), 4.10-4.70 (m, 154H), 6.50-8.45 (m, 661H).

Alternative (Large Scale) Method of Preparation

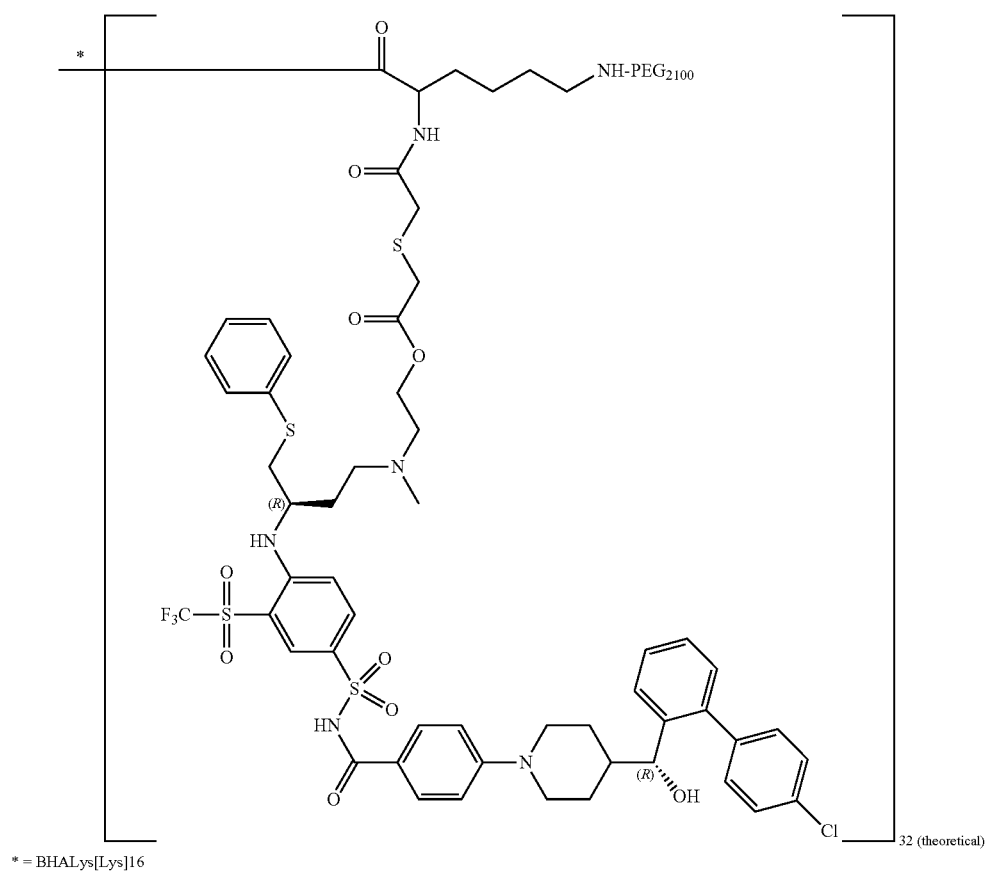

* = BHALys[Lys]16

DMF (495 mL, 16.5 vol.) was added to BHALys[Lys]$_{32}$ [α-NH$_2$TFA]$_{32}$[ε-PEG$_{2100}$]$_{29}$, (30.6 g, 3.82×10$^{-4}$ mol, Batch 3 of Example 4) and Compound A-TDA (19.01 g, 1.53×10$^{-2}$ mol, 40 equiv.) under an atmosphere of N$_2$. NMM (8.06 mL, 7.33×10$^{-2}$ mol, 192 equiv.) was introduced, and the reaction was warmed to 30° C. to aid dissolution (approximately 10 mins). The mixture was then cooled back to 20° C. and PyBOP (9.20 g, 1.68×10-2 mol., 44 equiv.) was introduced in two equal portions. In process control monitoring revealed reaction completion after 2 h. The reaction mixture was diluted with ACN (495 mL, 16.5 vol.), filtered through a sinter funnel and subjected to 10 constant diavolumes (600 mL, ACN) of ultrafiltration (Merck Millipore Pellicon 3, 2×0.11 m2 cassette), maintaining a transmembrane pressure (TMP) of 18 PSI and 48 L/m2/hour (LMH). Concentration under reduced pressure (45° C., 0.2 bar; for 30 mins.), and drying at ambient for a further 16 h afforded 45.7 g of Purified product (Batch A) as a dark yellow syrup. This process was repeated to produce another 46.8 g of material (Batch B).

The two batches (Batches A and B) were individually taken up in THF (4.7 vol.) and warmed to 35-40° C. until dissolution was complete (10 mins.). To a separate 3-neck round bottom vessel, fitted with an internal thermometer, pressure equalizing dropping funnel and magnetic stirrer was added MTBE (1.8 L, 19.5 vol.). The solvent was then cooled to 0° C. with the aid of an external ice bath. The combined THF solutions of batches A and B were charged to the dropping funnel upon reaching ambient temperature, and introduced drop-wise to the stirred solution of MTBE whilst maintaining the temperature at 0° C. At the first sight of cloudiness, the reaction was seeded with solid BHALys[Lys]$_{32}$[α-TDA-Compound A]$_{27}$[ε-PEG$_{2200}$]$_{29}$ (0.95 g, 1% w/w relative to input batches A and B) and addition resumed, lasting 30 minutes. Crystallization was allowed to ripen for 60 minutes, before being transferred to a Buchner vacuum filter (160 mm diameter) under N$_2$ (lasting 15 mins.). The filter cake was washed twice with 5 vol. MTBE (300 mL per wash) and pulled to dryness (under N$_2$) lasting a total of 30 minutes. The filter cake was transferred to a vacuum oven where drying took place at 40° C., 0.2 bar until constant mass was achieved (24 h), affording free flowing white powder in 74.8 g (105% yield). HPLC (C8 Phenomenix Aeris, 2.1×100 mm, gradient: 5% ACN (0-1 min), 5-45% ACN/H$_2$O) (1-2 min), 45-60% ACN (2-8 min), 60% ACN (8-10 min), 60-90% ACN (10-10.1 min), 90% ACN (10.1-12 min), 90-5% ACN (12-15 min), 5% ACN (15-20 min), 272 nm, 10 mM ammonium formate) Rf (min)=14.92. $^1$H-NMR (300 MHz, CD$_3$OD) δ (ppm): 0.40-2.30 (m, 589H), 2.31-2.79 (m, 154H), 2.81-3.29 (m, 263H), 3.35 (s, 116H), 3.36-4.10 (m, 5924H), 4.13-4.62 (m, 151H), 6.28-8.52 (m, 622H). 19F-NMR (300 MHz, DMSO-d6) δ: −106.9 ppm (3.81 mg, FBA, set integration to 100), −79.0 ppm (21.4 mg dendrimer, 62.80). This provides 5.36 mg Compound A (or 25.1% loading).

Example 7: Preparation of BHALys[Lys]$_{32}$[α-DGA-Compound A]$_{32†}$[ε-PEG$_{2200}$]$_{32‡}$ Note:

32† relates to the theoretical number of α-amino groups available for substitution with DGA-Compound A. The actual mean number of DGA-Compound A groups attached to the BHALys[Lys]$_{32}$ was determined experimentally by $^1$H NMR (see Example 10). 32‡ relates to the maximum theoretical number of ε-amino groups available for substitution with PEG$_{2200}$. The actual mean number of PEG$_{2200}$ groups attached to the BHALys[Lys]$_{32}$ was determined experimentally by $^1$H NMR (see Example 4, Batch 4).

Preparation of DGA-Compound A

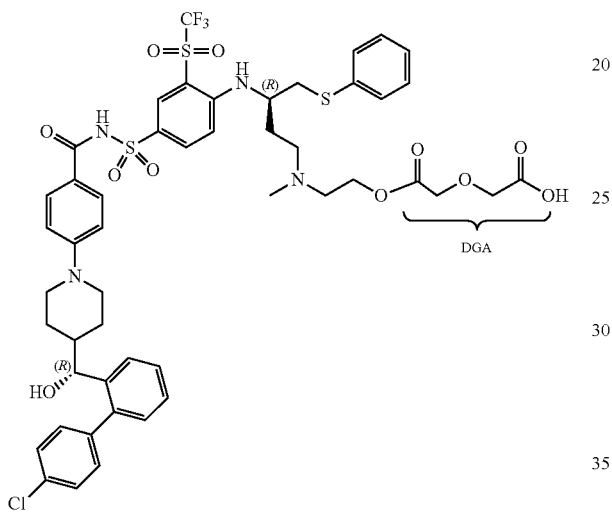

To a magnetically stirred suspension of Compound A (77 mg, 81.5 μmol) in DCM (5 mL) at room temperature was added diglycolic anhydride (9.6 mg, 81.5 μmol) and DIPEA (36 μL, 200 μmol). The suspension dissolved quickly and the mixture was left to stir at room temperature overnight. Additional diglycolic anhydride was added over the following 24 hours until the reaction was judged >80% complete by HPLC. The volatiles were then removed in vacuo and the residue purified by preparative HPLC (BEH 300 Waters XBridge C18, 5 μM, 30×150 mm, 60-80% ACN/water (5-40 min), 0.1% TFA, RT=22 min) providing 76 mg (87%) of product as a white solid. LCMS (C18, gradient: 50-60% ACN/H$_2$O (1-10 min), 60%/0 ACN (10-11 min), 60-50% ACN (11-13 min), 50% ACN (13-15 min), 0.1% formic acid, 0.4 mL/min, Rf (min)=5.93. ESI (+ve) observed [M+H]$^+$=1061. Calculated for C$_{49}$H$_{52}$ClF$_3$N$_4$O$_{11}$S$_3$=1060.24 Da. 1H-NMR (300 MHz, CD$_3$OD) δ (ppm): 0.86-1.04 (m, 1H), 1.08-1.32 (m, 2H), 1.70-1.90 (m, 1H), 1.97-2.08 (m, 1H), 2.08-2.20 (m, 1H), 2.22-2.38 (m, 1H), 2.65 (t, J=12.3 Hz, 1H), 2.77 (t, J=12.6 Hz, 1H), 2.92 (s, 3H), 3.15-3.29 (m, 2H), 3.36-3.42 (m, 2H), 3.46-3.54 (m, 2H), 3.73 (d, J=12.6 Hz, 1H), 3.90 (d, J=11.7 Hz, 1H), 3.99-4.15 (m, 1H), 4.20 (s, 2H), 4.28 (s, 2H), 4.42 (j, J=8.1 Hz, 1H), 4.45-4.54 (m, 2H), 6.86 (d, J=9.3 Hz, 2H), 6.92 (d, J=9.6 Hz, 1H), 7.01 (d, J=9.3 Hz, 1H), 7.10-7.26 (m, 4H), 7.26-7.47 (m, 7H), 7.59 (d, J=7.8 Hz, 1H), 7.67 (d, J=9.0 Hz, 2H), 8.08 (dd, J=9.0, 2.1 Hz, 1H), 8.31 (d, J=2.1 Hz, 1H).

Preparation of BHALys[Lys]$_{32}$[α-DGA-Compound A]$_{32\dagger}$[ε-PEG$_{2200}$]$_{32\ddagger}$

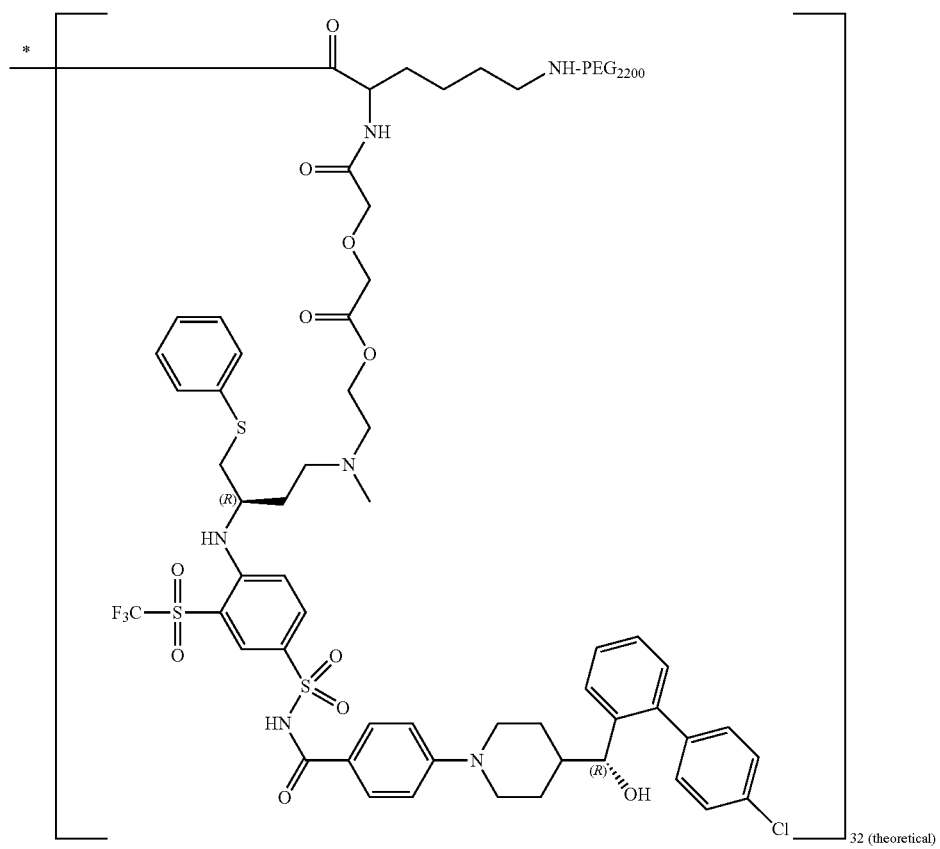

\* = BHALys[Lys]16

To a magnetically stirred mixture of Compound A-DGA (76 mg, 72 μmol) and PyBOP (37 mg, 72 μmol) in DMF (1 mL) at room temperature was added a mixture of BHALys [Lys]$_{32}$[α-NH$_2$TFA]$_{32}$[ε-PEG$_{2200}$]$_{29}$ (112 mg, 1.49 μmol, Batch 4 of Example 4) and NMM (31 μL, 0.29 mmol), also in DMF (2 mL). After 16 hours at room temperature the volatiles were removed and the residue purified by size exclusion chromatography (sephadex, LH20, MeOH). The appropriate fractions, as judged by HPLC, were combined and concentrated. The residue was then taken up in water, filtered (0.22 μm) and lyophilised, providing 137 mg (88%) of desired material as a pale pink solid. HPLC (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate) Rf (min)=10.23. $^1$H-NMR (300 MHz, CD$_3$OD) δ (ppm): 0.58-2.26 (m, 834H), 2.28-2.72 (m, 154H), 2.74-3.28 (m, 245H), 3.35 (s, 101H), 3.37-4.02 (m, 5824H), 4.04-4.68 (m, 272H), 6.46-8.54 (m, 652H).

Example 8: Preparation of BHALys[Lys]$_{32}$[α-Glu-Compound A]$_{32\dagger}$[ε-PEG$_{1100}$]$_{32\ddagger}$ Note:

32† relates to the theoretical number of α-amino groups on the dendrimer available for substitution with Glu-Compound A. 32‡ relates to the maximum theoretical number of ε-amino groups available for substitution with PEG$_{1100}$.

Preparation of BHALys[Lys]$_{32}$[α-Glu-Compound A]$_{32\dagger}$[ε-PEG$_{1100}$]$_{32\ddagger}$

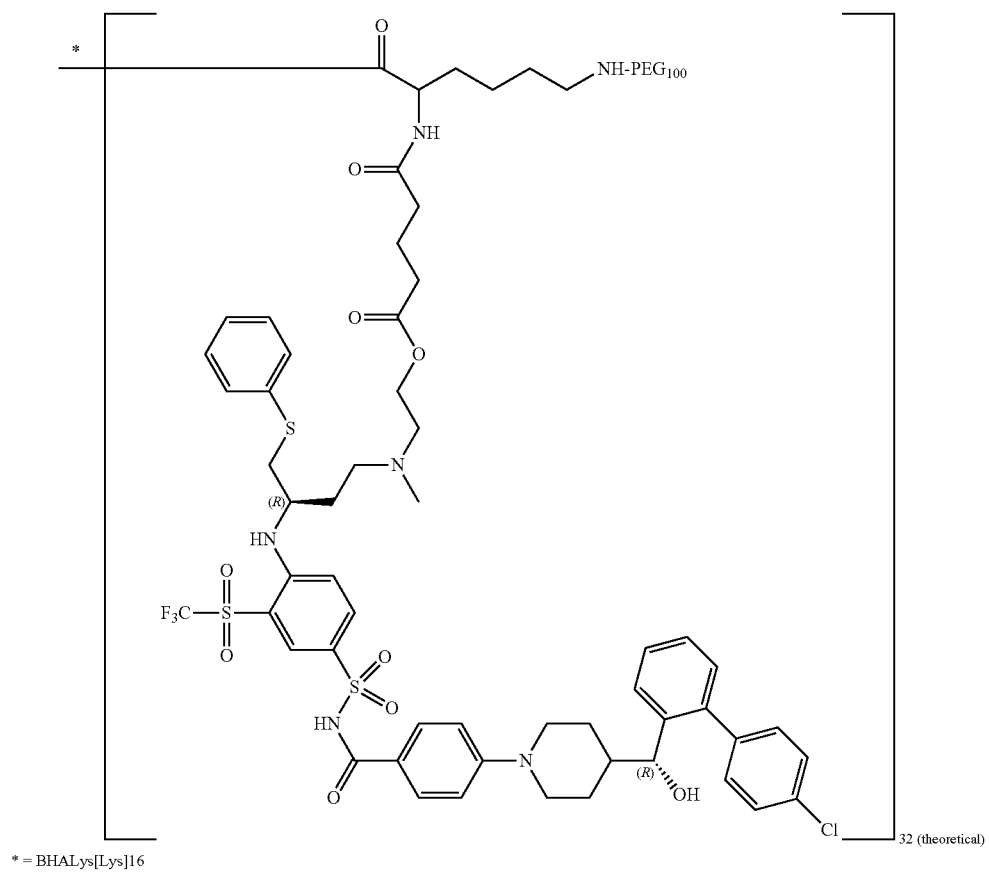

* = BHALys[Lys]16

To a magnetically stirred mixture of Compound A-Glu (57 mg, 54 μmol) and PyBOP (28 mg, 54 μmol) in DMF (1 mL) at room temperature was added a mixture of BHALys [Lys]$_{32}$[α-NH$_2$TFA]$_{32}$[ε-PEG$_{1100}$]$_{32\#}$ (57 mg, 1.20 μmol) and NMM (25 μL, 0.23 mmol), also in DMF (2 mL). After 16 hours at room temperature the volatiles were removed and the residue purified by size exclusion chromatography (sephadex, LH20, ACN). The appropriate fractions, as judged by HPLC, were combined and concentrated. The residue was then taken up in water, filtered (0.22 μm) and lyophilised, providing 72 mg (78%) of desired material as a pale pink solid. HPLC (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate) Rf (min)=10.40. 1H-NMR (300 MHz, CD$_3$OD) δ (ppm): 0.60-2.08 (m, 632H), 2.10-2.35 (m, 127H), 2.36-2.53 (m, 114H), 2.54-2.78 (m, 117H), 2.82-3.27 (m, 254H), 3.34 (s, 102H), 3.37-3.89 (m, 3226H), 3.90-4.58 (m, 185H), 6.36-8.52 (m, 654H).

Example 9: Preparation of BHALys[Lys]$_{32}$[α-MIDA-Compound A]$_{32\dagger}$[ε-PEG$_{2100}$]$_{32\ddagger}$ Note:

32† relates to the theoretical number of α-amino groups on the dendrimer available for substitution with MIDA-Compound A. The actual mean number of MIDA-Compound A groups attached to BHALys[Lys]$_{32}$ was determined experimentally by $^{19}$F NMR (see Example 10). 32‡ relates to the theoretical number of ε-amino groups on the dendrimer available for substitution with PEG$_{2100}$. The actual mean number of PEG$_{2100}$ groups attached to BHALys [Lys]$_{32}$ was determined experimentally by $^1$H NMR (see Example 4, Batch 5 and 6).

Preparation of MIDA-Compound A

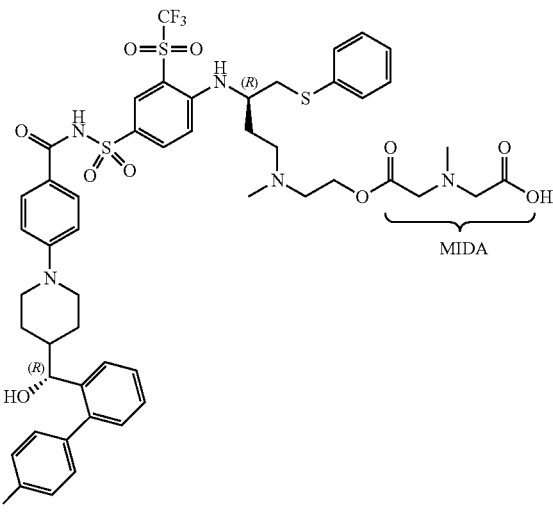

To a magnetically stirred suspension of Compound A (200 mg, 0.21 mmol) in DCM (5 mL) at room temperature was added and DIPEA (24 µL, 0.14 mmol), NMM (72 µL, 0.66 mmol) and 4-methylmorpholine-2,6-dione (33 mg, 0.26 mmol). The suspension dissolved quickly and the mixture was left to stir at room temperature overnight. Additional 4-methylmorpholine-2,6-dione was added over the following 24 hours until the reaction was judged >80% complete by HPLC. The volatiles were then removed in vacuo and the residue purified by preparative HPLC (BEH 300 Waters XBridge C18, 5 µM, 30×150 mm, 50-70% ACN/water (5-40 min), 0.1% TFA, RT=23 min) providing 190 mg (84%) of product as a white solid. LCMS (C18, gradient: 50-60% ACN/H$_2$O (1-10 min), 60% ACN (10-11 min), 60-50% ACN (11-13 min), 50% ACN (13-15 min), 0.1% formic acid, 0.4 mL/min, Rf (min)=2.55. ESI (+ve) observed [M+H]$^+$=1074. Calculated for $C_{50}H_{55}ClF_3N_5O_{10}S_3$=1073.28 Da. $^1$H-NMR (300 MHz, CD$_3$OD) δ (ppm): 0.86-1.07 (m, 1H), 1.08-1.37 (m, 2H), 1.72-1.88 (m, 1H), 1.96-2.09 (m, 1H), 2.10-2.24 (m, 1H), 2.24-2.38 (m, 1H), 2.66 (t, J=12.3 Hz, 1H), 2.79 (t, J=12.6 Hz, 1H), 2.92 (s, 3H), 3.00 (s, 3H), 3.14-3.28 (m, 2H), 3.33-3.43 (m, 2H), 3.47-3.57 (m, 2H), 3.72 (d, J=12.0 Hz, 1H), 3.89 (d, J=12.6 Hz, 1H), 4.03-4.15 (m, 1H), 4.06 (s, 2H), 4.19 (s, 2H), 4.43 (d, J=8.1 Hz, 1H), 4.54-4.64 (m, 2H), 6.88 (d, J=9.0 Hz, 2H), 6.93 (d, J=9.6 Hz, 1H), 7.01 (d, J=9.0 Hz, 1H), 7.09-7.25 (m, 4H), 7.26-7.47 (m, 8H), 7.61 (d, J=8.1 Hz, 1H), 7.68 (d, J=9.0 Hz, 1H), 8.07 (dd, J=9.3, 2.1 Hz, 1H), 8.31 (d, J=2.1 Hz, 1H).

Alternative Method of Preparation

Compound A (28.00 g, 2.96×10$^{-2}$ mol) and 4-methylmorpholine-2,6-dione (7.24 g, 5.33×10-2 mol., 1.80 equiv.) were charged into a 3-neck reaction vessel with an internal temperature probe and pressure equalizing dropping funnel, under an atmosphere of N$_2$. DCM (250 mL, 9 vol.) was introduced, and the ensuing suspension was cooled to 0° C. TEA (6.25 mL, 4.44×10$^{-2}$ mol., 1.5 equiv.) in DCM (50 mL, 1.8 vol.) was added drop-wise over a 10 minute period whilst maintaining the temperature at 0° C. Reaction in process controls were taken hourly. The reaction was deemed complete when Compound A is <10% by peak area (typically 4.5 h after the end of addition). The reaction mixture is diluted with DCM (1.40 L, 50 vol.) and washed twice with 1.6 M aq. Na$_2$CO$_3$ (1.60 L, 50 vol.). The organic layer was dried over MgSO$_4$ (90 g, 5% w/v), filtered through a sintered glass funnel and washed with DCM (100 mL, 5 vol.) affording an off-white solid after concentration in vacuo (0.2 bar, 30° C.) (33.07 g, 95% yield, 90.6% by HPLC).

Preparation of BHALys[Lys]$_{32}$[α-MIDA-Compound A]$_{32\dagger}$[ε-PEG2100]$_{32\ddagger}$ Small Scale Method of Preparation

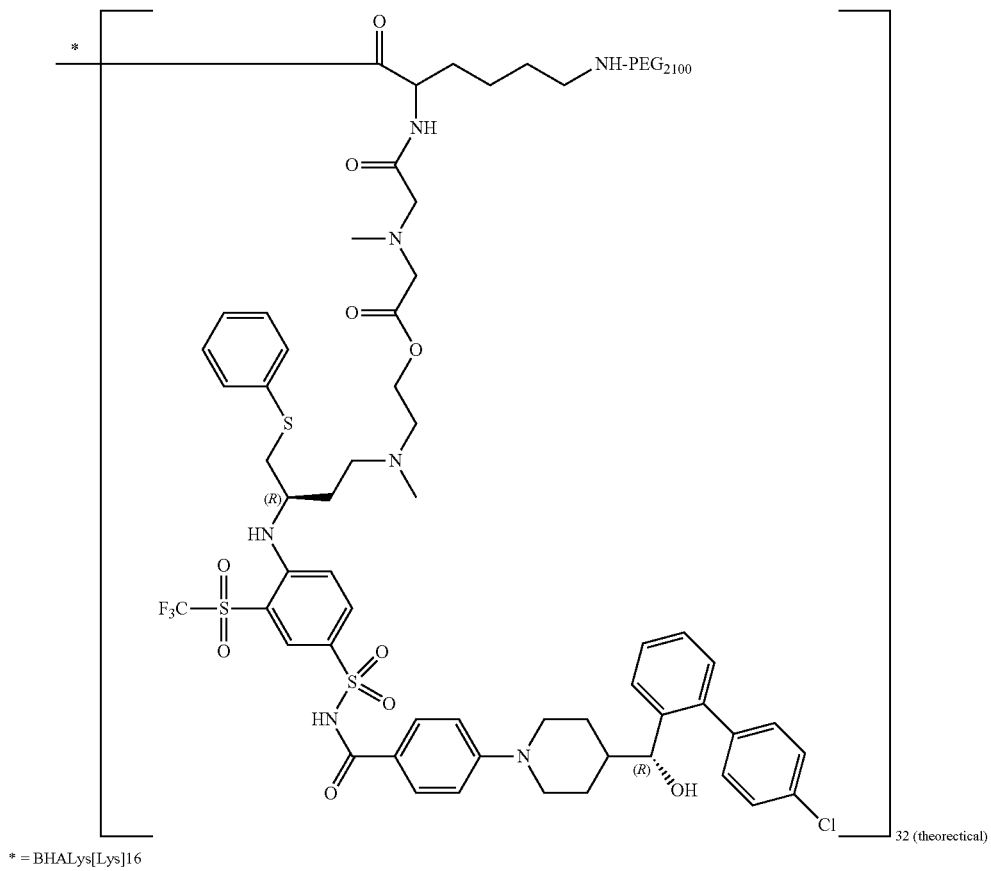

* = BHALys[Lys]16

To a magnetically stirred mixture of Compound A-MIDA (730 mg, 0.68 mmol) and PyBOP (353 mg, 0.68 mmol) in DMF (10 mL) at room temperature was added a mixture of BHALys[Lys]$_{32}$[α-NH$_2$TFA]$_{32}$[ε-PEG$_{2100}$]$_{31}$ (934 mg, 12.1 µmol, Batch 5 of Example 4) and NMM (255 µL, 2.32 mmol), also in DMF (10 mL). After 16 hours at room temperature the volatiles were removed and the residue purified by size exclusion chromatography (sephadex, LH20, ACN). The appropriate fractions, as judged by HPLC, were combined and concentrated. The residue was then taken up in water, filtered (0.22 μm) and lyophilised, providing 1.19 g (92%) of desired material as a pale pink solid. HPLC (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate) Rf (min)=10.80. 1H-NMR (300 MHz, CD$_3$OD) δ (ppm): 0.45-1.92 (m, 565H), 2.08-2.78 (m, 228H), 2.79-3.00 (m, 96H), 3.01-3.28 (m, 180H), 3.35 (s, 180H), 3.46-4.20 (m, 6164H), 4.20-4.68 (m, 139H), 6.40-8.52 (m, 680H).

Alternative (Large Scale) Method of Preparation

DMF (225 mL, 16.5 vol.) was added to BHALys [Lys]$_{32}$[α-NH$_2$TFA]$_{32}$[ε-PEG$_{2100}$]$_{29}$ (13.49 g, 1.72×10$^{-4}$ mol, Batch 6 of Example 4) and Compound A-MIDA (8.50 g, 6.87×10$^{-3}$ mol., 40.2 equiv.) under an atmosphere of N$_2$. NMM (3.60 mL, 3.30×10-2 mol, 192 equiv.) was introduced, and the reaction mixture was warmed to 30-35° C. to aid dissolution (approximately 5 minutes). The mixture was then cooled back to 20° C., and PyBOP (4.13 g, 7.56×10$^{-3}$ mol, 44 equiv.) was introduced in two equal portions. In process control monitoring revealed reaction completion after 2 h. The reaction mixture was diluted with ACN (225 mL, 16.5 volumes), filtered through a sinter funnel and subjected to 16 (constant) diavolumes (200 mL, ACN) of ultrafiltration (Merck Millipore Pellicon 3, 0.11 m2 cassette, 10 kDa), maintaining a transmembrane pressure (TMP) of 25 PSI and 44 L/m2/hour (LMH). Concentration under reduced pressure (40° C., 0.2 bar; 60 minutes), and drying at ambient temperature for a further 16 h afforded 23.5 g of purified material as a light orange syrup. The syrup was dissolved in THF (235 mL, 10 volumes) at 35-40° C. (10 minutes) and filtered through a 47 mm, 0.45 micron PTFE membrane (Merck-Millippore Omnipore). The filtrate was concentrated to half its original volume (100 mL, 4.3 volumes), and charged to a pressure equalizing dropping funnel upon returning to ambient temperature.

MTBE (400 mL, 19.5 volumes) was charged to a 3-neck RBF fitted with an internal temperature probe, and cooled to 0° C. with the aid of an external ice bath under an atmosphere of N$_2$. Upon reaching 0° C., addition of dendrimer commenced lasting 15 minutes (max. internal temperature 5° C.), whilst stirring continued for 45 minutes (at 0-5° C.) to allow ripening of the precipitate. Transferring the ensuing mixture to a Buchner vacuum filter (160 mm diameter) under N$_2$, afforded the first wet cake within 15 minutes. The filter cake was washed twice with 5 vol. MTBE (100 mL per wash) and pulled to dryness (under N$_2$) lasting a total of 15 minutes. The filter cake was transferred to a vacuum oven where drying took place at (25° C., 0.2 bar) until constant mass was achieved (48 h), affording free flowing white powder in 18.98 g (102% yield). HPLC (C8 Phenomenix Aeris, 2.1×100 mm, gradient: 5% ACN (0-1 min), 5-45% ACN/H$_2$O) (1-2 min), 45-60% ACN (2-8 min), 60% ACN (8-10 min), 60-90% ACN (10-10.1 min), 90% ACN (10.1-12 min), 90-5% ACN (12-15 min), 5% ACN (15-20 min), 272 nm, 10 mM ammonium formate) Rf (min)=14.94. $^1$H-NMR (300 MHz, CD$_3$OD) δ (ppm): 0.31-2.84 (m, 953H), 2.86-3.27 (m, 211H), 3.35 (s, 109H), 3.37-4.23 (m, 5734H), 4.24-4.64 (m, 95H), 6.26-8.41 (m, 632H). $^{19}$F-NMR (300 MHz, DMSO-d$_6$) δ: −107.1 ppm (3.64 mg, FBA, set integration to 100), −79.1 ppm (31.2 mg dendrimer, 108.82). This provides 8.91 mg Compound A (or 28.6% loading).

Example 10: Compound A Drug Loading of Dendrimers

The drug loading of Compound A in the dendrimers prepared in Examples 5-9 above were determined by NMR.

% Compound A Loading by $^1$H NMR:

Compound A loading was estimated via integration of the aromatic region (6.5-8.5 ppm), which was representative of Compound A, compared to the PEG region (3.4-4.2 ppm) which is representative of the dendrimer scaffold. In Example 5 shown in the table below, the theoretical number of protons for 32 Compound A groups, plus the residual BHA from the dendrimer is 650H. Only 631H were observed, indicating only 97% or 31 out of 32 sites were occupied by Compound A molecules. The % Compound A was then calculated by multiplying the MW (Compound A) by 31, then dividing by the total MW of the construct. i.e. Compound A loading=(945×31)/104,500=0.28 (or 28%).

% Compound A Loading by $^{19}$F NMR:

Compound A loadings were calculated by performing a $^{19}$F NMR of the conjugate using an internal standard (4-Fluorobenzoic acid, FBA). An experiment would typically be performed by accurately weighing out a known mass of dendrimer and FBA into a single vial. This would then be taken up in DMSO, sonicated (2 min) then analyzed by NMR (100 scans, 30 s delay time). The FBA and dendrimer peaks would then be integrated and the % Compound A calculated using molar ratios (3:1 mole ratio of Compound (3F) to FBA (1F).

TABLE 8

Percent Loading of Compound A on Lys Dendrimer

| Example | Scale | Compound A loading (%) | MW* (kDa) | No. of Compound A per dendrimer |
|---|---|---|---|---|
| 5 | 101 mg | 28.2 ($^1$H NMR) | 104.5 | 31 |
| 6 | Small Scale (98 mg) | 28.6 ($^1$H NMR) | 106.0 | 32 |
|   | Large Scale (74.8 g) | 25.1 ($^{19}$F NMR) | 96.2 | 27 |
| 7 | 137 mg | 28.8 ($^1$H NMR) | 105.6 | 32 |
| 9 | Small Scale (1.19 g) | 23.6 ($^{19}$F NMR) | 99.7 | 25 |
|   | Large Scale (18.98 g) | 28.6 ($^{19}$F NMR) | 101.6 | 31 |

*The total molecular weight can be estimated using the estimated MW of the dendrimer scaffold, the MW Compound A-linker and the % Compound A loading from NMR. i.e. for Example: MW = MW dendrimer scaffold − 32(MW TFA)/(100 −

Compound A loading %((Mr Compound A- linker − water)/Mr Compound A))/100

$$= \frac{75700 - 3648}{(100 - 28.2((1058 - 18)/945))/100}$$

$$= \frac{72052}{(100 - 28.2(1.10))/100}$$

$$= \frac{72052}{0.6898}$$

$$= \sim 104.5 \text{ kDa}$$

Example 11: In Vitro Release Study on Dendrimers (pH 7.4 in PBS 10% DMA)

Protocol:
1. Prepare PBS buffer—PBS prepared by dissolving 1 PBS tablet (Sigma, P4417) in 200 mL deionized water, providing 0.01 M phosphate buffer, 0.0027M potassium chloride and 0.137M sodium chloride at pH 7.4, 37° C.

2. Prepare 9:1 v/v PBS/DMA mixture by diluting 9 mL PBS buffer with 1 mL DMA.
3. Make up dendrimer solutions at 1 mg/mL in PBS/DMA mixture in 2 mL HPLC vials.
4. Monitor release of Compound A at room temperature by HPLC at 2 hourly intervals HPLC Method (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 243 nm, 10 mM ammonium formate).

TABLE 9a

Percent Compound A Released (Examples 5-8)

| time (h) | % Compound A released* | | | |
|---|---|---|---|---|
| | DGA PEG$_{2200}$ Example 7 | TDA PEG$_{2100}$ Example 6 | Glu PEG$_{2200}$ Example 5 | Glu PEG$_{1100}$ Example 8 |
| 0 | 0 | 0 | 0 | 0 |
| 0.5 | 10.1 | 5.2 | 0.43 | 0.44 |
| 2.5 | 62.7 | 24.8 | 2.65 | 1.86 |
| 4.5 | 80 | 39.5 | 4.38 | 2.96 |
| 6.5 | 81 | 50 | 5.96 | 4.35 |

*As judged by comparing the area under the peaks for Compound A (8.6 min) versus area under the peak for the dendrimer (10.8 min) by HPLC.

TABLE 9b

Percent Compound A Released (Example 9)

| time (h) | % Compound A released*,# MIDA PEG$_{2100}$ Example 9 |
|---|---|
| 0 | 1.43 |
| 2 | 10.59 |
| 4 | 17.54 |
| 6 | 23.71 |

*As judged by comparing the area under the peaks for Compound A (8.6 min) versus area under the peak for the dendrimer (10.8 min) by HPLC.
Example 9 was run as a separate experiment.

Example 12: In-Vitro Release Study on Dendrimers (pH 4.5 in 0.1M Citric Acid)

Protocol:

1. Prepare 0.1 M citric acid solution (7.68 g citric acid diluted to 400 mL with deionized water) and adjust pH to 4.5.
2. Make up dendrimer solutions at 1 mg/mL in citric acid solution in 2 mL HPLC vials.
3. Monitor release of Compound A at room temperature by HPLC at various time intervals. HPLC Method (C8 Xbridge, 3×100 mm, gradient: 42-50% ACN/H$_2$O) (1-7 min), 50-80% ACN (7-8 min), 80% ACN (8-11 min), 80-42% ACN (11-12 min), 42% ACN (12-15 min), 214 nm, 10 mM ammonium formate).

TABLE 10a

Percent Compound A Released (Examples 5-8)

| time (d) | % Compound A Released* | | |
|---|---|---|---|
| | DGA PEG$_{2200}$ Example 7 | TDA PEG$_{2100}$ Example 6 | Glu PEG$_{2200}$ Example 5 |
| 0 | 0 | 0 | 0 |
| 0.1 | 4.2 | 1.3 | 0.2 |
| 0.75 | 17.5 | 5.5 | 0.4 |
| 1.75 | 32.5 | 10.5 | 1.2 |
| 7 | 63 | 30 | 3.6 |

*As judged by comparing the area under the peaks for Compound A (8.6 min) versus area under the peak for the macromolecule (10.8 min) by HPLC.

TABLE 10b

Percent Compound A Released (Example 9)

| time (d) | % Compound A Released* MIDA PEG$_{2100}$ Example 9 |
|---|---|
| 0 | 1.83 |
| 2 | 33.87 |
| 5 | 65.03 |
| 7 | 80.7 |

*As judged by comparing the area under the peaks for Compound A (8.6 min) versus area under the peak for the macromolecule (10.8 min) by HPLC.
Example 9 was run as a separate experiment.

Example 13: DH Dependence of Initial Release of Compound A from Examples 6 and 9 into the Delivery Vehicle An HPLC-UV method was used to determine the rate of hydrolysis of Compound A from the macromolecule at pH 2.1, pH 3, pH 4, pH 5, pH 6, pH 7 and pH 8.

McIlvane buffer pH 2.2 was prepared by addition of 50 mL deionised water to 0.14 g of disodium phosphate dodecahydrate and 2.06 g of citric acid monohydrate. The solution was made to a total volume of 100 mL with deionised water and the pH confirmed.

McIlvane buffer pH 3 was prepared by addition of 50 mL deionised water to 1.47 g of disodium phosphate dodecahydrate and 1.67 g of citric acid monohydrate. The solution was made to a total volume of 100 mL with deionised water and the pH confirmed.

McIlvane buffer pH 4 was prepared by addition of 50 mL deionised water to 2.76 g of disodium phosphate dodecahydrate and 1.29 g of citric acid monohydrate. The solution was made to a total volume of 100 mL with deionised water and the pH confirmed.

McIlvane buffer pH 5 was prepared by addition of 50 mL deionised water to 3.69 g of disodium phosphate dodecahydrate and 1.02 g of citric acid monohydrate. The solution was made to a total volume of 100 mL with deionised water and the pH confirmed.

McIlvane buffer pH 6 was prepared by addition of 50 mL deionised water to 4.52 g of disodium phosphate dodecahydrate and 0.77 g of citric acid monohydrate. The solution was made to a total volume of 100 mL with deionised water and the pH confirmed.

McIlvane buffer pH 7 was prepared by addition of 50 mL deionised water to 5.90 g of disodium phosphate dodecahydrate and 0.37 g of citric acid monohydrate. The solution was made to a total volume of 100 mL with deionised water and the pH confirmed.

McIlvane buffer pH 8 was prepared by addition of 50 mL deionised water to 6.97 g of disodium phosphate dodecahydrate and 0.06 g of citric acid monohydrate. The solution was made to a total volume of 100 mL with deionised water and the pH confirmed.

1-2 mg of dendrimer was accurately weighed into a vial and 1 mL of buffer added. The sample was stirred magnetically at 37° C. for up to 130 h. The sample was analysed periodically by HPLC-UV. Free concentration of Compound A was determined by comparison of the HPLC-UV response of Compound A in the sample with the HPLC-UV response of a standard of known concentration.

TABLE 11

| HPLC method for Example 13 | |
|---|---|
| Standard Preparation: | 5 mg Comp. A in 10 mL 1:1 MeCN:Water |
| Column: | Waters XBridge C8, 50 × 4.6 mm, 2.7 μm |
| Column Temperature: | 40° C. |
| Injection volume (μL): | 5 μL (injector program bracketing of the sample with 5 μL of dimethylacetamide) |
| Detection wavelength: | |
| Flow rate (mL/min) | |
| Mobile Phase A (MPA): | 0.3% TFA in Water |
| Mobile Phase B (MPB): | 0.3% TFA in Acetonitrile |

| | Time (min) | % MPA | % MPB |
|---|---|---|---|
| Timetable: | 0 | | |

Figure 8:
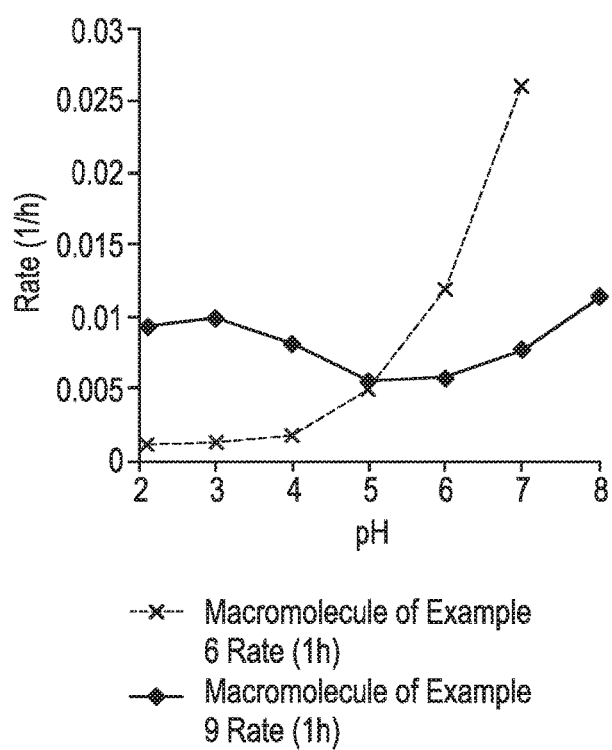
FIG. 8 is an initial release rate comparison of Example 6 and 9 across a range of pH values. See Example 13.

The rate constant at each pH was calculated from the observed solution concentrations over time using a least-squares fitting method. The observed rate constants are summarized in FIG. 8. The data show that Example 9 exhibited less variation in initial release across the pH range tested than Example 6.

Example 14: In Vitro Release of Compound A from Dendrimers in Rat and Mouse Plasma Protocol: To 0.5 mL of mouse (or rat) plasma (centrifuged and filtered) was added 0.1 mL of dendrimer solution (approximately 2 mg/mL Compound A equivalent in saline). The mixtures were vortexed (30 s) then incubated at 37° C. At various timepoints aliquots (0.1 mL) were removed and added to ACN (0.2 mL, 5% formic acid). The resulting mixtures were vortexed (30 s), centrifuged (10 min, 4° C.) filtered and analyzed by HPLC ((C8 Xbridge, 3×100 mm, gradient: 42-50% ACN/$H_2O$) (1-7 min), 50-80% ACN (7-8 min), 80% ACN (8-11 min), 80-42% ACN (11-12 min), 42% ACN (12-15 min), 243 nm, 10 mM ammonium formate, RT (Compound A)=6.7 min). For the mouse plasma experiment, the amount of Compound A was quantified against a Compound A standard and % released calculated by comparing released material to loaded material on the conjugate. For the rat plasma experiment, the release from DGA $PEG_{2200}$ (Example 7) at 22.5 hours was used as the standard and set to 100%. The results are summarized in Tables 12a and 12b.

TABLE 12a

Results of in vitro release of Compound A in rat plasma

| | % Compound A Released in Rat plasma at 37 C.* | | | | |
|---|---|---|---|---|---|
| time (h) | DGA $PEG_{2200}$ Example 7 | TDA $PEG_{2100}$ Example 6 | MIDA $PEG_{2100}$ Example 9 | Glu $PEG_{2200}$ Example 5 | Glu $PEG_{1100}$ Example 8 |
| 0 | 0 | 0 | 0 | 0 | 0 |
| 0.5 | 32 | 6 | 3 | 0.3 | 0.2 |
| 2.5 | 93 | 31 | 9 | 3.5 | 2.6 |
| 4.5 | 96 | 49 | 14 | 4.8 | 4.5 |
| 22.5 | 100 | 89.5 | 57 | 25.3 | 21 |

*All data is Normalised against DGA $PEG_{2200}$ (Example 7) and assumes that there is full release in this sample.

TABLE 12b

Results of in vitro release of Compound A in mouse plasma

| | % Compound A Released in Mouse plasma at 37 C.* | | | | |
|---|---|---|---|---|---|
| time (h) | DGA $PEG_{2200}$ Example 7 | TDA $PEG_{2100}$ Example 6 | MIDA $PEG_{2100}$ Example 9 | Glu $PEG_{2200}$ Example 5 | Glu $PEG_{1100}$ Example 8 |
| 0 | 0 | 0 | 0 | 0 | 0 |
| 0.5 | 32.6 | 9.1 | 2.1 | 0.9 | 1.4 |
| 2.5 | 70.8 | 33.2 | 6.7 | 2.9 | 2.8 |
| 4.5 | 76.1 | 50.6 | 11.3 | 5.8 | 4.3 |
| 22.5 | 87.5 | 88.4 | 46.5 | 22.9 | 22.1 |

*Measured against a standard solution of Compound A

Example 15: Dendrimer Solubility in pH 7.4 and pH 4.5

Protocol:
1. Accurately weigh 10 mg of dendrimer into a vial
2. Carefully add aliquots of buffer to the vial to achieve dissolution. Note: the mixture was gently swirled for several minutes between aliquots. Sonication was also used to aid dissolution.

TABLE 13

Results of solubility studies at ph 7.4 and pH 4.5

| Linker | Molecular weight (kDa) | Weight % of Compound A (from NMR) | Solubility at pH 7.4 in PBS Dendrimer mg/mL (Compound A mg/ml) | Solubility at pH 4.5 in 0.1M citric acid Dendrimer mg/mL (Compound A mg/ml) |
|---|---|---|---|---|
| Example 5 | 104.5 | 28.2 | 158 (44.5) | 162 (45.7) |
| Example 6 | 106.0 | 28.6 | 153 (43.6) | 141 (40.2) |
| Example 7 | 105.6 | 28.8 | 142 (41.0) | 157 (45.2) |
| Example 8 | 76.7 | 39.4 | 125 (49.3) | 121.3 (48.0) |

Example 16: Dendrimer Solubility at pH 4 and pH 5

A visual method was used to determine solubility of the dendrimers in aqueous buffers. Data represent single experiments.

McIlvane buffer pH 5 was prepared by addition of 50 mL deionised water to 3.69 g of disodium phosphate dodecahydrate and 1.02 g of citric acid monohydrate. The solution was made to a total volume of 100 mL with deionised water and the pH confirmed.

McIlvane buffer pH 4 was prepared by addition of 50 mL deionised water to 2.76 g of disodium phosphate dodecahydrate and 1.29 g of citric acid monohydrate. The solution was made to a total volume of 100 mL with deionised water and the pH confirmed.

1 mL of buffer was added to a glass vial and a magnetic stirrer added. Dendrimer was added in aliquots to the vial whilst stirring. Both dendrimers of Examples 6 and 9 achieved complete dissolution after addition of ca. 250 mg, after which the solution was too viscous to adequately stir. Solubility is reported as grams of solute per gram of solution and assumes the density of the buffer is 1 g/mL.

TABLE 14

Results of solubility studies at pH 4 and pH 5

| Example | Buffer | Visual observation of solubility | Compound A equivalent |
| --- | --- | --- | --- |
| Example 6 | McIlvane buffer, pH 4 | >0.189 g/g | >0.048 g/g |
| Example 9 | McIlvane buffer, pH 5 | >0.224 g/g | >0.064 g/g |

Example 17: Dendrimer Formulations

1. Formulations for Rat Telemetry Studies

Vials containing the appropriate amount of lyophilized dendrimer were selected. Approximately 0.5-1 mL of phosphate buffered saline (PBS) was then added to each vial and the vials vortexed until the dendrimer was in solution. The contents of each vial were combined and transferred to a single vial with rinsing with the remaining PBS to make to volume. With the exception of Example 8, formulations were prepared at room temperature. Formulations containing Example 8 were warmed gently in a water bath set to 40° C. to aid dispersion of Example 8 in the vehicle. All formulations were dosed immediately, at least within 30 minutes of preparation. A summary of the PBS formulations is found in Table 15a.

TABLE 15a

PBS Formulations of Examples 5, 6 and 8 for rat telemetry studies

| Ingredients | Example 5 (2 mg/mL Compound A equivalent) | Example 5 (6 mg/mL Compound A equivalent) | Example 6 (2 mg/mL Compound A equivalent) | Example 6 (4 mg/mL Compound A equivalent) |
| --- | --- | --- | --- | --- |
| Phosphate buffered saline | ~9.5 mL | ~9.5 mL | ~9.5 mL | ~9.5 mL |
| Dendrimer | 67 mg | 201 mg | 67 mg | 134 mg |

| Ingredients | Example 6 (6 mg/mL Compound A equivalent) | Example 8 (2 mg/mL Compound A equivalent) | Example 8 (6 mg/mL Compound A equivalent) |
| --- | --- | --- | --- |
| Phosphate buffered saline | ~9.2 mL | ~9.5 mL | ~10.3 mL |
| Dendrimer | 194 mg | 67 mg | 218 mg |

Citrate-phosphate (McIlvaine) buffer pH4 was prepared. Per 100 mL buffer, 1.29 g citric acid monohydrate and 2.76 g sodium phosphate dibasic dodecahydrate were weighed into a cylinder and 95 mL of water for injection was added. The vehicle was stirred (or sonicated) to dissolve. The pH was then measured and adjusted to pH 4 with 0.1M HCl or NaOH, as required. The vehicle was made to volume with water for injection.

Vials containing the appropriate amount of lyophilized dendrimer were selected. 0.5-1 mL of citrate-phosphate (McIlvaine) buffer pH4 was then added to each vial and the vials mixed, with vortexing if needed, until the macromolecule was in solution. The contents of each vial were combined and transferred to a single vial with rinsing with the remaining PBS to make to volume. They were dosed immediately, at least within 30 minutes of preparation. A summary TABLE 15b Formulations of Example 9 for rat telemetry studies

| Ingredients | Example 9 (2 mg/mL Compound A equivalent) | 22.6 mg/mL Example 9 (6 mg/mL Compound A equivalent) |
| --- | --- | --- |
| McIllvanes Citrate/Phosphate buffer, pH4 | ~8 mL | ~8 mL |
| Dendrimer | 60 mg | 181 mg |

2. Formulations for Precipitation (Solubility) Studies

Citrate-phosphate buffer preparation: The following method was used to prepare citrate/phosphate buffers. The appropriate quantity of citric acid and sodium phosphate dibasic dodecahydrate were weighed into a 100 mL volumetric flask and 95 mL of water for injection added, followed by stirring (or sonication). The pH of the resultant solution was adjusted to the target pH (i.e. 4 or 5) and the buffer made to volume with water for injection (i.e. 100 mL).

TABLE 15c

Citrate-phosphate (McIlvaine) buffer composition, per 100 ml buffer for precipitation (solubility) studies

| Example | Buffer pH | Citric acid monohydrate/grams | Sodium phosphate dibasic dodecahydrate/grams |
| --- | --- | --- | --- |
| Example 6 | 4 | 1.29 | 2.76 |
| Example 9 | 5 | 1.02 | 3.69 |

Vehicle Preparation:

Citrate-phosphate (McIlvaine) buffers, outlined in Table 15c, were used to prepare the dilute buffered vehicles by performing a 1:10 dilution with 5% w/v glucose, in the presence or absence of 1% w/v Kolliphor HS-15 (polyethylene glycol (15)-hydroxystearate).

Commercially-available 5% w/v glucose solution was added to approximately 90% of the target volume. For diluted buffer vehicles containing Kolliphor, a quantity of Kolliphor HS-15 equivalent to 1% w/v was added and the vehicle stirred to dissolve the Kolliphor HS-15. Subsequently, the pH was adjusted to target pH with 0.1M HCl or NaOH (if required). The vehicles were then made to volume with 5% w/v glucose and filtered using a 0.22 μm pore-sized PVDF syringe filter.

Formulation Preparation:

Formulations containing Example 6 and Example 9 (in the presence or absence of Kolliphor HS-15) were prepared on a 5 mL scale in dilute buffered vehicle, in duplicate (n=2), at the concentrations indicated in Table 15d below:

TABLE 15d

Formulations containing Examples 6 and 9 with and without Kolliphor

| Example | Compound A conc. (mg/mL) | Dendrimer conc. (mg/mL) | Formulation pH |
|---|---|---|---|
| Example 6 | 0.74 | 3 | 4 |
| Example 6 | 24.8 | 100 | 4 |
| Example 9 | 0.9 | 3 | 5 |
| Example 9 | 28.6 | 100 | 5 |

In order to prepare the formulations, the appropriate quantity of dendrimer was weighed into a suitable container with a magnetic stirrer. Whilst the magnetic stirrer was in operation, dilute buffered vehicle (pH 4 or pH 5 citrate/phosphate buffer diluted 1:10 with 5% w/v glucose containing 1% w/v Kolliphor HS-15) was added to achieve 95% of the target volume. The formulation was continually stirred to aid dissolution, avoiding generation of excessive foaming, until a clear solution was formed and the pH adjusted. Subsequently, the formulation was made to volume (5 mL) with dilute buffered vehicle, and the final pH recorded.

Assessment of Precipitation Kinetics:

The formulation was stored at room temperature and protected from light and samples were visually assessed using a Seidenader and light box at 0, 3, 6, 24, 48, 72 and 96 hour timepoints to rule out the presence of visible particulate matter. Table 15e provides a summary of visual assessment observations.

TABLE 15e

Summary of precipitation observations

| Example | Dendrimer conc. (mg/mL) | Comments |
|---|---|---|
| Example 6 (+Kolliphor HS15) | 3 | No ppt observed up to seven days |
| | 100 | No ppt observed up to seven days |
| Example 6 (−Kolliphor HS15) | 3 | No ppt observed up to seven days |
| | 100 | No ppt observed up to seven days |
| Example 9 (+Kolliphor HS15) | 3 | No ppt observed up to 96 hours |
| | 100 | Onset of ppt 42 hours |
| Example 9 (−Kolliphor HS15) | 3 | No ppt observed up to 96 hours |
| | 100 | Onset of oat 42 hours |

Given the very low aqueous solubility of Compound A, observed precipitation was expected over a much shorter timeframe.

3. Formulations for Toxicology Studies

Formulations for Toxicological Studies of Example 6:

Example 6 was formulated in a pH 4 citrate-phosphate buffer diluted 1:10 with 5% glucose and containing 1% w/v Kolliphor HS-15 (polyethylene glycol (15)-hydroxystearate), at concentrations up to 121 mg/mL of Example 6 (up to Compound A concentration of 30 mg/mL).

Citrate-Phosphate Buffer Preparation:

The appropriate quantity of citrate-phosphate (McIlvaine) buffer pH4 was prepared as outlined in Table 14 above.

Vehicle Preparation:

Citrate-phosphate buffer, pH 4 (as per Table 15c) was used to prepare the dilute buffered vehicle by performing a 1:10 dilution with 5% w/v glucose, in the presence of 1% w/v Kolliphor HS-15, as outlined in the preceding section.

Formulation Preparation:

pH 4 citrate/phosphate buffer diluted 1:10 with 5% glucose and containing 1% w/v Kolliphor HS-15 was used to prepare Example 6 formulations as outlined in the preceding section.

Formulations of Example 6 were prepared at room temperature and dosed within 60 minutes of preparation. Formulations containing between 4 mg/mL and 25 mg/mL Example 6 (equivalent to 1 mg/mL and 6.2 mg/mL of Compound A) were prepared. Volumes ranged from 15 mL to 47 mL. To rule out the presence of particles, the formulation was visually assessed.

Formulations for Toxicological Studies of the Macromolecule of Example 9:

Example 9 was be formulated in a pH 5 citrate-phosphate buffer diluted 1:10 with 5% glucose and containing 1% w/v Kolliphor HS-15 (polyethylene glycol (15)-hydroxystearate), at concentrations from 3.1 mg/mL to 105 mg/mL of Example 9 (equivalent to a concentration of Compound A of 0.9 mg/mL and 30 mg/mL).

Citrate-Phosphate Buffer Preparation:

100 mL citrate-phosphate (McIlvaine) buffer pH 5 was prepared, as outlined in the preceding section.

Vehicle Preparation:

Citrate-phosphate (McIlvaine) buffer, pH 5 (as per example 16b) was used to prepare the dilute buffered vehicle by performing a 1:10 dilution with 5% w/v glucose, in the presence of 1% w/v Kolliphor HS-15, as outlined in the preceding section.

Formulation Preparation:

pH 5 citrate-phosphate buffer diluted 1:10 with 5% glucose and containing 1% w/v Kolliphor HS-15 was used to prepare Example 9 formulations, as outlined in the preceding section. To rule out the presence of particles, the formulation was visually assessed.

Formulations of Example 9 were prepared at room temperature and dosed within 75 minutes of preparation. Formulations containing between 12.5 mg/mL and 100 mg/mL of Example 9 (equivalent to a Compound A concentration of 3.6 mg/mL and 28.6 mg/mL) were prepared. Volumes ranged from 6 mL to 18 mL.

Example 18: Rat and Mouse Efficacy Studies

The formulations used in the efficacy studies were prepared as follows:

Preparation of Examples 6 and 9 Macromolecule PBS Formulations for Dosing RS4;11 Efficacy Study:

The appropriate amount of Examples 6 or 9 were weighed into a volumetric flask. 10 mL Dulbecc's Phosphate Buffered Saline (PBS) was added and formulations were then stirred until the compound dissolved entirely. See also preparation of formulations for rat telemetry studies in Example 17a.

Formulations of Example 6 for Dosing in SuDHL-4 Efficacy Study:

The macromolecule of Example 6 can be formulated in a pH 4 citrate/phosphate buffer diluted 1:10 with 5% Glucose and containing 1% w/v Kolliphor HS-15, at concentrations up to 121 mg/mL of Example 6 (equivalent of up to 30 mg/mL of Compound A concentration).

100 ml McIlvane citrate/phosphate buffer pH4 was prepared. 1.29 g Citric acid monohydrate and 2.76 g sodium phosphate dibasic dodecahydrate were weighed into a vial and 95 mL of water for injection was added. The vehicle was stirred (or sonicated) to dissolve. The pH was then measured and adjusted to pH 4 with 0.1M HCl or NaOH, as required. The vehicle was made to volume (100 mL) with Water for Injection.

This McIlvane buffer was used to prepare the diluted buffer vehicle (pH 4 citrate/phosphate buffer diluted 1:10 with 5% glucose and containing 1% w/v Kolliphor HS-15).

The required amount of McIlvane citrate/phosphate buffer, equivalent to 10% of the total target volume to be prepared, was added to a suitable container. Commercially available 5% glucose solution was added to approximately 90% of the target volume. Kolliphor HS-15 equivalent to 1% w/v was added and the vehicle stirred to dissolve the Kolliphor HS-15. pH was measured and adjusted to pH 4.0±0.05 with 0.1M HCl or NaOH (if required). The vehicle was then made to volume with 5% glucose. It was filter sterilized using a 0.22 μm pore size syringe filter, if necessary.

To prepare the formulation of Example 6 for the higher dose (10 mg/ml Compound A or Example 6 equivalent of 39 mg/mL), 390 mg of Example 6, equivalent to 100 mg Compound A, was transferred into a suitable container with a magnetic stirrer. Whilst the magnetic stirrer was in operation, diluted buffer vehicle (pH 4 citrate/phosphate buffer that has been diluted 1:10 with 5% glucose containing 1% w/v Kolliphor HS-15) was added to 95% of the target volume (9.5 mL). Stirring of the formulation was continued to aid dissolution, avoiding generation of excessive frothing, until a clear solution was formed. The formulation was then made to volume (0.5 mL) with diluted buffer vehicle and the pH checked. The formulation was assessed visually to rule out the presence of particles. 2 and 6 mg/ml were prepared from the higher concentration.

Formulations of Example 6 were prepared at room temperature and dosed within 5 minutes of preparation. Their preparations were as previously described in Example 17 (Formulations for toxicological studies).

Formulations for Macromolecule of Example 9 for SuDHL-4 Efficacy Study:

Example 9 was formulated in a pH 5 citrate/phosphate buffer diluted 1:10 with 5% glucose and containing 1% w/v Kolliphor HS-15, at concentrations up to 105 mg/mL of Example 9 (equivalent to up to 30 mg/mL of Compound A concentration).

100 ml McIlvane citrate/phosphate buffer pH 5 was prepared. 1.02 g citric acid monohydrate and 3.69 g sodium phosphate dibasic dodecahydrate were weighed into a vial and 95 mL of water for injection was added. The vehicle was stirred (or sonicated) to dissolve. The pH was then measured and adjusted to pH 5 with 0.1M HCl or NaOH, as required. The vehicle was made to volume (100 mL) with Water for Injection.

This McIlvane buffer was used to prepare the diluted buffer vehicle (pH 5 citrate/phosphate buffer diluted 1:10 with 5% glucose and containing 1% w/v Kolliphor HS-15). The required amount of McIlvanes citrate/phosphate buffer, equivalent to 10% of the total target volume to be prepared, was added to a suitable container. Commercially available 5% glucose solution was added to approximately 90% of the target volume. Kolliphor HS-15 equivalent to 1% w/v was added and the vehicle stirred to dissolve the Kolliphor HS-15. pH was measured and adjusted to pH 5.0±0.05 with 0.1M HCl or NaOH (if required). The vehicle was then made to volume with 5% glucose. It was filter sterilized using a 0.22 μm pore size syringe filter, if necessary.

To prepare the formulation of Example 9 for the higher dose (10 mg/ml Compound A or Example 9 equivalent of 37 mg/mL), 370 mg of Example 9, equivalent to 100 mg Compound A, was transferred into a suitable container with a magnetic stirrer. Whilst the magnetic stirrer was in operation, diluted buffer vehicle (pH 4 citrate/phosphate buffer that has been diluted 1:10 with 5% glucose containing 1% w/v Kolliphor HS-15) was added to 95% of the target volume (9.5 mL). Continued stirring to aid dissolution, avoiding generation of excessive frothing, until a clear solution was formed. The formulation was then made to volume (0.5 mL) with diluted buffer vehicle and the pH checked. The formulation was assessed visually to rule out the presence of particles. 2 and 6 mg/ml were prepared from the higher concentration.

Formulations of Example 9 were prepared at room temperature and dosed within 5 minutes of preparation.

Figure 9:
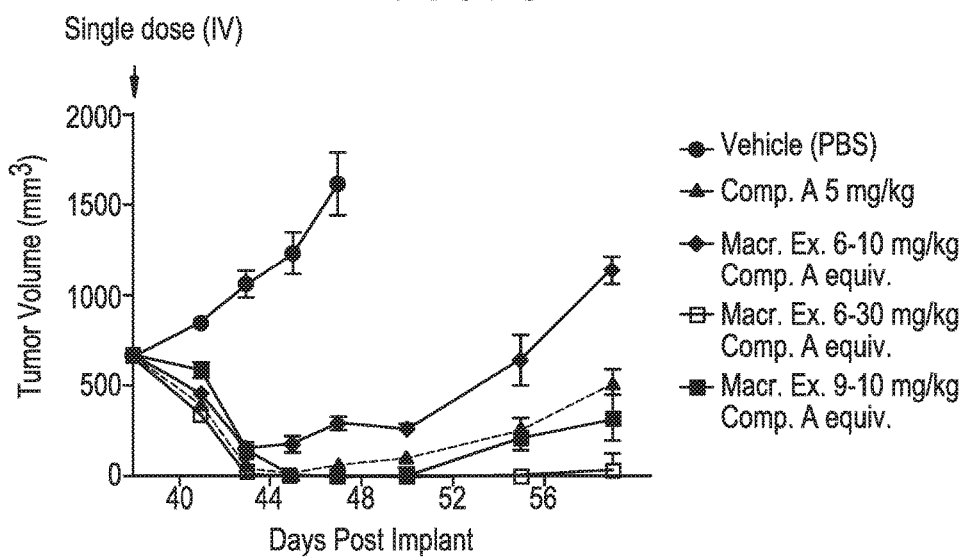
FIG. 9 displays an Acute Lymphoblastic Leukemia (ALL) Xenograft model in SCID mice using human acute lymphoblastic leukemia cells (RS4:11) for various macromolecules of the present invention. The efficacy evaluation of the vehicle (phosphate buffer saline), Compound A (formulated in 30% HP-β-CD, pH 4), Example 6 in PBS (equivalent to 10 mg/kg and 30 mg/kg Compound A), Example 9 in PBS (equivalent to 10 mg/kg and 30 mg/kg Compound A) is shown. See Example 18.

Efficacy of Examples 6 and 9 in RS4;11 Xenograft Model:

$5 \times 10^6$ RS4;11 cells in a total volume of 100 μl were inoculated subcutaneously at the mouse right flank. When the tumor volume reached approximately ~350 mm³, tumor-bearing mice were randomized into groups of 4 animals and treated with either control Vehicle (PBS) or treatment. FIG. 9 shows that with different release rates, the dendrimers exhibit differing efficacy. Example 6 at 30 mg/kg Compound A equivalent and Example 9 at 10 mg/kg Compound A equivalent with single IV dose have shown similar or slightly better activity than the Compound A HP-β-CD 10 mg/kg IV once, (100%, 98% vs. 90% regression, respectively).

TABLE 16

Summary of inhibition and regression data for Examples 6 and 9

| Group Number | Treatment | Efficacy | | | |
| --- | --- | --- | --- | --- | --- |
| | | % Inhibition Day (47) | % Regression Day(47) | P-value Day (47) | T-C (Days) |
| 1 | Vehicle | | | | |
| 2 | Compound A 5 mg/kg | >100 | 90 | <0.0001 | |
| 3 | Example 6 10 mg/kg Compound A equivalent (39 mg/kg macromolecule) | >100 | 56 | <0.0001 | |
| 4 | Example 6 30 mg/kg Compound A equivalent (117 mg/kg macromolecule) | >100 | 100 | <0.0001 | >32 |
| | Example 9 10 mg/kg Compound A equivalent (37 mg/kg macromolecule) | >100 | 98 | 0.0085 | |

Figure 10:
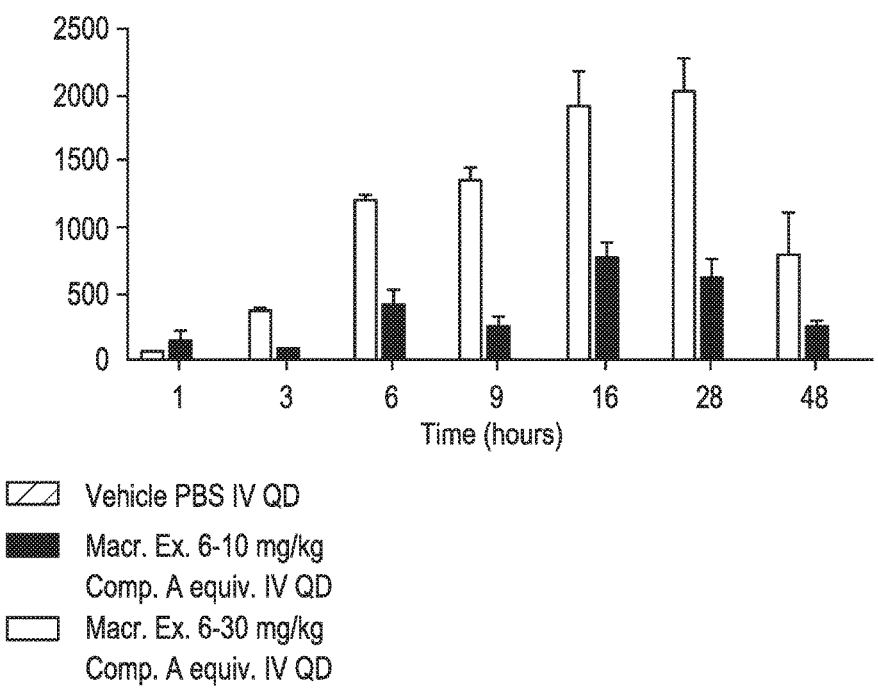
FIG. 10 displays the cell death (apoptosis) at various time points post a single dose of either vehicle (phosphate buffered saline) or Example 6 in PBS (equivalent to 10 and 30 mg/kg Compound A). Cleaved Caspase 3 (CC3) response was used as a measure of cell death and was determined using the Cell Signaling Pathscan ELISA Kit. See Example 18.

When RS4;11 tumor volume reached approximately ~400-600 mm³, groups of 3 tumor-bearing mice were treated with a single dose of either vehicle (PBS) or Example 6 I.V at 10 and 30 mg/kg. Tumors were collected at different time-points post-dose and processed for analysis. Results shows that the linker induces comparable apoptotic response as indicated by cleaved Caspase 3, the responses were peaked at 16-28 hr post dose (FIG. 10). Example 6 at 30 mg/kg Compound A equivalent (117 mg/kg Example 6) induced the highest CC3 response.

Figure 11:
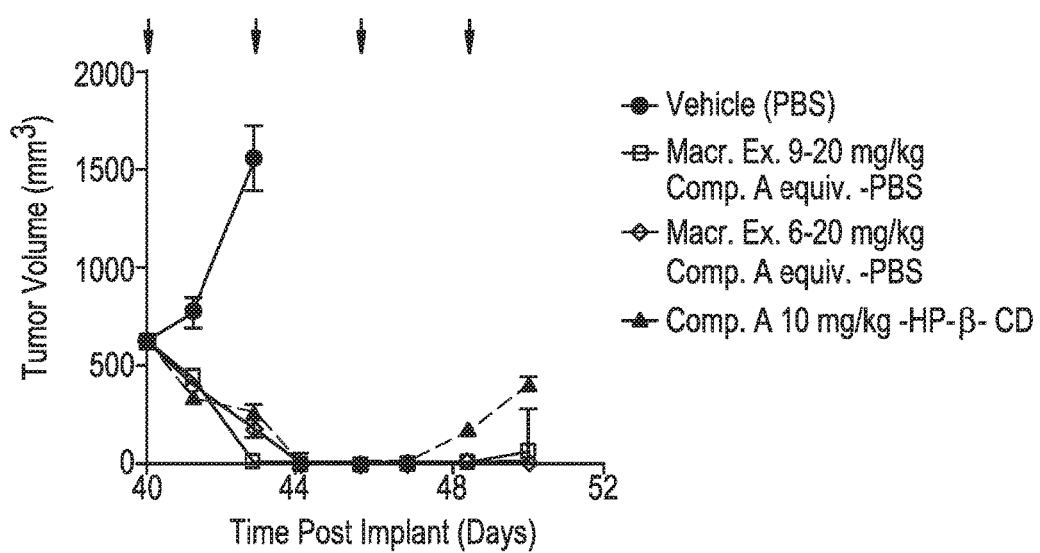
FIG. 11 displays an Acute Lymphoblastic Leukemia (ALL) Xenograft model in SCID mice using human acute lymphoblastic leukemia cells (RS4:11) for the various disclosed dendrimers. The efficacy evaluation of the vehicle (phosphate buffer saline, PBS), a formulation of Compound A in Vehicle 1 (30% HP-β-CD), Example 6 in PBS (equivalent to 20 mg/kg Compound A) and Example 9 in PBS (equivalent to 20 mg/kg Compound A) is shown. See Example 18.

FIG. 11 shows that Example 9 and Example 6 dosed at 20 mg/kg Compound A equivalent (74 and 78 mg/kg of dendrimer, respectively) were slightly more efficacious than Compound A in the HP-β-CD formulation (see Example 2) at 10 mg/kg weekly.

Figure 12:
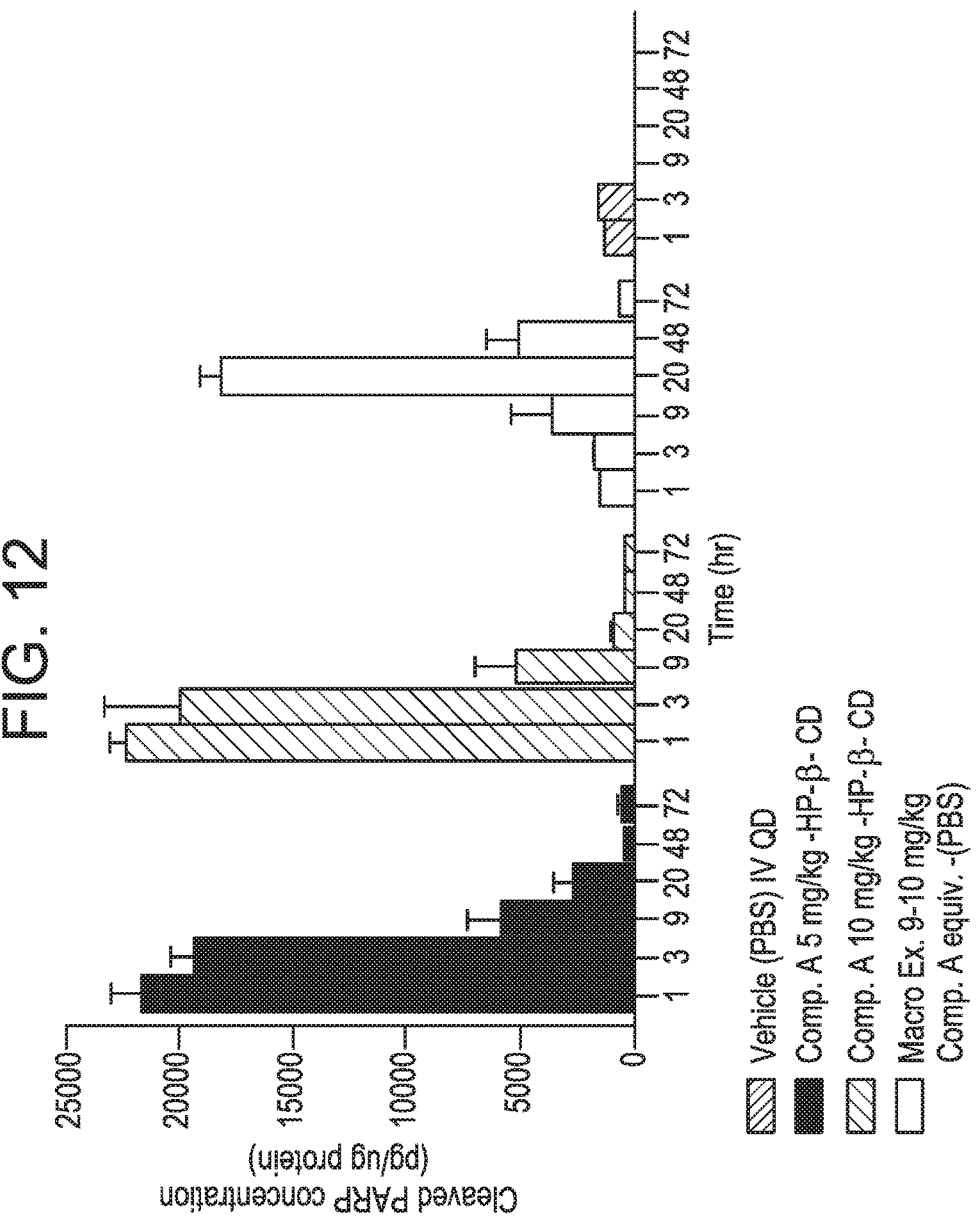
FIG. 12 displays the cell death (apoptosis), at various time points after a single dose of the vehicle (phosphate buffered saline), formulations of Compound A in vehicle 1 (30% HP-β-CD) at 5 mg/kg and 10 mg/kg and the dendrimer of Example 9 in PBS at 10 mg/kg Compound A equivalent. Cleaved poly ADP ribose polymerase (PARP) response was used as a measure of cell death. See Example 18.

Additionally, cell death (apoptosis) was measured using cleaved PARP (FIG. 12). Compound A in the HP-β-CD (see Example 2) formulation induced cleaved PARP immediately post treatment 1 and 3 hr, while Example 9 caused cell death maximum cell death at 20 hr post single dose.

Figure 13:
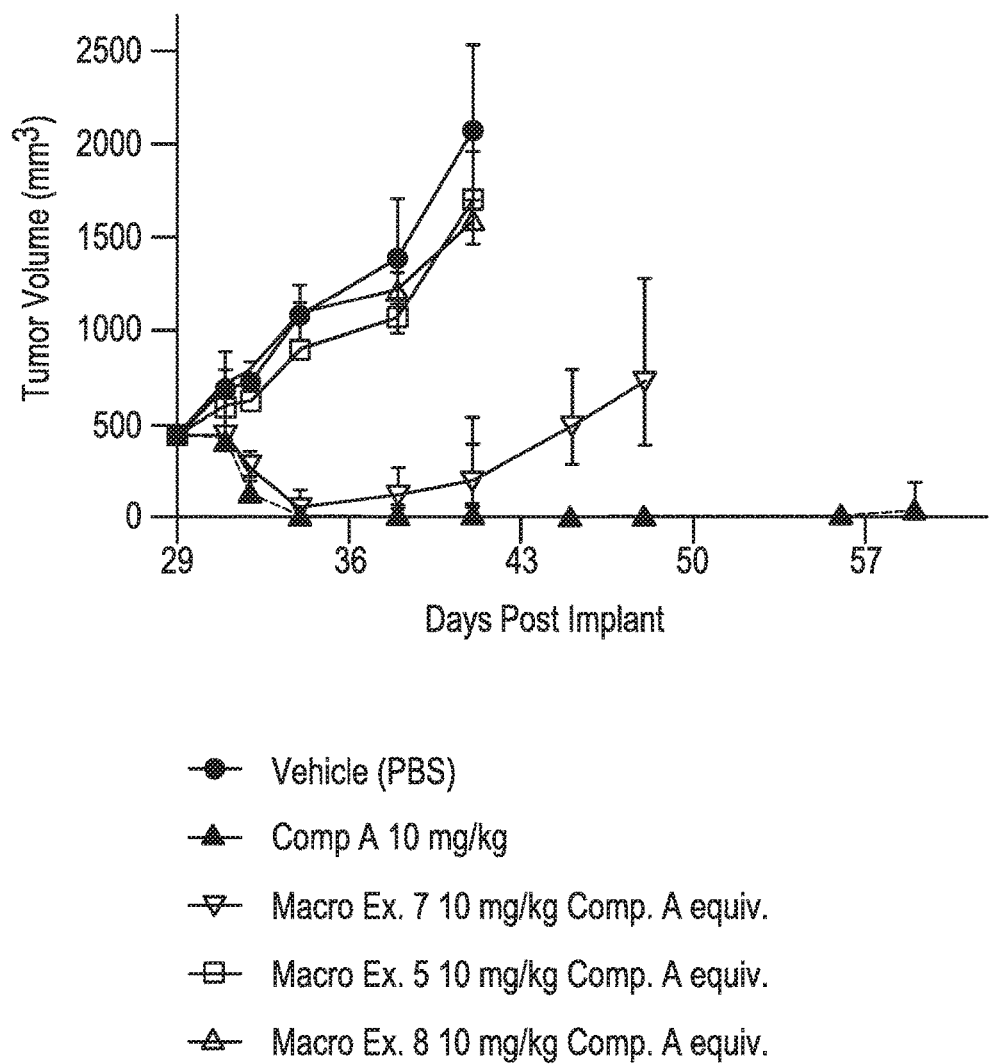
FIG. 13 displays data for Examples 5, 7 and 8 dosed at 10 mg/kg Compound A equivalent in the RS4;11 Xenograft mouse model. The data demonstrates that Example 7 dosed at 10 mg/kg Compound A equivalent induces tumor regression whereas Examples 5 and 8 dosed at 10 mg/kg Compound A equivalent did not show as significant anti-tumor activity. See Example 18.

Efficacy of Example 5, 7 and 8 in RS4;11 Xenograft Model in Mice:

Examples 5, 7 and 8 were formulated in PBS and dosed at 10 mg/kg Compound A equivalent in the RS4;11 Xenograft mouse model. FIG. 13 demonstrates that Example 7 dosed at 10 mg/kg Compound A equivalent induces tumor regression whereas Example 5 and 8 dosed at 10 mg/kg Compound A equivalent did not show as significant antitumor activity.

Figure 14:
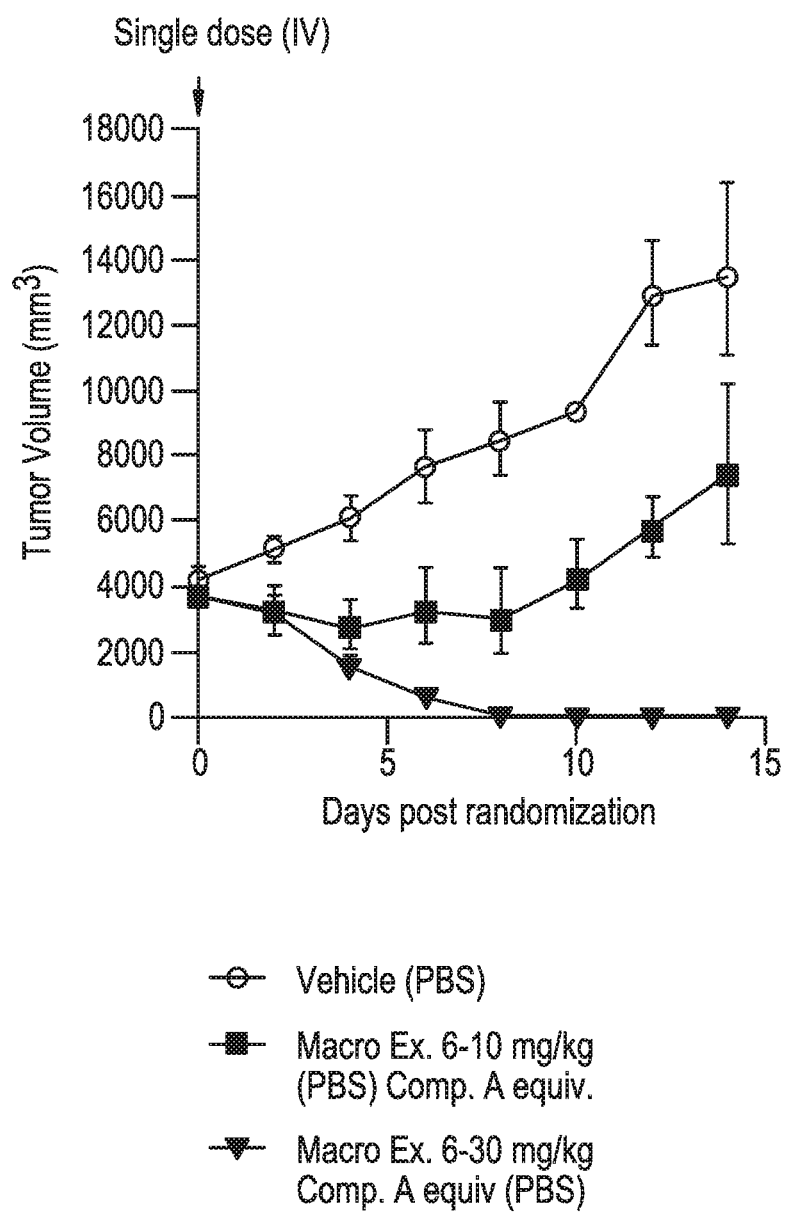
FIG. 14 displays an Acute Lymphoblastic Leukemia (ALL) Xenograft model in Rag2−/− rats using human acute lymphoblastic leukemia cells (RS4:11) for Example 6 and the vehicle. The efficacy evaluation of the vehicle (phosphate buffer saline, PBS) and Example 6 in PBS (equivalent to 10 mg/kg and 30 mg/kg Compound A) is shown. See Example 18.

Efficacy of Example 6 in RS4;11 Xenograft Model in Rag2−/− Rat:

FIG. 14 shows that Example 6 dosed at 30 mg/kg Compound A equivalent (117 mg/kg macromolecule) causes regression of RS4;11 tumor. 10 mg/kg Compound A equivalent (39 mg/kg Example 6) single dose of Example 6 inhibited tumor growth (stasis).

Examples 6 and 9 Enhance Inhibition of Tumor Growth by Rituximab in SuDHL-4 Xenograft Model in SCID Mice:

The SuDHL-4 xenograft model was used to test the ability of Examples 6 and 9 to enhance the activity of rituximab in inhibiting tumor growth. When tumors grew to approximately 175-250 mm$^3$, mice were randomized to the following groups:

(1) vehicle control group;
(2) Example 6 treatment group (50 mg/kg Compound A equivalent, 195 mg/kg Example 6, i.v. once a week for 5 weeks);
(3) Example 9 treatment group (50 mg/kg, Compound A equivalent, 185 mg/kg Example 9, i.v. once a week for 5 weeks;
(4) rituximab group (10 mg/kg i.p. once a week for 5 weeks);
(5) Example 6 (10 mg/kg Compound A equivalent, 39 mg/kg Example 6) plus rituximab;
(6) Example 6 (30 mg/kg Compound A equivalent, 117 mg/kg Example 6) plus rituximab;
(7) Example 6 (50 mg/kg Compound A equivalent, 195 mg/kg Example 6) plus rituximab.
(8) Example 9 (10 mg/kg Compound A equivalent, 37 mg/kg Example 9) plus rituximab;
(9) Example 9 (30 mg/kg Compound A equivalent, 111 mg/kg Example 9) plus rituximab;
(10) Example 9 (50 mg/kg Compound A equivalent, 185 mg/kg Example 9) plus rituximab;

The tumor sizes were measured 2 times a week and calculated as: Tumor Volume=$(A \times B^2)/2$ where A and B are the tumor length and width (in mm), respectively.

Figure 15:
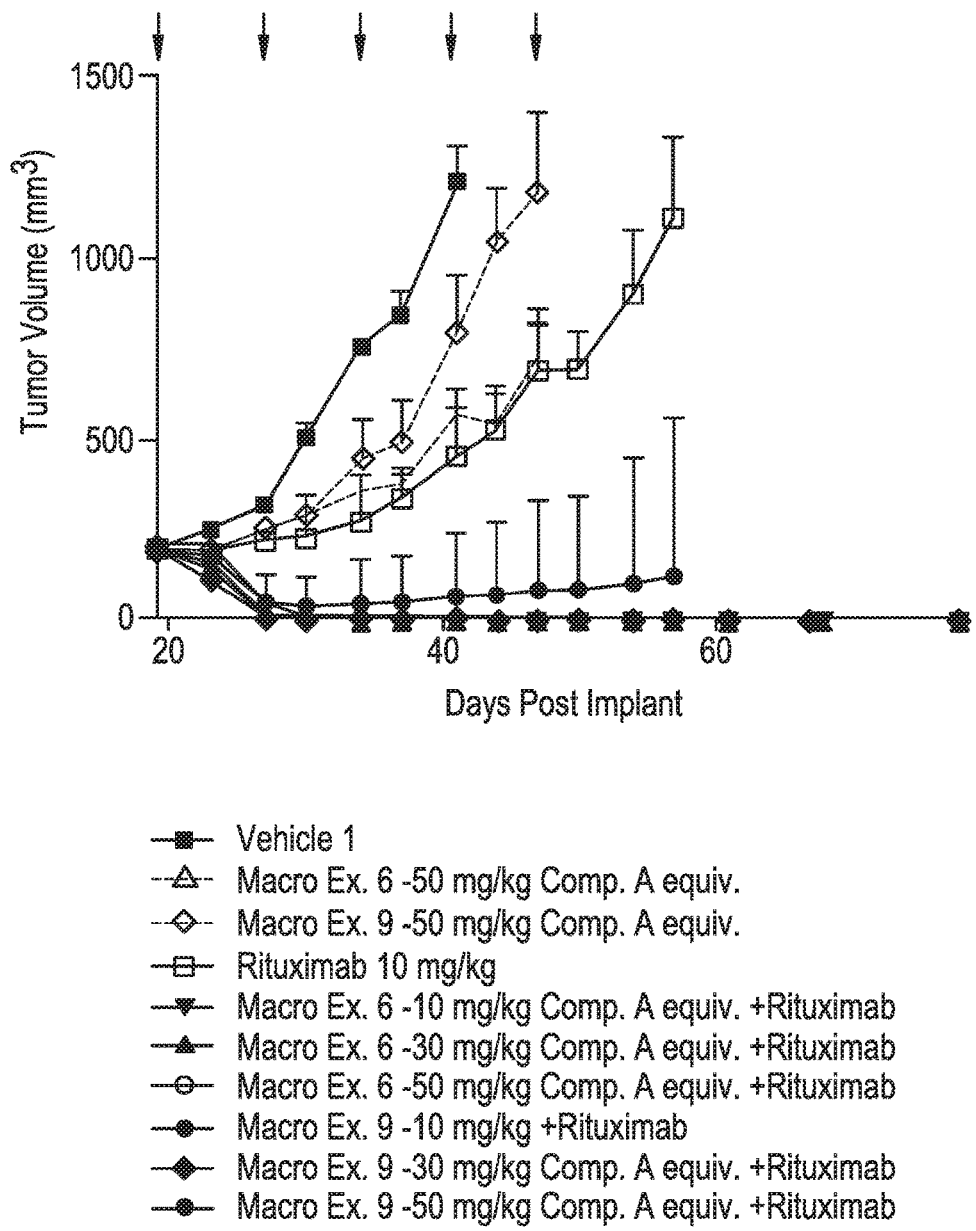
FIG. 15 displays a SuDHL-4 Xenograft Model in SCID mice for the vehicle (phosphate buffer saline, PBS), Example 6 in PBS (equivalent to 50 mg/kg Compound A), Example 9 in PBS (equivalent to 50 mg/kg Compound A), rituximab (10 mg/kg), a combination of Example 6 (10 mg/kg, 30 mg/kg and 50 mg/kg Compound A equivalent) with rituximab (10 mg/kg), and a combination of Example 9 (10 mg/kg, 30 mg/kg and 50 mg/kg Compound A equivalent) with rituximab (10 mg/kg). See Example 18.
Figure 16:
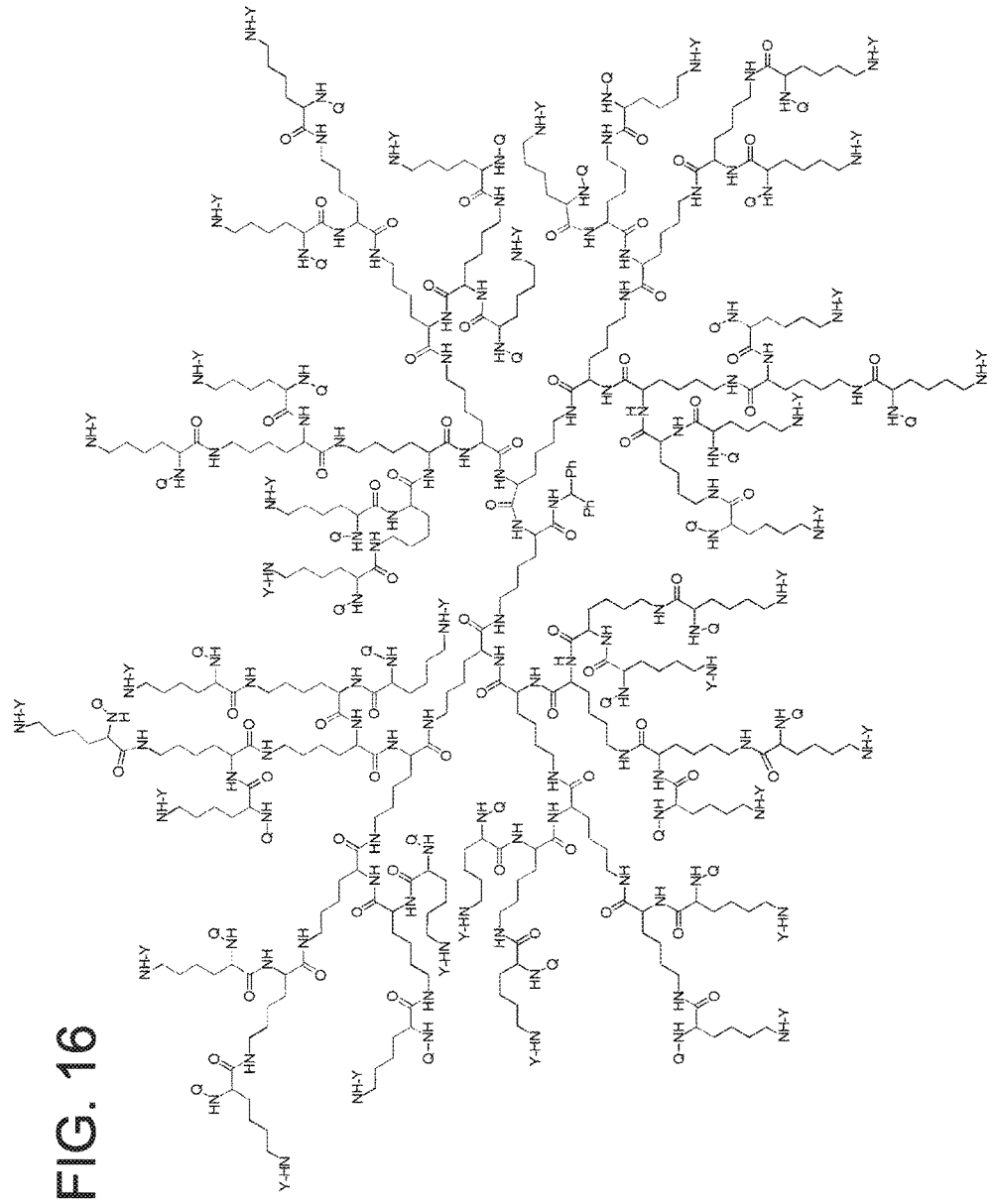
FIG. 16 displays the dendrimer of formula (IV).
Figure 17:
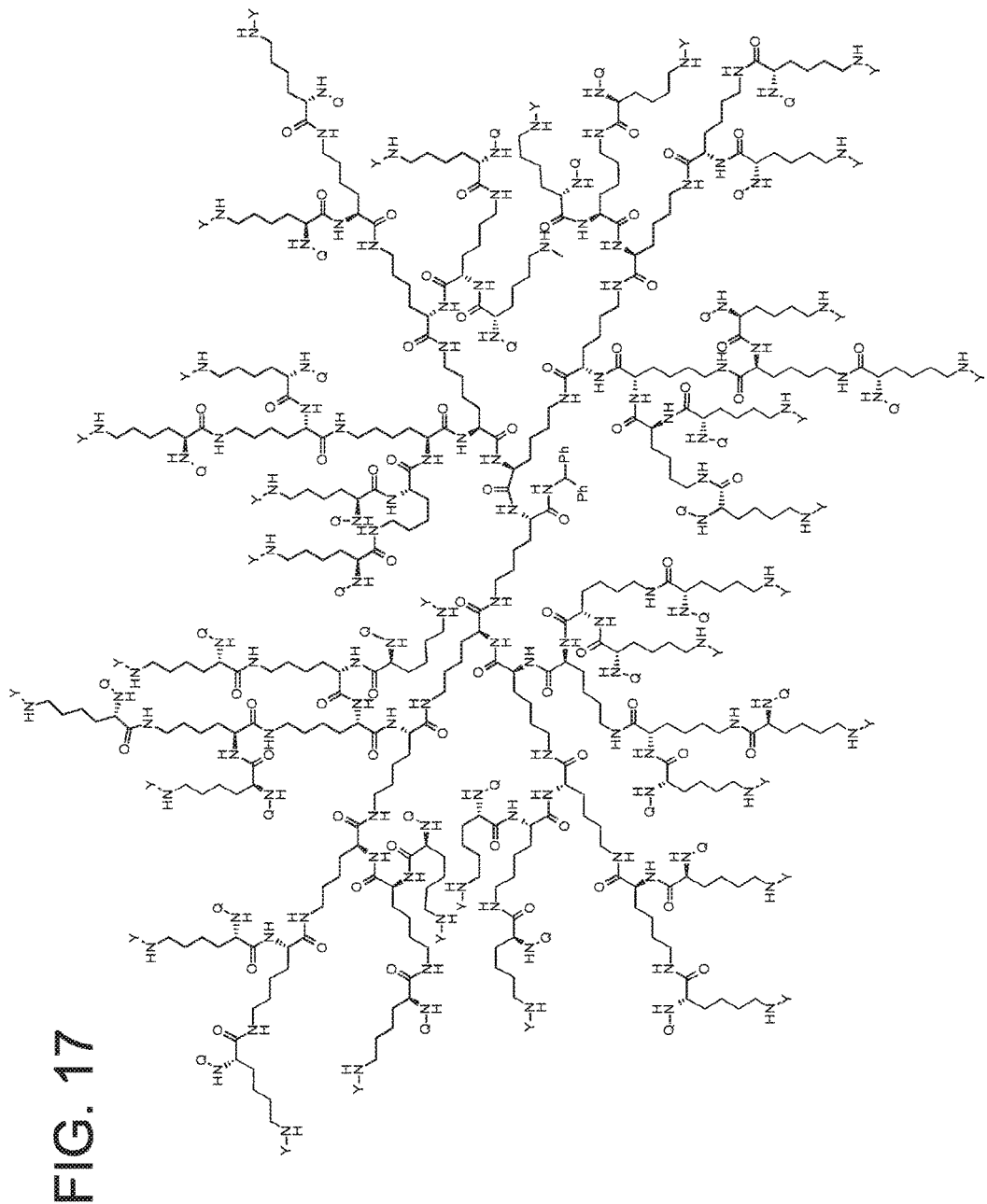
FIG. 17 displays the dendrimer of formula (V).

The results are shown in FIG. 15. Examples 6 and 9 at 50 mg/kg Compound A equivalent (195 and 185 mg/kg dendrimer, respectively) significantly inhibited tumor growth as compared to vehicle control with the macromolecules of Example 6 being slightly more efficacious as a monotherapy than the macromolecules of Example 9 at 50 mg/kg Compound A (185 mg/kg Example 9). Table 17 summarizes the tumor growth inhibition (TIC) and tumor growth delay (T-C) values calculated as % Inhibition & % Regression. The calculation is based on the geometric mean of RTV in each group.

On specific day, for each treated group, calculate Inhibition value by formula: Inhibition %=(CG−TG)*100/(CG−1), in which "CG" means the geometric mean of rtv of the control group and "TG" means the Geometric Mean of Relative Tumor Volume (rtv) of the treated group. "CG" should use the corresponding control group of the treated group when calculated. If Inhibition >100%, then it's necessary to calculate the Regression by formula: Regression=1−TG The TIC value is 63.5% for 50 mg/kg Compound A equivalent (195 mg/kg Example 6), 40.44% for 50 mg/kg Compound A equivalent (185 mg/kg Example 9) and 75.27% for 10 mg/kg rituximab. Thus, Example 6 and Example 9 dosed at 50 mg/kg Compound A equivalent are significantly active in this model. More significantly, a combination of Examples 6 and 9 at 10, 30, and 50 mg/kg Compound A equivalent with rituximab (10 mg/kg) resulted in tumor regression. Additionally, the combination treatment resulted in complete tumor regression in most animals whereas none were seen with the single drug treatments.

TABLE 17

Summary of efficacy data of Examples 6 and 9 in combination with rituximab

| | Treatment | % Inhibition (TIC) Day (41) | % Regression Day (41) | P-value Day (41) | T-C (Days) |
|---|---|---|---|---|---|
| 1 | Vehicle | | | | |
| 2 | Example 6 (50 mg/kg Compound A equivalent, 195 mg/kg Example 6) | 63.5 | | 0.0002 | |
| 3 | Example 9 (50 mg/kg Compound A equivalent, 185 mg/kg Example 6) | 40.44 | | 0.0420 | |

TABLE 17-continued

Summary of efficacy data of Examples 6 and 9 in combination with rituximab

| | Efficacy | | | |
|---|---|---|---|---|
| Treatment | % Inhibition (TIC) Day (41) | % Regression Day (41) | P-value Day (41) | T-C (Days) |
| 4 rituximab (10 mg/kg) | 75.27 | | 0.0010 | >16 |
| 5 rituximab (10 mg/kg) plus Example 6 (10 mg/kg Compound A equivalent, 39 mg/kg Example 6) | >100 | 97 | 0.0005 | >37 |
| 6 rituximab (10 mg/kg) plus Example 6 (30 mg/kg Compound A equivalent, 117 mg/kg Example 6) | >100 | 100 | <0.0001 | >37 |
| 7 rituximab (10 mg/kg) plus Example 6 (50 mg/kg Compound A equivalent, 195 mg/kg Example 6) | >100 | 100 | <0.0001 | >37 |
| 8 rituximab (10 mg/kg) plus Example 9 (10 mg/kg Compound A equivalent, 37 mg/kg Example 9) | >100 | 69 | 0.0230 | >37 |
| 9 rituximab (10 mg/kg) plus Example 9 30 mg/kg Compound A equivalent, 111 mg/kg Example 9) | >100 | 100 | <0.0001 | >37 |
| 10 rituximab (10 mg/kg) plus Example 9 (50 mg/kg Compound A equivalent, 185 mg/kg Example 9) | >100 | 100 | <0.0001 | >37 |

Example 19: Cardiovascular Telemetry Studies in the Rat

To evaluate the effects of Compound A and Example 5, 6, 8 and 9 on arterial blood pressure, heart rate, QA interval and electrocardiogram, male Han Wistar rats were surgically implanted under anesthesia with Data Sciences International rodent telemetry transmitters. The telemetry transmitters were placed in the abdominal muscle and the arterial blood pressure catheter was placed in the abdominal aorta. The ECG electrodes were sutured to the dorsal surface of the xiphoid process and at the anterior mediastinum.

Following telemetry transmitter implantation, a single 30-minute tail vein intravenous infusion of Compound A, or Example 5, 6 or 8 were administered to individual groups of rats (8 males/group for Compound A and 3 males/group for each dendrimer). Example 9 was administered to an individual group of rats (3 males/group) as a single intravenous tail vein bolus injection. Compound A was administered at dose levels of 0 and 10 mg/kg. Example 6 was administered at dose levels of 0, 35, 70 and 105 mg/kg (10, 20 and 30 mg/kg Compound A equivalent) and Examples 5 and 8 were administered at 0, 35 and 105 mg/kg (10 and 30 mg/kg Compound A equivalent) and Example 9 were administered at 0, 37 and 112 mg/kg (10 and 30 mg/kg Compound A equivalent).

Cardiovascular parameters were recorded continuously via receivers placed beneath the home cage for at least 1 hour pre-dose and up to 72 hours post-dose. Blood samples were taken to determine the level of plasma exposure of Compound A and all dendrimers, with clinical pathology and limited tissues for target organ histopathology taken from animals dosed with the macromolecule constructs only.

An infusion of Compound A was not tolerated and a total of three rats were found dead up to 5 hours after the start of the infusion. All animals dosed with the dendrimers survived to scheduled termination. Following administration of Compound A, a biphasic decrease in systolic and mean arterial blood pressure was noted between 1.5 to 16 hours after the start of infusion, which was accompanied by increases in heart rate between 2 to 10 hours after the start of the infusion. A decrease in QRS amplitude was also noted from 1 hour after the start of the infusion, which was still present at the end of the recording period. Cardiovascular changes for Example 6 were limited to a transient decrease in QRS amplitude between 2 to 8 hours post-dose in animals dosed at 120 mg/kg, with full recovery by 22 hours post-dose. Example 6 and all other dendrimers showed no cardiovascular changes up to 80 and 120 mg/kg, respectively.

Plasma transaminases were elevated in animals given ≥80 mg/kg of Example 6. No transaminase changes were noted in rats dosed up to 120 mg/kg of Example 5, 8 and 9. All dendrimers showed thrombocytopenia, consistent with the primary pharmacology.

Histopathological findings at ≥80 mg/kg of Example 6 included minimal skeletal muscle degeneration/necrosis, with findings in the heart (minimal endothelial cell apoptosis) and liver (minimal hepatocellular apoptosis) also seen in animals dosed at 120 mg/kg. Example 9 showed histopathological findings in the skeletal muscle (minimal skeletal muscle degeneration) at ≥40 mg/kg, with minimal hepatocellular apoptosis observed at 120 mg/kg only. Example 5 showed no treatment related histopathology up to 120 mg/kg, with histopathological findings for Example 8 limited to minimal hepatocellular necrosis at 120 mg/kg only.

In conclusion, these data illustrate the improved cardiovascular and liver histopathological profiles of Examples 5, 6, 8 and Example 9, when compared to Compound A.

One male and one female beagle dog were given Example 6 by intravenous bolus at ascending weekly doses of 4, 8, 12, 20, 30 and 45 mg/kg (1, 2, 3, 5, 7.5 and 11 mg/kg Compound A equivalent). The MTD of Example 6 in the dog is 45 mg/kg (11 mg/kg Compound A equivalent), which is an 11-fold improvement compared to Compound A.

A maximum tolerated dose study with Example 9 was conducted in the rat. Example 9 was administered to individual groups of Han Wistar male rats (3/group) by intravenous bolus at dose levels of 125, 250, 500, 1000 and 1500 mg/kg (9, 72, 145, 290 and 435 mg/kg Compound A equivalent). The MTD of Example 9 in the rat is 1000 mg/kg (290 mg/kg Compound A equivalent), which is a 29-fold improvement compared to Compound A.

In conclusion, these data illustrate an improved maximum tolerated dose of the Example 6 and Example 9, when compared to Compound A alone.

Figure 18:
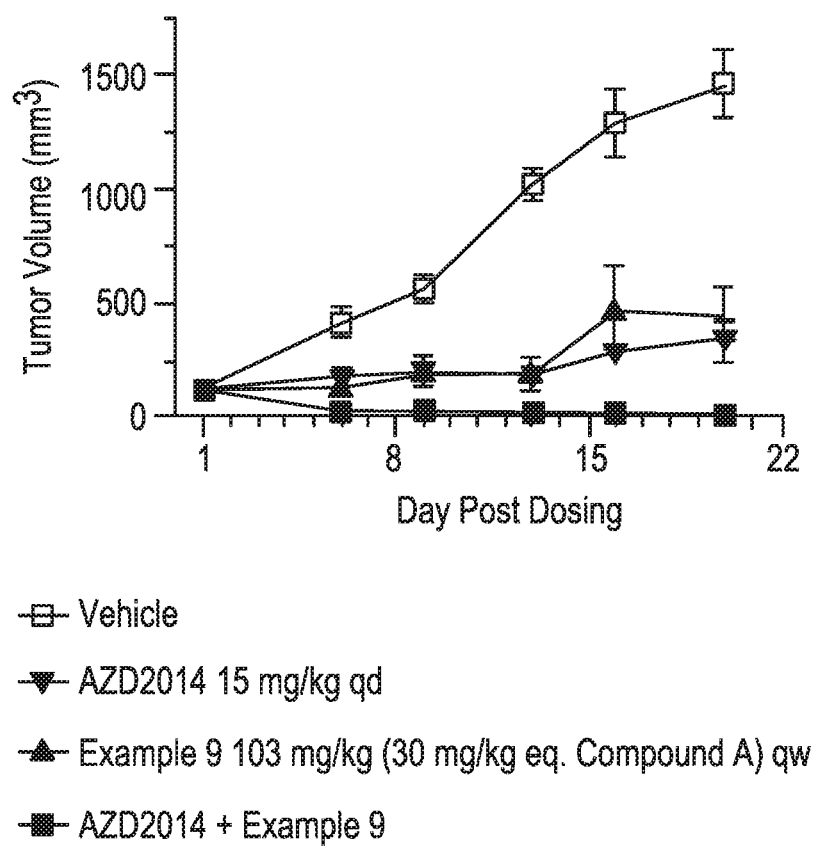
FIG. 18 illustrates the in vivo anti-tumor activity in a human small cell lung cancer tumor model exhibited by Example 9 in combination with the mTOR inhibitor AZD2014.

Example 21: Single Agent and Combination In Vivo Anti-Tumor Activity in a Human Small Cell Lung Cancer Tumor Model Example 9 and AZD2014 (vistusertib, an mTOR inhibitor shown below) induced single agent and combination anti-tumor activity in NCI-H1048 tumor bearing mice (FIG. 18). A weekly (qw) iv administration of Example 9 at 103 mg/kg (equivalent to 30 mg/kg Compound A) resulted in significant anti-tumor activity of 76% TGI (p<0.05). Administration of the mTOR inhibitor AZD2014 at 15 mg/kg daily (qd) resulted in significant anti-tumor activity of 84% TGI (p<0.05). Combination of Example 9 with AZD2014 resulted in 91% tumor regression (p<0.05 relative to single agent activity).

TABLE 18

Summary of the Cardiovascular Telemetry Studies in the Rat Following Intravenous Dosing of Compound A and Examples 6 and 9

| Parameter | Compound A 10 mg/kg | Example 6[a] 10 mg/kg | Example 6[a] 20 mg/kg | Example 6[a] 30 mg/kg | Example 9[a] 10 mg/kg | Example 9[a] 30 mg/kg |
|---|---|---|---|---|---|---|
| In-life | 3 found dead | All dose levels tolerated | | | All dose levels tolerated | |
| Platelets | Not assessed | ↓ | ↓ | ↓ | ↓ | ↓ |
| Transaminases | Not assessed | NAD | ↑ | ↑ | NAD | NAD |
| Cardiovascular | ↓ QRS amplitude ↓ blood pressure ↑ heart rate | NAD | NAD | ↓ QRS amplitude | NAD | NAD |
| Histopathology Skeletal muscle - degeneration/necrosis Heart - endothelial cell apoptosis Liver - hepatocellular apoptosis | Not assessed | 0/3 0/3 0/3 | 2/3 0/3 0/3 | 2/3 1/3 3/3 | 1/3 0/3 0/3 | 1/3 0/3 1/3 |

[a]dose levels are expressed as Compound A equivalent
NAD = no abnormalities detected Example 20: Maximum Tolerated Dose Toxicity Studies in the Rat and Dog Maximum tolerated dose (MTD) studies with Example 6 were conducted in the rat and dog. Example 6 was administered to individual groups of Han Wistar male or female rats (up to 4/group) by intravenous bolus at dose levels of 125, 200, 225 and 250 mg/kg (31, 50, 56 and 62 mg/kg Compound A equivalent). The MTD of Example 6 in the rat was 225 mg/kg (56 mg/kg Compound A equivalent), which is a 5-fold improvement compared to Compound A alone.

Example 9 was formulated in citrate/phosphate buffer pH 5.0 containing 4.5% w/v glucose and dosed intravenously (iv) in a volume of 5 ml/kg. AZD2014 was formulated in 0.5% hydroxypropyl methylcellulose/0.1% Tween 80 and dosed oral in a volume of 10 ml/kg 5×10⁶ NCI-H1048 tumor cells were injected subcutaneously in the right flank of C.B.-17 SCID female mice in a volume of 0.1 mL containing 50% matrigel. Tumor volume (measured by caliper) was calculated using the formula:length (mm)×width (mm)$^2$× 0.52. For efficacy studies, mice were randomized based on tumor volume and growth inhibition was assessed by comparison of the differences in tumor volume between control and treated groups. Dosing began when mean tumor volume reached approximately 124 mm³.

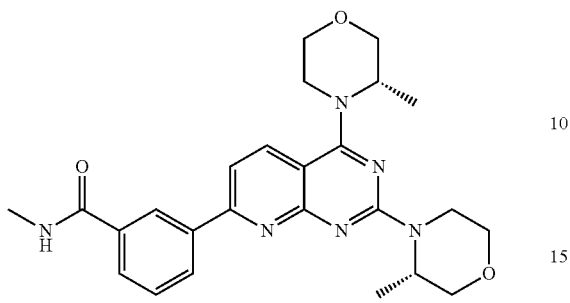

AZD2014

Example 22: Single Agent and Combination In Vivo Anti-Tumor Activity in a Human DLBCL Model 5×10⁶ OCI-Ly10 tumor cells were injected subcutaneously in the right flank of C.B.-17 SCID female mice in a volume of 0.1 mL containing 50% matrigel. Example 9 was formulated in citrate/phosphate buffer pH 5.0, diluted 1 to 10 with 5% glucose containing 1% w/v Kolliphor HS15, and dosed as a weekly intravenous (iv) administration at a volume of 5 mL/kg at a dose of 103 mg/kg (30 mg/kg API). Acalabrutinib was formulated in 0.5% hydroxypropyl methyl cellulose/0.2% Tween 80, and dosed twice a day (bid) as an oral (po) administration at a volume of 10 mL/kg at a dose of 12.5 mg/kg. Tumor volumes (measured by caliper), animal body weight, and tumor condition were recorded twice weekly for the duration of the study. The tumor volume was calculated using the formula:length (mm)×width (mm)²×0.52. For efficacy studies, growth inhibition from the start of treatment was assessed by comparison of the differences in tumor volume between control and treated groups. Dosing began when mean tumor size reached approximately 166 mm3.

Figure 19:
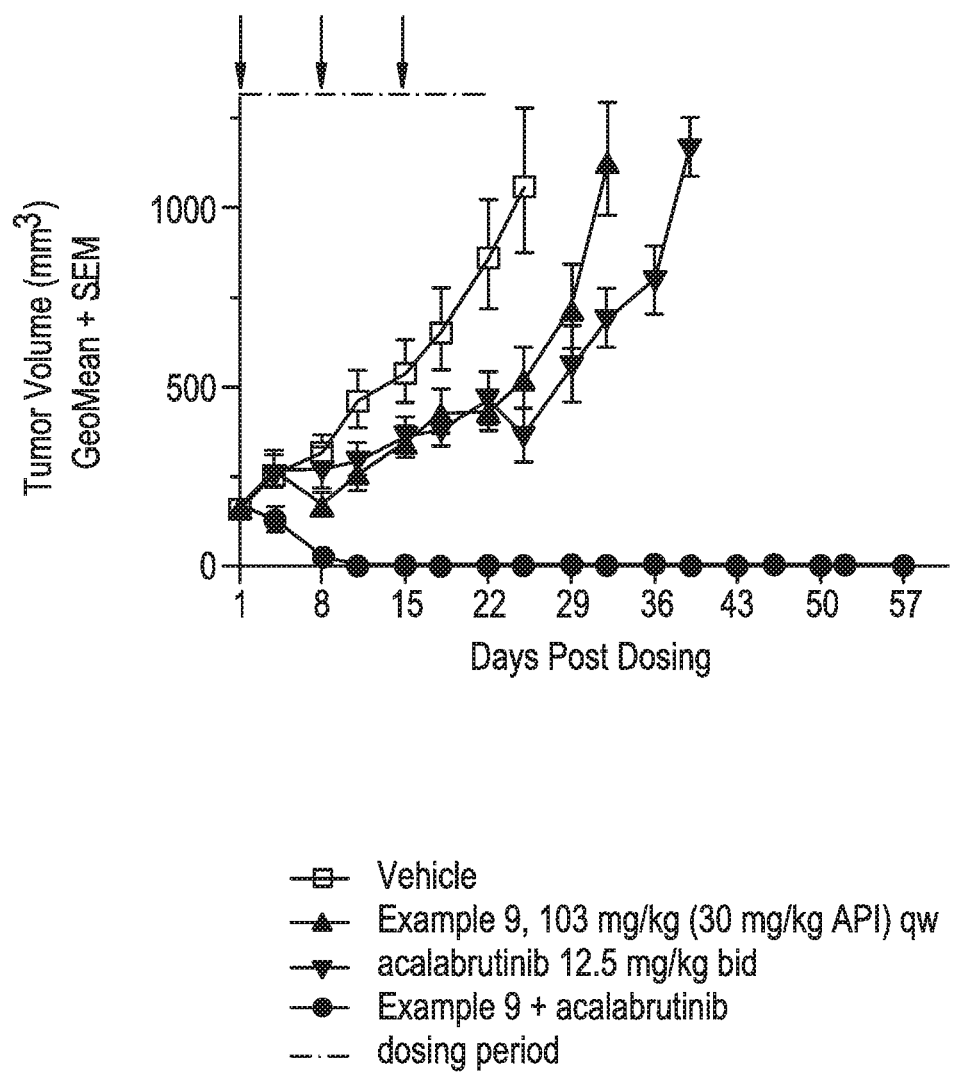
FIG. 19 illustrates the in vivo anti-tumor activity in a human DLBCL tumor model exhibited by Example 9 in combination with acalabrutinib.

As shown in FIG. 19, Combining Example 9 with acalabrutinib resulted in significant in vivo anti-tumor activity in the OCI-Ly10 DLBCL xenograft model. Weekly iv administration of 103 mg/kg of example 9 (30 mg/kg Compound A) in combination with twice a day oral administration of 12.5 mg/kg acalabrutinib resulted in complete regression in 8 out of 8 tumor bearing mice 10 days after treatment initiation. Complete regressions were sustained even after the end of treatment (3 weeks treatment with 35 days follow up). In contrast, single agent Example 9 or acalabrutinib showed relatively modest single agent activity, reaching approximately 64% and 58% tumor growth inhibition (TGI) respectively.

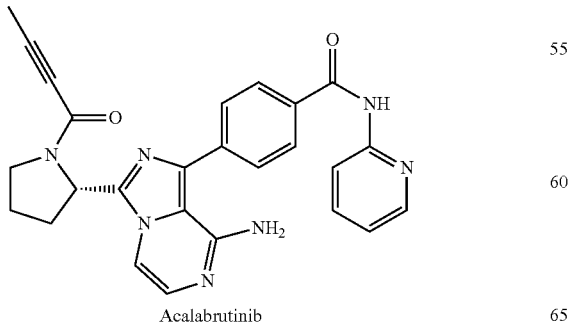

Acalabrutinib

The invention claimed is:
1. A dendrimer of formula (IV):
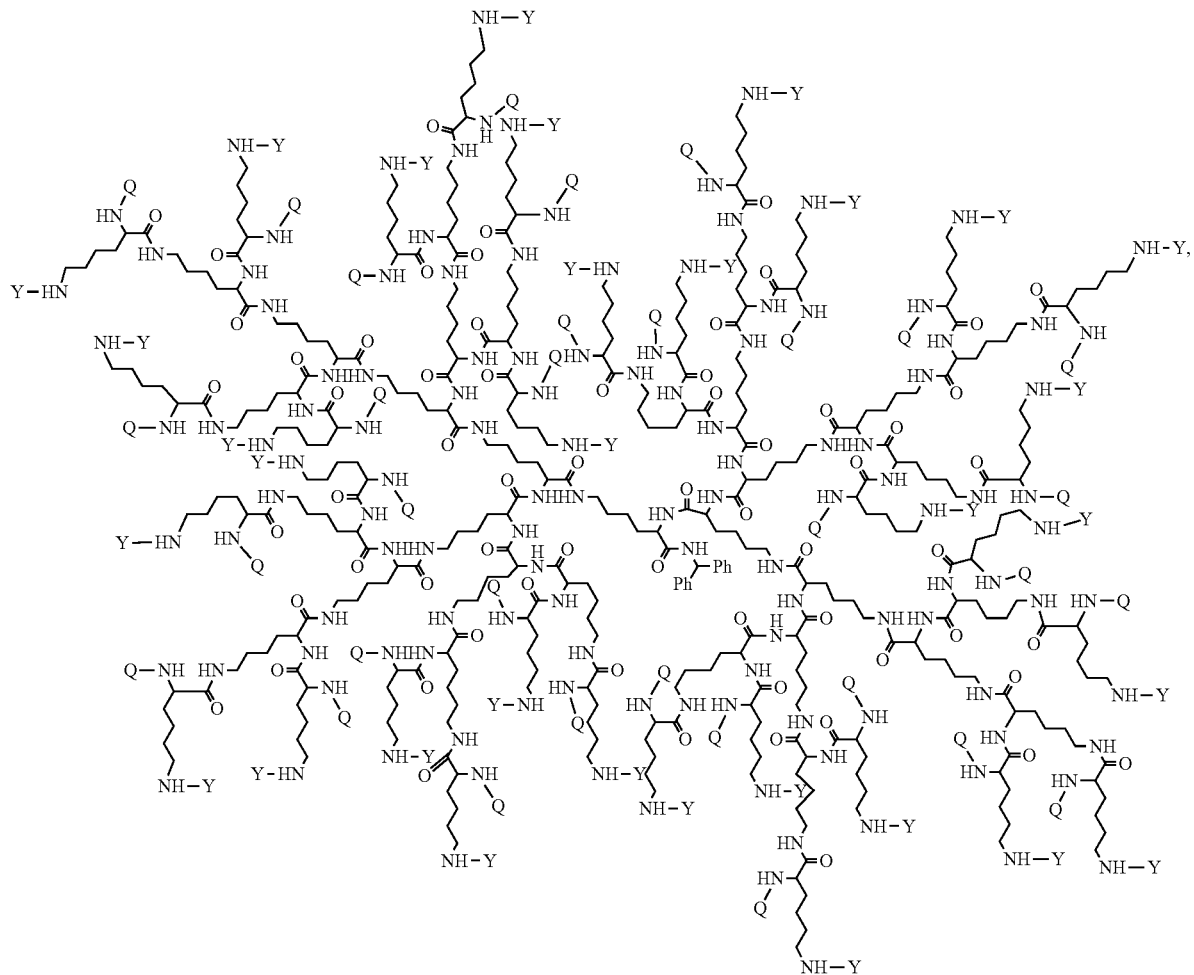
or a pharmaceutically acceptable salt thereof,
wherein
Y is PEG$_{1800\text{-}2400}$ or H;
Q is H or L-AA, in which L-AA has the structure:
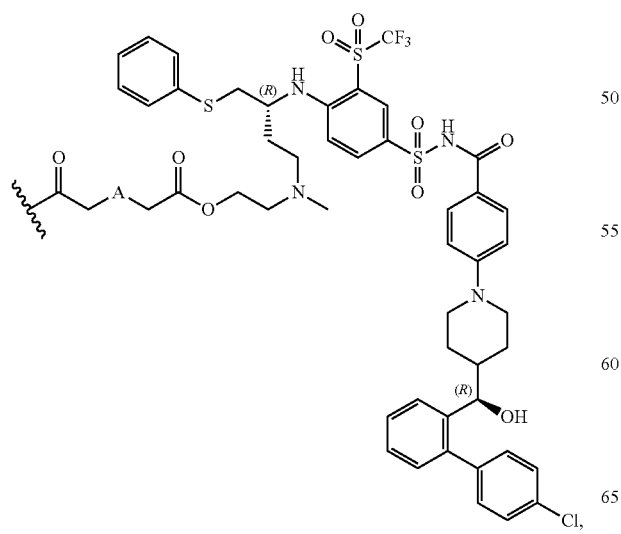

and
A is —N(CH$_3$),
provided that if the sum of PEG$_{1800-2400}$ and L-AA is less than 64, the remaining Q and Y moieties are H, and provided that at least one Q is L-AA.
2. A dendrimer of formula (V):
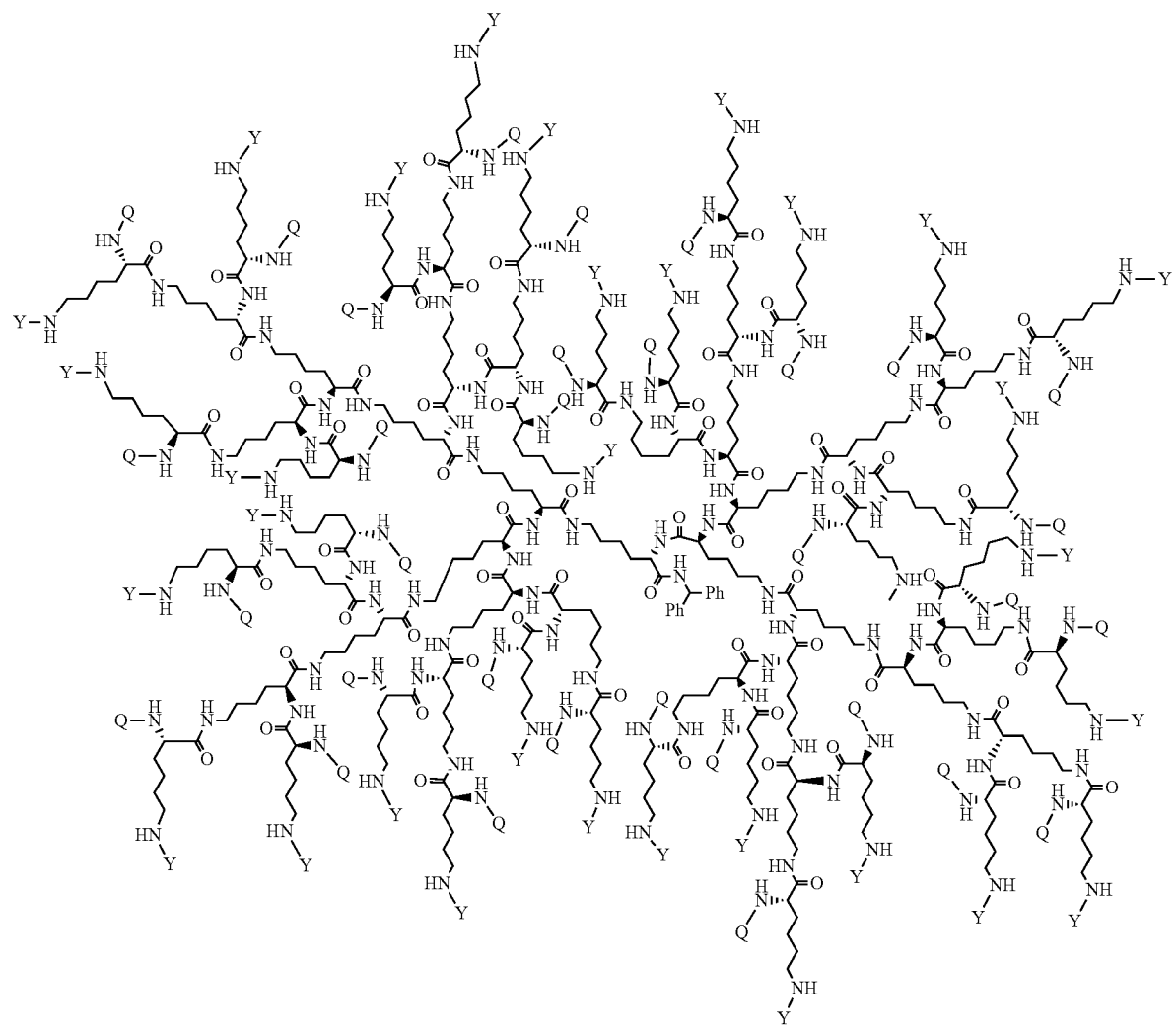
or a pharmaceutically acceptable salt thereof, wherein
Y is PEG$_{1800-2400}$ or H;

Q is H or L-AA, wherein L-AA has the structure:

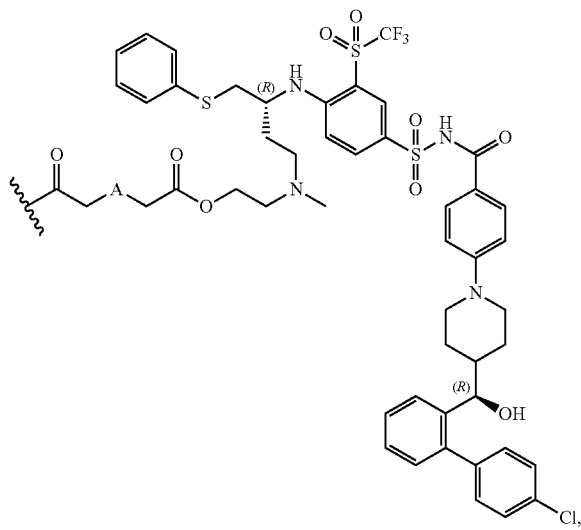

A is —N(CH$_3$),
provided that if the sum of PEG$_{1800-2400}$ and L-AA is less than 64, the remaining Q and Y moieties are H, and provided that at least one Q is L-AA.

3. The dendrimer of claim 1 or 2, or a pharmaceutically acceptable salt thereof, wherein the sum of PEG$_{1800-2400}$ and L-AA is an integer between 50 and 64.

4. The dendrimer of claim 3, or a pharmaceutically acceptable salt thereof, wherein the sum of PEG$_{1800-2400}$ and L-AA is an integer between 58 and 64.

5. The dendrimer of claim 1 or 2, or a pharmaceutically acceptable salt thereof, wherein the dendrimer has between 25 and 32 PEG$_{1800-2400}$.

6. The dendrimer of claim 5, or a pharmaceutically acceptable salt thereof, wherein the dendrimer has between 29 and 32 PEG$_{1800-2400}$.

7. The dendrimer of claim 1 or 2, or a pharmaceutically acceptable salt thereof, wherein the dendrimer has between 25 and 32 L-AA.

8. The dendrimer of claim 7, or a pharmaceutically acceptable salt thereof, wherein the dendrimer has between 29 and 32 L-AA.

9. The dendrimer of claim 1 or 2, or a pharmaceutically acceptable salt thereof, wherein the dendrimer has between 0 and 14 hydrogens at the Q and/or Y positions.

10. The dendrimer of claim 9, or a pharmaceutically acceptable salt thereof, wherein the dendrimer has between 0 and 6 hydrogens at the Q and/or Y positions.

11. The dendrimer of claim 1 or 2, or a pharmaceutically acceptable salt thereof, wherein the PEG has an average molecular weight of between about 2000 and 2200 Da.

12. The dendrimer of claim 1 or 2, or a pharmaceutically acceptable salt thereof, wherein the PEG has a PDI of between about 1.00 and 1.10.

13. The dendrimer of claim 12, or a pharmaceutically acceptable salt thereof, wherein the PEG has a PDI of about 1.05.

14. The dendrimer of claim 1 or 2, or a pharmaceutically acceptable salt thereof, wherein the dendrimer has a molecular weight of between about 90 and 120 kDa.

15. The dendrimer of claim 14, or a pharmaceutically acceptable salt thereof, wherein the dendrimer has a molecular weight of between about 103 and 107 kDa.

16. A pharmaceutical composition comprising a dendrimer of claim 1 or 2, or a pharmaceutically acceptable salt thereof, and a pharmaceutically acceptable excipient, carrier or diluent.

* * * * *